(12) United States Patent
Parvulescu et al.

(10) Patent No.: US 9,943,838 B2
(45) Date of Patent: Apr. 17, 2018

(54) REGENERATION OF A TITANIUM CONTAINING ZEOLITE

(71) Applicants: BASF SE, Ludwigshafen (DE); DOW GLOBAL TECHNOLOGIES LLC, Midland, MI (US)

(72) Inventors: Andrei-Nicolae Parvulescu, Heidelberg (DE); Ulrich Mueller, Neustadt (DE); Joaquim Henrique Teles, Waldsee (DE); Bianca Seelig, Cologne (DE); Philip Kampe, Singapore (SG); Markus Weber, Limburgerhof (DE); Peter Resch, Hettenleidelheim (DE); Christian Bartosch, Mannheim (DE); Dominic Riedel, Mannheim (DE); Daniel Urbanczyk, Griesheim (DE); Alexander Schroeder, Wattenheim (DE); Ulrike Wegerle, Worms (DE)

(73) Assignees: BASF SE, Ludwigshafen (DE); Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/907,714

(22) PCT Filed: Jul. 16, 2014

(86) PCT No.: PCT/EP2014/065256
§ 371 (c)(1),
(2) Date: Jan. 26, 2016

(87) PCT Pub. No.: WO2015/010994
PCT Pub. Date: Jan. 29, 2015

(65) Prior Publication Data
US 2016/0332152 A1    Nov. 17, 2016

(30) Foreign Application Priority Data

Jul. 24, 2013 (EP) ..................... 13177916

(51) Int. Cl.
*C07D 301/12* (2006.01)
*B01J 29/90* (2006.01)
(Continued)

(52) U.S. Cl.
CPC ........... *B01J 29/90* (2013.01); *B01J 29/7088* (2013.01); *B01J 29/89* (2013.01); *B01J 35/00* (2013.01);
(Continued)

(58) Field of Classification Search
CPC ........ B01J 29/90; B01J 29/7088; B01J 29/89; B01J 37/08; B01J 37/30; B01J 37/0203;
(Continued)

(56) References Cited

U.S. PATENT DOCUMENTS 5,916,835 A    6/1999 Carroll et al.
6,114,551 A    9/2000 Levin et al.
(Continued)

FOREIGN PATENT DOCUMENTS

EP    0 079 007 A    5/1983
EP    0 934 116 A1    8/1999
(Continued)

OTHER PUBLICATIONS

Wikipedia, Inert Gas, Dec. 2012 , p. 3.*
International Search Report and Written Opinion dated Sep. 30, 2014 for PCT/EP2014/065256 filed on Jul. 16, 2014.

*Primary Examiner* — Taylor V Oh
(74) *Attorney, Agent, or Firm* — Oblon, McClelland, Maier & Neustadt, L.L.P.

(57) ABSTRACT

The present invention relates to a process for the regeneration of a catalyst comprising a titanium-containing zeolite, said catalyst having been used in a process for the preparation of an olefin oxide and having phosphate deposited thereon, said process for the regeneration comprising the
(Continued)

steps: (a) separating the reaction mixture from the catalyst, (b) washing the catalyst obtained from (a) with liquid aqueous system; (c) optionally drying the catalyst obtained from (b) in a gas stream comprising an inert gas at a temperature of less than 300° C.; (d) calcining the catalyst obtained from (c) in a gas stream comprising oxygen at a temperature of at least 300° C.

19 Claims, 6 Drawing Sheets

(51) Int. Cl.

| | | |
|---|---|---|
| *B01J 37/06* | (2006.01) | |
| *B01J 37/10* | (2006.01) | |
| *B01J 38/48* | (2006.01) | |
| *B01J 29/70* | (2006.01) | |
| *B01J 29/89* | (2006.01) | |
| *B01J 35/00* | (2006.01) | |
| *B01J 37/00* | (2006.01) | |
| *B01J 37/02* | (2006.01) | |
| *C07D 303/04* | (2006.01) | |
| *B01J 37/08* | (2006.01) | |
| *B01J 37/30* | (2006.01) | |
| *B01J 38/02* | (2006.01) | |
| *B01J 38/06* | (2006.01) | |

(52) U.S. Cl.
 CPC ....... *B01J 37/0009* (2013.01); *B01J 37/0045* (2013.01); *B01J 37/0201* (2013.01); *B01J 37/0203* (2013.01); *B01J 37/06* (2013.01); *B01J 37/08* (2013.01); *B01J 37/10* (2013.01); *B01J 37/30* (2013.01); *B01J 38/02* (2013.01); *B01J 38/06* (2013.01); *B01J 38/48* (2013.01); *C07D 301/12* (2013.01); *C07D 303/04* (2013.01); *B01J 2229/183* (2013.01); *B01J 2229/186* (2013.01); *B01J 2229/42* (2013.01); *Y02P 20/584* (2015.11)

(58) Field of Classification Search
 CPC ................ B01J 37/0009; B01J 37/0045; B01J 37/0201; B01J 37/061; B01J 38/02; B01J 38/06; B01J 38/48; B01J 2229/183; B01J 2229/42; B01J 2229/186; C07D 301/12; C07D 303/04; Y02P 20/584
 USPC ........................................................ 549/531
 See application file for complete search history.

(56) References Cited

U.S. PATENT DOCUMENTS

| | | |
|---|---|---|
| 2003/0162983 A1 | 8/2003 | Strebelle et al. |
| 2003/0187284 A1 | 10/2003 | Teles et al. |
| 2004/0058798 A1 | 3/2004 | Han et al. |
| 2005/0054864 A1 | 3/2005 | Strebelle et al. |
| 2007/0043226 A1 | 2/2007 | Muller et al. |
| 2007/0149790 A1 | 6/2007 | Strebelle et al. |
| 2008/0132718 A1 | 6/2008 | Strebelle et al. |
| 2012/0142950 A1 | 6/2012 | Teles et al. |
| 2013/0005999 A1 | 1/2013 | Kawabata et al. |

FOREIGN PATENT DOCUMENTS

| | | |
|---|---|---|
| EP | 1 122 249 A1 | 8/2001 |
| EP | 1 221 442 A1 | 7/2002 |
| EP | 1 371 414 A1 | 12/2003 |
| WO | 98/55229 A1 | 12/1998 |
| WO | 2005/000827 A1 | 1/2005 |
| WO | 2007/013739 A1 | 2/2007 |
| WO | 2011/064191 A1 | 6/2011 |
| WO | 2011/115234 A1 | 9/2011 |

\* cited by examiner

REGENERATION OF A TITANIUM CONTAINING ZEOLITE

The present invention relates to a process for the regeneration of a catalyst comprising a titanium containing zeolite, said catalyst having been used in a process for the preparation of an olefin oxide and having a potassium salt deposited thereon, said process for the regeneration comprising the steps: (a) separating the reaction mixture from the catalyst, (b) washing the catalyst obtained from (a) with a liquid aqueous system; (c) optionally drying the catalyst obtained from (b) in a gas stream comprising an inert gas at a temperature of less than 300° C.; (d) calcining the catalyst obtained from (c) in a gas stream comprising oxygen at a temperature of at least 300° C. Further, the present invention relates to a regenerated catalyst comprising a titanium containing zeolite as catalytically active material, obtainable or obtained by the process of the present invention.

In the past years, various titanium-containing zeolites have been developed which are useful in catalyzing organic reactions such as the conversion of olefins to epoxides. For example, WO-A 98/55229 and WO-A 2011/064191 disclose the production and further the use of heterogeneous titanium-containing zeolites in epoxidation.

Heterogeneous titanium-containing zeolites are of great industrial interest and in this context economical and environmental considerations are of significant relevance. An efficient regeneration of such zeolites for subsequent re-use in the catalysis of organic reactions would be strongly preferred over their replacement with fresh catalyst.

EP-A 0 934 116 discloses a process for the regeneration of a spent catalyst composed of titanium silicalite, resulting from the synthesis of an epoxide by reaction between an olefin and hydrogen peroxide. The treatment of the spent catalyst comprises washing with methanol, followed by drying in a stream of nitrogen gas at 75° C. and further followed by the actual regenerations step, which is heating at 300° C. for 7 hours. Methanol, which must be provided in large amounts and sufficiently high purity, is a valuable organic compound and requires for its reuse an expensive and time consuming recovery.

EP-A 1 371 414 discloses a process for the regeneration of a silicon oxide catalyst containing titanium following the epoxidation of cumene, comprising passing liquid propene through the spent catalyst at a temperature not lower than the maximum reaction of the epoxidation reaction. Propene is equally a valuable organic compound, and using it in large amounts at industrial scale would be economically unfavorable.

EP-A 1 221 442 discloses the regeneration of an titanium zeolite catalyst used in an epoxidation of olefins with hydrogen peroxide, the process comprising performing the epoxidation reaction, wherein the regeneration of the spent catalyst is carried out with hydrogen peroxide in the presence of the olefin whereby the epoxidation reaction is continued and wherein the regeneration is achieved by reversal of the feed direction of the hydrogen peroxide. Hydrogen peroxide is also a valuable educt and as such difficult to handle due to its tendency to decompose spontaneously.

WO-A 2005/000827 discloses the regeneration of a titanium silicalite catalyst following a process for the continuous expoxidation of propene with hydrogen peroxide. The catalyst is periodically regenerated with a methanol solvent at a temperature of at least 100° C. Is indicated above, methanol is a valuable organic compound which requires an expensive and time consuming recovery. Also, after regeneration, the epoxidation has to be restarted at a higher temperature compared with fresh catalyst in the WO-A 2005/000827.

WO-A 2007/013739 discloses the regeneration of a titanium containing molecular sieve wherein, after a pretreatment of the spent catalyst with water or alcohol, the thus pretreated catalyst is brought into contact with a mixture which comprises hydrogen peroxide, water, and alcohol. This process thus includes two mandatory and subsequent steps in which the spent catalyst is brought into contact with two different solution.

US 2003/0187284 A1 discloses a method for producing an epoxide in the presence of a zeolite catalyst and the regeneration of the catalyst by treating it with a solution comprising an acid with a pKa value of less than 6.

US 2012/142950 A1 discloses a continuous process for the production of propylene oxide comprising reacting propene with hydrogen peroxide in methanolic solution in the presence of a titanium silicalite-1 catalyst to obtain propylene oxide.

WO 2011/115234 A1 discloses a method for regenerating titanosilicate catalysts.

US 2004/058798 A1 discloses a method for regeneration of titanium-containing silicone oxide catalysts by heating the used catalysts at a temperature of at least 400° C. in the presence of an oxygen-containing gas stream.

U.S. Pat. No. 5,916,835 A discloses a method of regenerating used non-zeolitic heterogeneous catalysts.

Therefore, it was an object of the present invention to provide a simple and cost-effective process for regeneration of a catalyst comprising a titanium containing zeolite as catalytically active material used in an epoxidation of olefins. It was a further object of the present invention to provide a regenerated catalyst comprising a titanium containing zeolite as catalytically active material which may be readily reused in the catalysis of the epoxidation of olefins.

Thus, the present invention relates to a process for the regeneration of a catalyst comprising a titanium containing zeolite as catalytically active material, said catalyst having been used in a process for the preparation of an olefin oxide comprising (i) providing a mixture comprising an organic solvent, an olefin, an epoxidation agent and an at least partially dissolved potassium comprising salt;

(ii) subjecting the mixture provided in (i) in a reactor to epoxidation conditions in the presence of the catalyst, obtaining a mixture comprising the organic solvent and the olefin oxide, and obtaining the catalyst having a potassium salt deposited thereon;

said process for the regeneration comprising (a) separating the mixture obtained from (ii) from the catalyst;

(b) washing the catalyst obtained from (a) with a liquid aqueous system;

(c) optionally drying the catalyst obtained from (b) in a gas stream comprising an inert gas at a temperature of less than 300° C.;

(d) calcining the catalyst obtained from (b) or (c) in a gas stream comprising oxygen at a temperature of at least 300° C.

Surprisingly, according to the regeneration process of the present invention, which comprises washing spent catalyst comprising a titanium containing zeolite with a liquid aqueous system, combined with optional drying, and further calcining, a regenerated catalyst comprising a titanium containing zeolite with excellent catalytic properties is obtained which may be readily reused, for example in the process for the preparation of an olefin oxide.

In this respect, the inventors found out that after subjecting the spent catalyst comprising a titanium containing zeolite as catalytically active material to the regeneration of the present invention, its activity and selectivity is over a long term comparable with the activity of the respective fresh catalyst comprising a titanium containing zeolite. Such a favorable result may be obtained after performing only one cycle of regeneration steps (a) to (d).

Further, it was surprisingly found that even repeated cycles of steps (a) to (b) did not affect the activity and selectivity of the catalyst comprising a titanium containing zeolite as catalytically active material in an unfavorable way. The regeneration according to steps (a) to (b) of the present invention has thus proven to be a mild process to which the same catalytic material may be submitted repeatedly, since no deteriorating effect on the catalytic activity and thus, presumably, on the zeolitic structure have been observed after several repetitions of steps (a) to (b).

Step (a)

The first regeneration step (a) requires separating the reaction mixture resulting from the epoxidation reaction of an olefin from the catalyst which comprises a titanium containing zeolite as catalytically active material.

This separation of the reaction mixture form the spent catalyst comprising a titanium containing zeolite can be achieved in any suitable manner, such as pumping, draining, decanting, filtrating, and the like. Preferably, in case the epoxidation reaction is carried out in batch mode, it is preferred to separate the mixture obtained from (ii) from the spent catalyst by filtration. In case the epoxidation reaction is carried out in continuous mode, it is preferred to separate the mixture obtained from (ii) from the spent catalyst by stopping to subject the mixture provided in (i) to epoxidation conditions according to (ii) and subject the spent catalyst to the regeneration step (b) once all of the mixture obtained from (ii) has left the reactor in which the epoxidation had been carried out, either in the reactor or in any other suitable vessel after having taken the spent catalyst out of the reactor.

If the spent catalyst comprising a titanium containing zeolite is removed from the reactor following steps (i) and (ii) and regenerated in a separate vessel, only a short interruption of the production process can be realized since the reactor can be refilled quickly with a second catalyst charge enabling the epoxidation reaction to be restarted immediately.

Step (b)

After the separation in (a), the spent catalyst comprising a titanium containing zeolite is washed with a liquid aqueous system according to (b).

The liquid aqueous system employed in (b) preferably contains at least 75 weight-%, preferably at least 90 weight-%, more preferably at least 95 weight-%, more preferably at least 99 weight-%, more preferably at least 99.9 weight-% water, more preferably at least 99.99 weight-% water, more preferably at least 99.999 weight-% water, based on the total weight of the liquid aqueous system. According to an embodiment of the present invention, the liquid aqueous system employed in (b) is water, preferably de-ionized water.

In the present process, the temperature and pressure conditions in step (b) are chosen so that the aqueous system is maintained in a liquid state of matter for at least 90%, preferably at least 95%, more preferably at least 99% of the time of washing. Preferably, the aqueous system is in its liquid state during the time of washing.

Preferably, the washing in (b) with a liquid aqueous system is performed at a pressure in the range of from 0.5 to 2 bar, more preferably from 0.8 to 1.5 bar, more preferably from 1.0 to 1.4 bar. Preferably, the washing in (b) with a liquid aqueous system is performed at a temperature of the liquid aqueous system in the range of from 25 to 95° C., more preferably from 40 to 90° C., more preferably from 60 to 80° C. More preferably, the washing in (b) with a liquid aqueous system is performed at a pressure in the range of from 0.8 to 1.5 bar, preferably from 1.0 to 1.4 bar, and a temperature in the range of from 40 to 90° C., preferably from 60 to 80° C. More preferably, the washing in (b) with a liquid aqueous system is performed at a pressure in the range of from 1.0 to 1.4 bar and a temperature in the range of from 60 to 80° C.

Therefore, the present invention preferably relates to the process as described above, wherein in (b), the catalyst obtained from (a) is washed with a liquid aqueous system which contains at least 99.9 weight-% water, more preferably at least 99.99 weight-% water, more preferably at least 99.999 weight-% water, based on the total weight of the liquid aqueous system, at a pressure in the range of from 0.8 to 1.5 bar, preferably from 1.0 to 1.4 bar, and a temperature in the range of from 40 to 90° C., preferably from 60 to 80° C.

Generally, the pH of the liquid aqueous system according to (b) is not subject to specific restrictions. Depending on the preferred water content of the liquid aqueous system, the pH value can be in the range of from 4 to 10, preferably in the range of from 5 to 9, more preferably in the range of from 6 to 8. Preferably, the pH is in the range of from 6.5 to 7.5, more preferably from 6.6 to 7.4, more preferably from 6.7 to 7.3, more preferably from 6.8 to 7.2. The pH is to be understood as being determined using a pH sensitive glass electrode wherein the liquid aqueous system is in an inert atmosphere which avoids, for example, that the liquid aqueous system comes into contact with atmospheric carbon dioxide which, if absorbed in the liquid aqueous system, would reduce the pH.

Preferably, no acid treatment of the catalyst is carried out in (b). Thus, it is preferred that the liquid aqueous system is free of compounds with a pKa value of 8 or less, preferably of 6 or less. "Free of compounds with a pKa value of" is to be understood in the context of the present invention that the liquid aqueous system comprises less than 0.1 wt.-% of such compounds, preferably less than 0.01 wt.-%, preferably less than 0.001 wt.-%, more preferably less than 0.0001 wt.-%, more preferably less than 0.00001 wt.-%, and more preferably less than 0.000001 wt.-%.

More preferably, no acid treatment of the catalyst is carried out in the entire process for the regeneration according to the present invention. Thus, it is preferred that no compounds with a pKa value of 8 or less, preferably of 6 or less, are employed in the entire process for the regeneration according to the present invention.

Preferably, the liquid aqueous system in (b) comprises less than 10 weight-% methanol, more preferably less than 5 weight-% methanol, more preferably less than 1 weight-% methanol, preferably less than 0.1 weight-% methanol, more preferably less than 0.01 weight-% methanol, and more preferably less than 0.001 weight-% of methanol, based on the total weight of the liquid aqueous system.

Surprisingly, it was found out that under these conditions of step (b), the washing of the catalyst comprising a titanium containing zeolite with an aqueous system results in essentially no change of the zeolitic structure of the titanium containing zeolite. Thus, it was found that the contacting according to (b) has no disadvantageous effects on the catalytic activity of the catalyst comprising a titanium containing zeolite.

Continuous Mode

According to a preferred embodiment of the present invention, the washing in (b) is performed in continuous mode wherein the catalyst is continuously contacted by a stream of the liquid aqueous system which is passed over the catalyst.

Preferably, the washing in continuous mode is performed at a weight hourly space velocity (WHSV) in the range of from 1 to 20 $h^{-1}$, more preferably from 5 to 15 $h^{-1}$, more preferably from 5 to 10 $h^{-1}$. The weight hourly space velocity in (b) is defined by the mass flow rate of the liquid aqueous system divided by the mass of the catalyst comprising a titanium containing zeolite subjected to regeneration.

According to this embodiment, it is possible to carry out the washing of the catalyst in the reactor in which the epoxidation reaction according to (ii) was carried out. In this case, as mentioned above, it is preferred to stop to subject the mixture provided in (i) to epoxidation conditions according to (ii) and subject the spent catalyst to the regeneration step (b) in continuous mode once all of the mixture obtained from (ii) has left the reactor in which the epoxidation had been carried out in the reactor. It is also possible to remove the spent catalyst, once all of the mixture obtained from (ii) has left the reactor, from the reactor, fill the catalyst in another suitable vessel in which a continuous washing can be carried out, and subject the catalyst to a continuous washing according to (b).

Therefore, the present invention preferably relates to the process as described above, wherein in (b), the catalyst obtained from (a) is washed in continuous mode with a liquid aqueous system which contains at least 99.9 weight-% water, more preferably at least 99.99 weight-% water, more preferably at least 99.999 weight-% water, based on the total weight of the liquid aqueous system, at a pressure in the range of from 0.8 to 1.5 bar, preferably from 1.0 to 1.4 bar, and a temperature in the range of from 40 to 90° C., preferably from 60 to 80° C., wherein the washing in continuous mode is carried out in the reactor according to (ii).

Batch Mode

According to another embodiment of the present invention, the washing in (b) is performed in batch mode wherein the catalyst is contacted once or several times with a specific amount of liquid system. For example, it is preferred that the washing in (b) is performed by immersing the catalyst in the liquid aqueous system. During the regeneration, it is possible to subject the mixture obtained in (ii), including or excluding the catalyst, to stirring. It is conceivable that when the washing in (b) is performed in batch mode, the liquid aqueous system may be replaced one ore more times.

According to this embodiment, it is possible to carry out the washing of the catalyst in the reactor in which the epoxidation reaction according to (ii) was carried out. In this case, as mentioned above, it is preferred to stop to subject the mixture provided in (i) to epoxidation conditions according to (ii) and subject the spent catalyst to the regeneration step (b) in batch mode once all of the mixture obtained from (ii) has left the reactor in which the epoxidation had been carried out in the reactor. It is also possible to remove the spent catalyst, once all of the mixture obtained from (ii) has left the reactor, from the reactor, fill the catalyst in another suitable vessel in which a batch washing can be carried out, and subject the catalyst to a batch washing according to (b).

Therefore, the present invention preferably relates to the process as described above, wherein in (b), the catalyst obtained from (a) is washed in batch mode with a liquid aqueous system which contains at least 99.9 weight-% water, more preferably at least 99.99 weight-% water, more preferably at least 99.999 weight-% water, based on the total weight of the liquid aqueous system, at a pressure in the range of from 0.8 to 1.5 bar, preferably from 1.0 to 1.4 bar, and a temperature in the range of from 40 to 90° C., preferably from 60 to 80° C., wherein the washing in batch mode is carried out outside the reactor according to (ii).

Preferably, the washing according to (b) is performed until the potassium content of the liquid aqueous system after having been contacted with the catalyst is at most 1000 weight-ppm, preferably at most 250 weight-ppm, more preferably at most 25 weight-ppm.

Preferably, the washing according to (b) is performed until the potassium content of the liquid aqueous system after having been contacted with the catalyst relative to the potassium content of the liquid aqueous system before having been contacted with the catalyst is at most 333:1, preferably at most 100:1, more preferably at most 10:1, more preferably 1.2:1.

Generally, if deionized water is used as the liquid aqueous system, it is preferred to subject the catalyst to washing according to (b) until the conductivity of the liquid aqueous system after having been contacted with the catalyst comprising a titanium containing zeolite as catalytically active material is at most 500 microSiemens, preferably at most 400 microSiemens, more preferably at most 300 microSiemens.

Step (c)

After the washing according to (b), the catalyst comprising a titanium containing zeolite obtained can be optionally dried in a step (c) in a gas stream comprising an inert gas at a temperature of less than 300° C.

Preferably, the temperature is in the range of from 20 to 200° C., preferably from 25 to 100° C., more preferably from 30 to 50° C.

Therefore, the present invention preferably relates to the process as described above, wherein in (c), the drying is carried out, preferably at a temperature in the range of from 25 to 100° C., preferably from 30 to 50° C. Further, the present invention preferably relates to the process as described above, wherein wherein in (b), the catalyst obtained from (a) is washed with a liquid aqueous system which contains at least 99.9 weight-% water, more preferably at least 99.99 weight-% water, more preferably at least 99.999 weight-% water, based on the total weight of the liquid aqueous system, at a pressure in the range of from 0.8 to 1.5 bar, preferably from 1.0 to 1.4 bar, and a temperature in the range of from 40 to 90° C., preferably from 60 to 80° C., and wherein in (c), the catalyst obtained from (b) is dried in a gas stream comprising an inert gas at a temperature in the range of from 25 to 100° C., preferably from 30 to 50° C.

The duration of the drying in (c) is dependent on the amount of catalyst comprising a titanium containing zeolite to be dried in the gas stream comprising an inert gas at elevated temperatures. It is conceivable that large amounts of catalyst comprising a titanium containing zeolite require a longer period of time compared with a small amount of catalyst comprising a titanium containing zeolite. It is preferred that the drying in (c) is performed for a period of time in the range of from 5 to 350 hours, preferably from 10 to 250 hours, more preferably for 12 to 100 hours.

The weight hourly space velocity (WHSV) of the gas stream comprising a inert gas in (c) is not subject to specific restrictions and is typically in the range of from 100 to 2000 h$^{-1}$, preferably from 500 to 1500 h$^{-1}$, more preferably from 500 to 1000 h$^{-1}$. The weight hourly space velocity in (c) is defined by the mass flow rate of the gas stream comprising an inert gas divided by the mass of the catalyst comprising a titanium containing zeolite in the reactor.

Preferably, at least 90 volume-%, preferably at least 95 volume-%, more preferably at least 99 volume-% of the gas stream comprising an inert gas according to (c) consist of at least one inert gas. Preferably, the at least one inert gas is selected from the group consisting of nitrogen, helium, argon, and a mixture of two or more three thereof. Preferably, at least 90 volume-%, preferably at least 95 volume-%, more preferably at least 99 volume-%, more preferably at least 99.9 volume-% of the gas stream comprising an inert gas according to (c) consist of nitrogen, preferably of technical nitrogen.

Therefore, the present invention preferably relates to the process as described above, wherein in (c), the drying is carried out, preferably at a temperature in the range of from 25 to 100° C., preferably from 30 to 50° C. Further, the present invention preferably relates to the process as described above, wherein wherein in (b), the catalyst obtained from (a) is washed with a liquid aqueous system which contains at least 99.9 weight-% water, more preferably at least 99.99 weight-% water, more preferably at least 99.999 weight-% water, based on the total weight of the liquid aqueous system, at a pressure in the range of from 0.8 to 1.5 bar, preferably from 1.0 to 1.4 bar, and a temperature in the range of from 40 to 90° C., preferably from 60 to 80° C., and wherein in (c), the catalyst obtained from (b) is dried in a gas stream comprising an inert gas at a temperature in the range of from 25 to 100° C., preferably from 30 to 50° C. wherein at least 99 volume-%, preferably at least 99.9 volume-% of the gas stream consist of nitrogen, preferably technical nitrogen.

For satisfying results, it is preferable to perform the drying according to (c) until the content of water in the gas stream comprising an inert gas after having been contacted with the catalyst comprising a titanium containing zeolite is similar to the water content of the gas stream comprising an inert gas before having been contacted with the catalyst. Preferably, the drying in (c) is performed until the water content of the gas stream comprising an inert gas after having been contacted with the catalyst relative to the water content of the gas stream comprising an inert gas before having been contacted with the catalyst is at most 1.10:1, preferably at most 1.08:1, more preferably at most 1.05:1, more preferably at most 1.03:1.

In the alternative, the drying in (c) may be preferably performed until the volume fraction of water in the gas stream comprising an inert gas after having been contacted with the catalyst comprising a titanium containing zeolite is at most 500 ppmV, preferably at most 400 ppmV, preferably at most 300 ppmV, more preferably at most 250 ppmV relative to the total volume of the gas stream comprising an inert gas.

Step (d)

According to step (d), the catalyst obtained from (b) or (c), preferably from (c), is subjected to calcination in a gas stream comprising oxygen at a temperature of at least 300° C.

Preferably, the calcination according to (d) is performed at a temperature in the range of from 300 to 600° C., preferably from 325 to 575° C., more preferably from 350 to 550° C., more preferably from 375 to 525° C., more preferably from 400 to 500° C.

Therefore, the present invention preferably relates to the process as described above, wherein in (c), the drying is carried out, preferably at a temperature in the range of from 25 to 100° C., preferably from 30 to 50° C. Further, the present invention preferably relates to the process as described above, wherein wherein in (b), the catalyst obtained from (a) is washed with a liquid aqueous system which contains at least 99.9 weight-% water, more preferably at least 99.99 weight-% water, more preferably at least 99.999 weight-% water, based on the total weight of the liquid aqueous system, at a pressure in the range of from 0.8 to 1.5 bar, preferably from 1.0 to 1.4 bar, and a temperature in the range of from 40 to 90° C., preferably from 60 to 80° C., wherein in (c), the catalyst obtained from (b) is dried in a gas stream comprising an inert gas at a temperature in the range of from 25 to 100° C., preferably from 30 to 50° C., and wherein in (d), the catalyst obtained from (c) is calcined in a gas stream comprising oxygen at a temperature in the range of from 375 to 525° C., preferably from 400 to 500° C.

Preferably, the gas stream comprising oxygen employed in (d) has an oxygen content of at least 1 volume-% such as at least 5 volume-%, at least 10 volume-%, at least 15 volume-%, or at least 20 volume-%. More preferably, the gas stream comprising oxygen employed in (d) has an oxygen content in the range of from 1 to 50 volume-%, more preferably from 3 to 40 volume-%, more preferably from 5 to 30 volume-%. If the gas stream comprising oxygen employed in (d) has an oxygen content of less than 100 volume-%, the gas stream mays contain one or more additional gases such as nitrogen, argon, helium, carbon dioxide, water steam, or a mixture of two or more thereof. More preferably, the gas stream comprising oxygen employed for the calcination of the catalyst comprising a titanium containing zeolite in (d) is air or lean air.

Therefore, the present invention preferably relates to the process as described above, wherein in (c), the drying is carried out, preferably at a temperature in the range of from 25 to 100° C., preferably from 30 to 50° C. Further, the present invention preferably relates to the process as described above, wherein wherein in (b), the catalyst obtained from (a) is washed with a liquid aqueous system which contains at least 99.9 weight-% water, more preferably at least 99.99 weight-% water, more preferably at least 99.999 weight-% water, based on the total weight of the liquid aqueous system, at a pressure in the range of from 0.8 to 1.5 bar, preferably from 1.0 to 1.4 bar, and a temperature in the range of from 40 to 90° C., preferably from 60 to 80° C., wherein in (c), the catalyst obtained from (b) is dried in a gas stream comprising an inert gas at a temperature in the range of from 25 to 100° C., preferably from 30 to 50° C., and wherein in (d), the catalyst obtained from (c) is calcined in a gas stream comprising oxygen at a temperature in the range of from 375 to 525° C., preferably from 400 to 500° C., wherein the gas stream comprising oxygen employed in (d) contains oxygen in the range of from 3 to 40 volume-%, preferably from 5 to 50 volume-%.

It is preferred that the weight hourly space velocity (WHSV) of the gas stream comprising oxygen in (d) is in the range of from 100 to 2000 h$^{-1}$, preferably from 500 to 1500 h$^{-1}$, more preferably from 500 to 1000 h$^{-1}$. The weight hourly space velocity in (d) is defined by the mass flow rate of the gas stream comprising oxygen divided by the mass of the catalyst comprising a titanium containing zeolite in the reactor Preferably according to (d), the catalyst, obtained from (c) or (d), preferably from (c), is heated to the calcination temperature at a rate in the range of from 0.5 to 5 K/min, preferably from 1 to 4 K/min, more preferably from 2 to 3 K/min.

Preferably the calcination in (d) is performed for a period of time in the range of from 1 to 15 hours, more preferably from 2 to 10 hours, more preferably from 3 to 7 hours.

The drying according to (c) as well as the calcination according to (d) can be carried out either in the reactor according to (ii) or outside the reactor according to (ii). If the washing according to (b) is carried out in the reactor according to (ii), it may be advantageous to perform the drying according to (c), if carried out, also in the reactor according to (ii). Regarding the calcination according to (d), it may advantageous to perform it in the reactor according to (ii) if the washing according to (b) and the drying according to (c), if carried out, are also performed in the reactor according to (ii), possibly depending on the material and the layout of the reactor.

According to the present invention, the steps (b) to (d) can be repeated at least once. Therefore, after the calcination according to (d), the calcined catalyst can be subjected to (b) again for another sequences of steps (b), optionally (c), and (d). In a given cycle, the respective conditions of the steps can be changed compared to another cycle. Therefore, for example, in a given sequence (b) to (d), drying according to (c) is carried out whereas in another sequence (b) to (d), said drying according to (c) is not carried out. According to the present invention, the sequence of steps (b) to (d) can be repeated 1 to 5 times such as once, twice, three times, four times, of five times, at the same or different conditions in the respective steps (b) to (d). Due to the mild regeneration conditions according to the present invention, it was found that even repeating the sequence of steps (b) to (d) several times does not have a negative impact on the zeolitic structure of the catalyst, and such a repeating may lead to a very effective removal of potassium from the catalyst.

According to the present invention, it is preferred that in the course of a sequence (a) to (d), the spent catalyst is washed with the liquid aqueous system according to (b) wherein this washing in step (b) is the only treatment with a liquid system. Compared to WO-A 2007/013739, there is no such combination of a pretreatment step and a subsequent treatment with another liquid mixture. In particular, according to the preferred process of the present invention, the liquid aqueous system employed in step (b) essentially consists of water, and compared with the process of WO-A 2007/013739, the water treatment as sole treatment with a liquid mixture is an extremely milder regeneration than a treatment with hydrogen peroxide.

Therefore, the present invention relates to the process as described above, wherein the washing according to (b) is the only treatment with a liquid system during the regeneration process comprising (a), (b), optionally (c) and (d).

Step (i)

According to the present invention, the spent catalyst comprising a titanium containing zeolite to be subjected to regeneration steps (a) to (d) is obtained by a process for the preparation of an olefin oxide, comprising:
(i) providing a mixture comprising an organic solvent, an olefin, an epoxidation agent and an at least partially dissolved potassium comprising salt;
(ii) subjecting the mixture provided in (i) in a reactor to epoxidation conditions in the presence of the catalyst, obtaining a mixture comprising the organic solvent and the olefin oxide, and obtaining the catalyst having a potassium salt deposited thereon.

Organic solvents to be employed in (i) are in principle all solvents known for this purpose. Preference is given to using organic solvents such as alcohols, nitriles, and mixtures thereof, optionally also water. It is particularly preferred that the organic solvent is selected from the group consisting of methanol and acetonitrile.

The amounts of organic solvent used can be varied within wide limits. Possible amounts of organic solvent used are from 5 to 25 g of organic solvent per gram of epoxidation agent used. For example, the organic solvent is used in an amount of form 8 to 16 g of organic solvent per gram of epoxidation agent used, or from 10 to 14 g of organic solvent per gram of epoxidation agent used.

The olefin employed in (i) is preferably selected from the group consisting of ethane, propene, 1-butene, 2-butene, isobutene, butadiene, pendenes, piperylene, hexenes, hexadienes, heptenes, octenes, diisobutene, trimethylpentene, nonenes, dodecene, tridecene, tetradecene to eiconsenes, tripropene, tetrapropene, polybutadienes, polyisobutenen, isoprenes, terpenes, geraniol, linalool, linalyl acetate, methylene cyclopropane, cyclopentene, cyclohexene, norbornene, cycloheptene, vinylcyclohexane, vinyloxirane, vinylcyclohexene, styrene, cyclooctene, cyclooctadiene, vinylnorbornene, indene, tetrahydroindene, methylstyrene, dicyclopentadiene, divinylbenzene, cyclododecene, cyclododecatriene, stilbene, dipheylbutadiene, vitamin A, beta-carotene, vinylidene fluoride, allyl halides, crotyl chloride, methallyl chloride, dichlorbutene, allyl alcohol, methallyl alcohol, butenols, butenediols, cyclopentenediols, pentenols, octadienols, tridecenols, unsaturated steroids, ethoxyethene, isoeugenol, anethol, unsaturated carbocyclic acids such as acrylic acid, methacrylic acid, crotonic acid, maleic acid, vinylacetic acid, unsaturated fatty acids such as oleic acid, linoleic acid, palmitic acid, naturally occurring fats and oils, and mixtures thereof. It is particularly preferred that the olefin is propene.

It is preferred that the epoxidation agent employed in (i) is hydrogen peroxide. It is further preferred that the hydrogen peroxide is an aqueous hydrogen peroxide solution, wherein the solution comprises preferably 30 to 50 weight-% hydrogen peroxide relative to the total amount of water. It is also possible that the hydrogen peroxide is formed in situ in the reaction mixture from hydrogen and oxygen in the presence of a suitable catalyst or catalyst system, for example in the presence of a titanium containing zeolite additionally containing one or more noble metals, or a titanium containing zeolite and an additional catalyst containing one or more noble metals, for example supported on a suitable support such as charcoal or a suitable inorganic oxide or mixture of inorganic oxides.

For the preparation of the hydrogen peroxide employed in (i) the anthraquinone process may be used. This process is based on the catalytic hydrogenation of an anthraquinone compound to form the corresponding anthrahydroqhinone compound, subsequent reaction of this with oxygen to form hydrogen peroxide and subsequent extraction of the hydrogen peroxide formed. The cycle is completed by rehydrogenation of the anthraquinone compound which has been formed again in the oxidation. A review of the antraquinone process is given in "Ullmann's Encyclopedia of Industrial Chemistry", $5^{th}$ edition, volume 13, pages 447 to 456.

It is in the alternative conceivable to obtain hydrogen peroxide by anodic oxidation of sulfuric acid with simultaneous evolution of hydrogen at the cathode to produce peroxodisulfuric acid. Hydrolysis of the peroxodisulfuric acid forms firstly peroxosulfuric acid and then hydrogen peroxide and sulfuric acid, which is thus recovered.

In a further alternative, hydrogen peroxide may be prepared directly from the elements hydrogen and oxygen.

Therefore, the spent catalyst comprising a titanium containing zeolite to be subjected to regeneration steps (a) to (d) is preferably obtained by a process for the preparation of propylene oxide, comprising:
(i) providing a mixture comprising an organic solvent, propene, hydrogen peroxide and an at least partially dissolved potassium comprising salt, wherein the organic solvent is selected from the group consisting of methanol and acetonitrile;
(ii) subjecting the mixture provided in (i) in a reactor to epoxidation conditions in the presence of the catalyst, obtaining a mixture comprising the organic solvent and the propylene oxide, and obtaining the catalyst having a potassium salt deposited thereon.

The Potassium Salt

Regarding the chemical nature of the at least one potassium salt is concerned, no specific restrictions exist. Preferably, the at least one potassium salt is selected from the group consisting of at least one inorganic potassium salt, at least one organic potassium salt, and combinations of at least one inorganic potassium salt and at least one organic potassium salt.

Preferred inorganic potassium comprising salts include, but are not restricted to, potassium halides such as potassium chloride or potassium bromide, potassium nitrate, potassium sulfate, potassium hydrogen sulfate, potassium hydroxide, potassium perchlorate, potassium salts comprising phosphorus such as potassium dihydrogen phosphate or dipotassium hydrogen phosphate or potassium phosphate or potassium pyrophosphates such as monobasic potassium pyrophosphate or dibasic potassium pyrophosphate or tribasic potassium pyrophosphate or tetrabasic potassium pyrophosphate, or potassium etidronates such as monobasic potassium etidronate or dibasic potassium etidronate or tribasic potassium etidronate or tetrabasic potassium etidronate, potassium cyanate, potassium oxides such as potassium oxide ($K_2O$) or potassium superoxide ($KO_2$) or potassium peroxide ($K_2O_2$).

Preferred organic potassium comprising salts include, but are not restricted to, potassium carbonate ($K_2CO_3$), potassium hydrogen carbonate, potassium salts of aliphatic saturated carboxylic acids such as monocarboxylic acids preferably having from 1 to 6, more preferably from 1 to 5, more preferably from 1 to 4, more preferably from 1 to 3 carbon atoms such as formic acid, acetic acid, propionic acid, dicarboxylic acids preferably having from 2 to 6, more preferably from 2 to 4 carbon atoms such as oxalic acid, malonic acid, succinic acid, artaric acid, tricarboxylic acids preferably having from 6 to 10 carbon atoms such as citric acid or isocitric acid or propane-1,2,3-tricarboxylic acid, or tetracarboxylic acids. Preferably, the organic potassium salt is selected from the group consisting of potassium salts of aliphatic saturated monocarboxylic acids preferably having 1, 2, 3, 4, 5 or 6 carbon atoms, potassium carbonate, and potassium hydrogen carbonate. More preferably, the organic potassium salt is selected from the group consisting of potassium formate, potassium acetate, potassium propionate, potassium carbonate, and potassium hydrogen carbonate. More preferably, the organic potassium salt is selected from the group consisting of potassium formate, potassium acetate, potassium carbonate, and potassium hydrogen carbonate.

Therefore, the potassium comprising salt is preferably selected from the group consisting of at least one inorganic potassium salt selected from the group consisting of potassium hydroxide, potassium halides, potassium nitrate, potassium sulfate, potassium hydrogen sulfate, potassium perchlorate, potassium dihydrogen phosphate or dipotassium hydrogen phosphate or potassium phosphate or potassium pyrophosphates such as monobasic potassium pyrophosphate or dibasic potassium pyrophosphate or tribasic potassium pyrophosphate or tetrabasic potassium pyrophosphate, or potassium etidronates such as monobasic potassium etidronate or dibasic potassium etidronate or tribasic potassium etidronate or tetrabasic potassium etidronate, at least one organic potassium salt selected from the group consisting of potassium salts of aliphatic saturated monocarboxylic acids preferably having 1, 2, 3, 4, 5 or 6 carbon atoms, potassium carbonate, and potassium hydrogen carbonate, and a combination of at least one of the at least one inorganic potassium salts and at least one of the at least one organic potassium salts.

More preferably, the potassium comprising salt is selected from the group consisting of at least one inorganic potassium salt selected from the group consisting of potassium dihydrogen phosphate or dipotassium hydrogen phosphate or potassium phosphate potassium hydroxide, potassium halides, potassium nitrate, potassium sulfate, potassium hydrogen sulfate, potassium perchlorate, at least one organic potassium salt selected from the group consisting of potassium formate, potassium acetate, potassium propionate, potassium carbonate, and potassium hydrogen carbonate, and a combination of at least one of the at least one inorganic potassium salts and at least one of the at least one organic potassium salts.

Especially preferably, the potassium comprising salt according to (i) is potassium dihydrogen phosphate, dipotassium hydrogen phosphate, or potassium formate. Therefore, if according to (i), one single potassium salt is employed, the potassium comprising salt is most preferably potassium dihydrogen phosphate, dipotassium hydrogen phosphate, or potassium formate. If according to (i) two or more potassium comprising salts are employed, one potassium salt is potassium dihydrogen phosphate, dipotassium hydrogen phosphate, or potassium formate.

Therefore, the spent catalyst comprising a titanium containing zeolite to be subjected to regeneration steps (a) to (d) is preferably obtained by a process for the preparation of propylene oxide, comprising:
(i) providing a mixture comprising an organic solvent, propene, hydrogen peroxide and an at least partially dissolved potassium comprising salt, wherein the organic solvent is selected from the group consisting of methanol and acetonitrile and wherein the potassium comprising salt is selected from the group consisting of dihydrogen phosphate, dipotassium hydrogen phosphate, potassium formate, and a mixture of two or more thereof;
(ii) subjecting the mixture provided in (i) in a reactor to epoxidation conditions in the presence of the catalyst, obtaining a mixture comprising the organic solvent and the propylene oxide, and obtaining the catalyst having a potassium salt deposited thereon.

According to (i), a mixture is provided comprising the potassium comprising salt. Regarding the concentration of the potassium comprising salt in the liquid feed stream, no specific restrictions exist. Preferably, the concentration of the potassium comprising salt in the mixture provided in (i) is at least 10%, preferably in the range of from 10 to 100%, preferably from 20 to 100%, more preferably from 30 to 100%, more preferably from 40 to 100% of the solubility limit of the potassium comprising salt in the liquid feed stream provided in (i). The term "solubility limit of the at least one potassium salt in the liquid feed stream" as used in the context of the present invention relates to the saturation concentration of the potassium comprising salt in the liquid feed stream, where by adding more of the potassium comprising salt, the concentration of the potassium comprising salt as solute in the mixture does not increase and the potassium comprising salt would begin to precipitate. The solubility limit of the potassium comprising salt in the mixture will depend on the composition of the mixture and the conditions such as the temperature at which, and the pressure under which the mixture is provided in (i). Determining the solubility limit of the potassium comprising salt in the mixture is an easy and straight-forward task for the skilled person knowing said conditions and said composition of a given mixture. A simple procedure to evaluate whether the amount of the potassium comprising salt being added is above the solubility limit is passing the mixture before subjecting to epoxidation conditions in (ii) through a filter and measure the pressure drop across the filter. If the pressure drop across the filter increases with time on stream and the potassium comprising salt is found on the filter when it is taken offline, the amount of the potassium comprising salt being added is already above the solubility limit.

Preferably in (i), the molar ratio of potassium comprised in the potassium comprising salt relative to the epoxidation agent, preferably hydrogen peroxide, comprised in the mixture is in the range of from $10 \times 10^{-6}:1$ to $1500 \times 10^{-6}:1$, preferably from $20 \times 10^{-6}:1$ to $1300 \times 10^{-6}:1$, more preferably from $30 \times 10^{-6}:1$ to $1000 \times 10^{-6}1$. The molar amount of the potassium comprised in the potassium comprising salt relates to the total molar amount of potassium comprised in all potassium comprising salts employed in (i), if two or more potassium comprising salts are employed.

Further preferably in (i), the molar ratio of potassium relative to the epoxidation agent, preferably hydrogen peroxide, in the mixture is in the range of from $10 \times 10^{-6}:1$ to $1500 \times 10^{-6}:1$, preferably from $20 \times 10^{-6}:1$ to $1300 \times 10^{-6}:1$, more preferably from $30 \times 10^{-6}:1$ to $1000 \times 10^{-6}1$.

Therefore, the spent catalyst comprising a titanium containing zeolite to be subjected to regeneration steps (a) to (d) is preferably obtained by a process for the preparation of propylene oxide, comprising:
(i) providing a mixture comprising an organic solvent, propene, hydrogen peroxide and an at least partially dissolved potassium comprising salt, wherein the organic solvent is selected from the group consisting of methanol and acetonitrile and, wherein the potassium comprising salt is selected from the group consisting of dihydrogen phosphate, dipotassium hydrogen phosphate, potassium formate, and a mixture of two or more thereof;
(ii) subjecting the mixture provided in (i) in a reactor to epoxidation conditions in the presence of the catalyst, obtaining a mixture comprising the organic solvent and the propylene oxide, and obtaining the catalyst having a potassium salt deposited thereon,
wherein the mixture according to (i) contains the potassium comprising salt with a molar ratio of potassium comprised in the potassium comprising salt relative to hydrogen peroxide in the range of from $10 \times 10^{-6}:1$ to $1500 \times 10^{-6}:1$, preferably from $20 \times 10^{-6}:1$ to $1300 \times 10^{-6}:1$, more preferably from $30 \times 10^{-6}:1$ to $1000 \times 10^{-6}:1$.

Preferably, the process for the preparation of an olefin oxide according to the present invention is a continuous process. Therefore, the spent catalyst comprising a titanium containing zeolite to be subjected to regeneration steps (a) to (d) is preferably obtained by a process for the preparation of propylene oxide, comprising:
(i) providing a liquid feed stream comprising an organic solvent, an olefin, an epoxidation agent and an at least partially dissolved potassium comprising salt;
(ii) passing the feed stream provided in (i) into an epoxidation reactor comprising a catalyst comprising a titanium containing zeolite as catalytically active material, and subjecting the feed stream to epoxidation reaction conditions in the epoxidation reactor, obtaining a reaction mixture comprising the organic solvent and the olefin oxide, and obtaining the catalyst having a potassium salt deposited thereon.

More preferably, the spent catalyst comprising a titanium containing zeolite to be subjected to regeneration steps (a) to (d) is preferably obtained by a process for the preparation of propylene oxide, comprising:
(i) providing a liquid feed stream comprising an organic solvent, propene, hydrogen peroxide and an at least partially dissolved potassium comprising salt, wherein the organic solvent is selected from the group consisting of methanol and acetonitrile and, wherein the potassium comprising salt is selected from the group consisting of dihydrogen phosphate, dipotassium hydrogen phosphate, potassium formate, and a mixture of two or more thereof;
(ii) passing the feed stream provided in (i) into an epoxidation reactor comprising a catalyst comprising a titanium containing zeolite as catalytically active material, and subjecting the feed stream to epoxidation reaction conditions in the epoxidation reactor, obtaining a mixture comprising the organic solvent and the propylene oxide, and obtaining the catalyst having a potassium salt deposited thereon,
wherein the mixture according to (i) contains the potassium comprising salt with a molar ratio of potassium comprised in the potassium comprising salt relative to hydrogen peroxide in the range of from $10 \times 10^{-6}:1$ to $1500 \times 10^{-6}:1$, preferably from $20 \times 10^{-6}:1$ to $1300 \times 10^{-6}:1$, more preferably from $30 \times 10^{-6}:1$ to $1000 \times 10^{-6}:1$.

Preferably, the mixture, preferably the liquid feed stream provided in (i) is free of ammonium dihydrogen phosphate. More preferably, the mixture, preferably the liquid feed stream provided in (i), is free of ammonium phosphate, ammonium hydrogen phosphate and ammonium dihydrogen phosphate. More preferably, the mixture, preferably the liquid feed stream provided in (i) is free of ammonium carbonate, ammonium hydrogen carbonate, ammonium dihydrogen phosphate, ammonium hydrogen phosphate, ammonium phosphate, ammonium hydrogen pyrophosphate, ammonium pyrophosphate, ammonium chloride, ammonium nitrate, and ammonium acetate. More preferably, the mixture, preferably the liquid feed stream provided in (i), is free of an ammonium salt. The term "free of" as used in this context of the present invention relates to a concentration of a respective compound of at most 2 weight-ppm, preferably at most 1 weight-ppm, based on the total weight of the mixture, preferably the liquid feed stream.

Preferably, the mixture, preferably the liquid feed stream provided in (i), contains sodium in a molar ratio of sodium relative to epoxidation agent, preferably hydrogen peroxide in the range of from $1 \times 10^{-6}:1$ to $250 \times 10^{-6}:1$, preferably from $5 \times 10^{-6}:1$ to $50 \times 10^{-6}:1$. Preferably, the mixture, preferably the liquid feed stream provided in (i), does not comprise dissolved sodium dihydrogen phosphate ($NaH_2PO_4$), more preferably neither dissolved sodium dihydrogen phosphate nor dissolved disodium hydrogen phosphate ($Na_2HPO_4$), more preferably neither dissolved sodium dihydrogen phosphate nor dissolved disodium hydrogen phosphate nor dissolved sodium phosphate ($Na_3PO_4$).

Liquid Feed Stream

Generally, the liquid feed stream can be provided in (i) according to any conceivable method. Preferably, the liquid feed stream is provided in (i) by combining at least four individual streams wherein a first stream comprises the epoxidation agent, preferably hydrogen peroxide, a second stream comprises the olefin, preferably propene and optionally propane, a third stream comprises the organic solvent, preferably selected from the group consisting of methanol and acetonitrile, and optionally water, and a fourth stream comprises the potassium comprising salt.

These at least four individual stream can be combined in every suitably order. Preferably, the stream comprising the potassium comprising salt is combined with the stream comprising the epoxidation agent, and the resulting combined stream is combined with a stream which results from combining the stream comprising the organic solvent and the stream comprising the olefin. The thus obtained stream is the liquid stream provided in (i).

Preferably, the stream comprising propene additionally comprises propane wherein preferably at least 98 weight-%, more preferably at least 99 weight-%, more preferably at least 99.5 weight-%, more preferably at least 99.9 weight-% of the stream consist of propene and propane. Preferably, the weight ratio of propene relative to propane in the stream is at least 7:3. For example, commercially available propene can be employed which may be either a polymer grade propene or a chemical grade propene. Typically, polymer grade propene has a propene content in the range of from 99 to 99.8 weight-% and a propane content in the range of from 0.2 to 1 weight-%. Chemical grade propene typically has a propene content in the range of from 92 to 98 weight-% and a propane content in the range of from 2 to 8 weight-%. Preferably, a stream is employed having a propene content in the range of from 99 to 99.8 weight-% and a propane content in the range of from 0.2 to 1 weight-%.

Preferably, the stream comprising olefin, preferably propene and optionally propane is free of potassium cations ($K^+$) and free of phosphorus (P) in the form of anions of at least one phosphorus oxyacid. The term "free of potassium cations ($K^+$)" as used in this context of the present invention refers to a stream comprising olefin, containing potassium cations ($K^+$) in an amount of less than 1 weight-ppm, preferably less than 0.1 weight-ppm, based on the total weight of the stream. The term "free of phosphorus (P) in the form of anions of at least one phosphorus oxy-acid" as used in this context of the present invention refers to a stream comprising the olefin, containing phosphorus (P) in the form of anions of at least one phosphorus oxyacid in an amount of less than 1 weight-ppm, preferably less than 0.1 weight-ppm, based on the total weight of the stream.

The stream comprising hydrogen peroxide can be prepared according to every conceivable method. It is conceivable to obtain the stream comprising hydrogen peroxide by converting sulphuric acid into peroxodisulphuric acid by anodic oxidation with simultaneous evolution of hydrogen at the cathode. Hydrolysis of the peroxodisulphuric acid then leads via peroxomonosulphuric acid to hydrogen peroxide and sulphuric acid which is thus obtained back. The preparation of hydrogen peroxide from the elements is also conceivable. Depending on the specific preparation method, the stream comprising hydrogen peroxide can be, for example, an aqueous or an aqueous/methanolic hydrogen peroxide stream, preferably an aqueous hydrogen peroxide stream. In case an aqueous hydrogen peroxide feed is employed, the content of the stream with respect to hydrogen peroxide is usually in the range of from 3 to 85 weight-%, preferably from 25 to 75 weight-%, more preferably from 30 to 50 weight-%, such as from 30 to 40 weight-% or from 35 to 45 weight-% of from 40 to 50 weight-%. Preferably, at least 25 weight-%, more preferably at least 30 weight-%, more preferably at least 35 weight-% of the stream comprising hydrogen peroxide consist of water and hydrogen peroxide. Preferred ranges are from 30 to 80 weight% or from 35 to 75 weight-% or from 40 to 70 weight-%.

According to the present, it is preferred to employ a stream comprising hydrogen peroxide which is obtained as crude hydrogen peroxide solution by extraction of a mixture which results from a process known as anthraquinone process by means of which virtually the entire world production of hydrogen peroxide is produced (see, e.g., Ullmann's Encyclopedia of Industrial Chemistry, $5^{th}$ edition, volume A 13 (1989) pages 443-466) wherein a solution of an anthraquinone is used containing an alkyl group preferably having of from 2 to 10 carbon atoms, more preferably at least 5 carbon atoms such as 5 carbon atoms or 6 carbon atoms and where the solvent used usually consists of a mixture of two different solvents. This solution of the anthraquinone is usually referred to as the working solution. In this process, the hydrogen peroxide formed in the course of the anthraquinone process is generally separated by extraction from the respective working solution after a hydrogenation/re-oxidation cycle. Said extraction can be performed preferably with essentially pure water, and the crude aqueous hydrogen peroxide solution is obtained. While it is generally possible to further purify the thus obtained crude aqueous hydrogen peroxide solution by distillation, it is preferred, according to the present invention, to use such crude aqueous hydrogen peroxide solution which has not been subjected to purification by distillation. Further, it is generally possible to subject the crude aqueous hydrogen peroxide solution to a further extraction stage wherein a suitable extracting agent, preferably an organic solvent is used. More preferably, the organic solvent used for this further extraction stage is the same solvent which is used in the anthraquinone process. Preferably the extraction is performed using just one of the solvents in the working solution and most preferably using just the most nonpolar solvent of the working solution. In case the crude aqueous hydrogen peroxide solution is subjected to such further extraction stage, a so-called crude washed hydrogen peroxide solution is obtained. According to a preferred embodiment of the present invention, the crude washed hydrogen peroxide solution is used as hydrogen peroxide feed. The production of a crude solution is described, for example, in European patent application EP 1 122 249 A1. As to the term "essentially pure water", reference is made to paragraph 10, page 3 of EP 1 122 249 A1 which is incorporated by reference.

In order to provide a sufficient stability of the hydrogen peroxide during extraction with water, preferably essentially pure water, suitable stabilizing agents are usually added to the water, preferably the essentially pure water used. In particular, strong inorganic acids and/or chelating agents are to be mentioned. According to preferred extraction processes, small amounts of nitrates and/or phosphates and pyrophosphates, respectively, are added as stabilizing agents, either as acids or as sodium salts. These stabilizing agents are usually added in amounts so that the crude aqueous hydrogen peroxide solution contains from 50 to 400 weight-ppm sodium cations, from 100 to 700 weight-ppm phosphorus calculated as phosphate ($PO_4^{3-}$), and from 50 to 400 weight-ppm nitrate anions, in each case calculated with respect to hydrogen peroxide contained in the crude aqueous hydrogen peroxide solution. Preferred ranges are, for example, from 50 to 200 weight-ppm or from 50 to 100 weight-ppm of sodium cations, from 100 to 500 weight-ppm or from 100 to 300 weight-ppm of phosphorus, and 50 to 200 weight-ppm or 50 to 100 weight-ppm of nitrate. Further, it is conceivable that other stabilizing agents such as stannites like sodium stannite ($Na_2SnO_2$) and/or organic phosphonic acids, in particular organic diphosphonic acids like etidronic acid are used. Preferably, the aqueous hydrogen peroxide stream comprises sodium with a molar ratio of sodium relative to hydrogen peroxide in the range of from $1 \times 10^{-6}:1$ to $250 \times 10^{-6}:1$, more preferably from $5 \times 10^{-6}:1$ to $50 \times 10^{-6}:1$.

Generally, the molar ratio of water relative to the organic solvent in the liquid feed stream provided in (i) is not subject to any specific restrictions. Preferably, in particular in case the organic solvent is acetonitrile, the molar ratio of water relative to the organic solvent is at most 1:4, more preferably in the range of from 1:50 to 1:4, preferably from 1:15 to 1:4.1, more preferably from 1:10 to 1:4.2.

Therefore, the spent catalyst comprising a titanium containing zeolite to be subjected to regeneration steps (a) to (d) is preferably obtained by a process for the preparation of propylene oxide, comprising:
(i) providing a liquid feed stream comprising an organic solvent, propene, optionally propane, hydrogen peroxide, water, and an at least partially dissolved potassium comprising salt, wherein the organic solvent is selected from the group consisting of methanol and acetonitrile and, wherein the potassium comprising salt is selected from the group consisting of dihydrogen phosphate, dipotassium hydrogen phosphate, potassium formate, and a mixture of two or more thereof;
(ii) passing the feed stream provided in (i) into an epoxidation reactor comprising a catalyst comprising a titanium containing zeolite as catalytically active material, and subjecting the feed stream to epoxidation reaction conditions in the epoxidation reactor, obtaining a mixture comprising the organic solvent the propylene oxide, water, optionally propene, optionally propane, and obtaining the catalyst having a potassium salt deposited thereon, wherein the mixture according to (i) contains the potassium comprising salt with a molar ratio of potassium comprised in the potassium comprising salt relative to hydrogen peroxide in the range of from $10 \times 10^{-6}:1$ to $1500 \times 10^{-6}:1$, preferably from $20 \times 10^{-6}:1$ to $1300 \times 10^{-6}:1$, more preferably from $30 \times 10^{-6}:1$ to $1000 \times 10^{-6}:1$.

In case acetonitrile is used as solvent, the mixture provided in (i), preferably the liquid feed stream provided in (i), preferably comprises
the acetonitrile in amount of from 60 to 75 weight-%, preferably from 60 to 65 weight-%, based on the total weight of the liquid feed stream;
the hydrogen peroxide in an amount of from 6 to 10 weight-%, preferably from 7 to 9 weight-%, based on the total weight of the liquid feed stream;
the water in a molar ratio of water relative to acetonitrile of at most 1:4, preferably in the range of from 1:50 to 1:4, preferably from 1:15 to 1:4.1, more preferably from 1:10 to 1:4.2;

the propene with a molar ratio of propene relative to hydrogen peroxide comprised in the liquid feed stream in the range of from 1:1 to 1.5:1, preferably from 1.1:1 to 1.4:1; and
optionally the propane with a molar ratio of propane relative to the sum of propene and propane in the range of from 0.0001:1 to 0.15:1, preferably from 0.001:1 to 0.05:1;
wherein at least 95 weight-%, preferably from 95 to 100 weight-%, more preferably from 98 to 100 weight-% of the liquid feed stream provided in (i) consist of propene, hydrogen peroxide, acetonitrile, water, the potassium comprising salt, and optionally propane.

Step (ii)

The mixture provided in (i) is subjected in (ii) in a suitable reactor to suitable epoxidation conditions in the presence of the catalyst comprising a titanium containing zeolite as catalytically active material.

The Catalyst Comprising a Titanium Containing Zeolite as Catalytically Active Material Generally, the titanium containing zeolite used as catalytically active material may have a framework structure type according to the following three-letter codes: ABW, ACO, AEI, AEL, AEN, AET, AFG, AFI, AFN, AFO, AFR, AFS, AFT, AFX, AFY, AHT, ANA, APC, APD, AST, ASV, ATN, ATO, ATS, ATT, ATV, AWO, AWW, BCT, BEA, BEC, BIK, BOG, BPH, BRE, CAN, CAS, CDO, CFI, CGF, CGS, CHA, CHI, CLO, CON, CZP, DAC, DDR, DFO, DFT, DOH, DON, EAB, EDI, EMT, EPI, ERI, ESV, ETR, EUO, FAU, FER, FRA, GIS, GIU, GME, GON, GOO, HEU, IFR, ISV, ITE, ITH, ITW, IWR, IWW, JBW, KFI, LAU, LEV, LIO, LOS, LOV, LTA, LTL, LTN, MAR, MAZ, MEI, MEL, MEP, MER, MMFI, MFS, MON, MOR, MSO, MTF, MTN, MTT, MTW, MWW, NAB, NAT, NEES, NON, NPO, OBW, OFF, OSI, OSO, PAR, PAU, PHI, PON, RHO, RON, RRO, RSN, RTE, RTH, RUT, RWR, RWY, SAO, SAS, SAT, SAV, SBE, SBS, SBT, SFE, SFF, SFG, SFH, SFN SFO, SGT, SOD, SSY, STF, STI, STT, TER, THO, TON, TSC, UEI, UFI, UOZ, USI, UTL, VET, VFI, VNI, VSV, WEI, WEN, YUG, ZON, or a mixed structure of two or more of these framework structures. Regarding the three-letter codes and their definitions, reference is made to the "Atlas of Zeolite Framework Types", $5^{th}$ edition, Elsevier, London, England (2001)."

It is further preferred that the titanium containing zeolite has a an MFI framework structure, an MEL framework structure, an MWW framework structure, an MWW-type framework structure, an ITQ framework structure, a BEA framework structure, a MOR framework structure, or a mixed structure of two or more of these framework structures, preferably an MFI framework structure, an MWW framework structure or an MWW-type framework structure. More preferably, the titanium containing zeolite is a zeolite known as "TS-1" (titanium silicalite-1) or TiMWW.

Preferably, in particular in case the titanium containing zeolite is TiMWW, the titanium containing zeolite comprises at least one element selected from the group consisting of Al, B, Zr, V, Nb, Ta, Cr, Mo, W, Mn, Fe, Co, Ni, Zn, Ga, Ge, In, Sn, Pb, Pd, Pt, Au, preferably from the group consisting of B, Zr, V, Nb, Ta, Cr, Mo, W, Mn, Fe, Co, Ni, Zn, Ga, Ge, In, Sn, Pb, Pd, Pt, Au, more preferably from the group consisting of Zr, V, Nb, Ta, Cr, Mo, W, Mn, Fe, Co, Ni, Zn, Ga, Ge, In, Sn, Pb, Pd, Pt, Au. More preferably, the titanium containing zeolite comprises further Zn.

The term "titanium zeolite of framework structure type MWW" as used in the context of the present invention, also referred to as "TiMWW", relates to a zeolite of framework structure MWW which contains titanium as isomorphous substitution element in the zeolitic framework. Preferably, the zeolitic framework is essentially free of aluminum and essentially consists of silicon, titanium, and oxygen. Preferably, at least 99 weight-%, more preferably at least 99.5 weight-%, more preferably at least 99.9 weight-% of the zeolitic framework consist of silicon, titanium, and oxygen. Optionally, the titanium zeolite of framework structure type MWW may comprise extra-framework titanium which is to be understood as every titanium species which is not part of the MWW zeolitic framework. The preparation of TiMWW catalysts is described, for example, in US 2007043226 A1, in particular in Examples 3 and 5 of US 2007043226 A1.

The titanium content of the titanium zeolite of framework structure type MWW is not subject to any specific restrictions. Preferably, the titanium zeolite of framework structure type MWW comprised in the catalyst in (ii) contains titanium, calculated as elemental titanium, in an amount in the range of from 0.1 to 5 weight-%, more preferably from 0.2 to 4 weight-%, more preferably from 0.5 to 3 weight-%, more preferably from 1 to 2 weight-%, based on the total weight of the titanium zeolite of framework structure type MWW. Therefore, the present invention relates to the process as described above, wherein the titanium zeolite of framework structure type MWW comprised in the catalyst in (ii) contains titanium, calculated as elemental titanium, in an amount in the range of from 0.1 to 5 weight-%, preferably from 1 to 2 weight-%, silicon, based on the total weight of the titanium zeolite of framework structure type MWW.

In addition to the titanium, the titanium zeolite of framework structure type MWW may comprise at least one further element other than titanium, silicon, and oxygen. Generally, it is conceivable that this at least one further element is an isomorphous substitution element which is part of the MWW zeolitic framework structure. Preferably, this at least one further element is not an isomorphous substitution element. Such a further element which is not an isomorphous substitution element can be applied to the zeolite by, for example, a spray process, a wet impregnation process such as an incipient wetness process, or any other suitable process. Preferably, the at least one further element is selected from the group consisting of Al, Zr, V, Nb, Ta, Cr, Mo, W, Mn, Fe, Co, Ni, Zn, Ga, Ge, In, Sn, Pb, and a combination of two or more, preferably from the group consisting of Zr, V, Nb, Ta, Cr, Mo, W, Mn, Fe, Co, Ni, Zn, Ga, Ge, In, Sn, Pb, and a combination of two or more. More preferably, the titanium zeolite of framework structure type MWW contains zinc as further element in addition to titanium, silicon, and oxygen. More preferably, the titanium zeolite of framework structure type MWW contains zinc as the sole further element in addition to titanium, silicon, and oxygen. More preferably, the titanium zeolite of framework structure type MWW contains zinc as the sole further element in addition to titanium, silicon, and oxygen wherein at least 99 weight-%, more preferably at least 99.5 weight-%, more preferably at least 99.9 weight-% of the zeolitic framework structure consist of silicon, titanium, and oxygen. More preferably, in case the titanium zeolite of framework structure type MWW contains zinc as the sole further element, at least 99 weight-%, more preferably at least 99.5 weight-%, more preferably at least 99.9 weight-% of the titanium zeolite of framework structure type MWW consist of zinc, titanium, silicon, and oxygen; this titanium zeolite of framework structure type MWW which contains zinc as the sole further element is also referred to as "ZnTiMWW".

ZnTiMWW Catalyst

The zinc content of the titanium zeolite of framework structure type MWW is not subject to any specific restrictions. Preferably, the titanium zeolite of framework structure type MWW comprised in the catalyst in (ii) contains zinc, calculated as elemental zinc, in an amount in the range of from 0.1 to 5 weight-%, more preferably from 0.2 to 4 weight-%, more preferably from 0.5 to 3 weight-%, more preferably from 1 to 2 weight-%, based on the total weight of the titanium zeolite of framework structure type MWW. Therefore, the present invention relates to the process as described above, wherein the titanium zeolite of framework structure type MWW comprised in the catalyst in (ii) contains zinc, calculated as elemental zinc, in an amount in the range of from 0.1 to 5 weight-%, preferably from 1 to 2 weight-%, based on the total weight of the titanium zeolite of framework structure type MWW.

The catalyst according to (ii), comprising the titanium zeolite of framework structure type MWW, can consist of the titanium zeolite of framework structure type MWW, preferably consist of the TiMWW or the ZnTiMWW as described. In such cases, the catalyst can be the titanium zeolite of framework structure type MWW in the form of the zeolitic powder which can be molded, for example as a granules, a microsphere such as a microsphere obtained from spray drying or by a spray granulation, a shaped body having, for example, the shape of a pellet, a tablet, a cylinder, a wheel, a star, a sphere, and so forth.

Preferably, the catalyst according to (ii), comprising the titanium zeolite of framework structure type MWW, preferably the TiMWW or the ZnTiMWW, is prepared as a molding comprising the titanium zeolite of framework structure type MWW, preferably the TiMWW or the ZnTiMWW, by suitably mixing the titanium zeolite of framework structure type MWW with at least one binder and/or with at least one binder precursor, and optionally at least one pore-forming agent and/or at least one plasticizing agent. The moldings may be shaped in every conceivable geometry such as strands, for example having rectangular, triangular hexagonal, quadratic, oval, or circular cross-section, stars, tablets, spheres, hollow cylinders, and the like. Examples of such binders are metal oxides, such as, for example, $SiO_2$, $Al_2O_3$, $TiO_2$, $ZrO_2$ or MgO or clays or mixtures of two or more of these oxides or mixed oxides of at least two of Si, Al, Ti, Zr, and Mg, with $SiO_2$ being preferred. Pore-forming agent such as mesopore-forming agents include polymeric vinyl compounds, such as polyalkylene oxides like polyethylene oxides, polystyrene, polyacrylates, polymethacrylates, polyolefins, polyamides and polyesters. Pasting agents include organic, in particular hydrophilic polymers, such as carbohydrates like cellulose, cellulose derivatives, such as methyl cellulose, and starch, such as potato starch, wallpaper plaster, polyacrylates, polymethacrylates, polyvinyl alcohol, polyvinyl pyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylene glycol, as pasting agents may be mentioned. Preferably, the catalyst according to (ii), is employed as a molding having the shape of an extrudates, preferably an extrudates having a length of preferably from 1 to 10 mm, more preferably of from 1 to 7 mm, more preferably of from 1 to 5 mm, and a diameter preferably of from 0.1 to 5 mm, more preferably of from 0.2 to 4 mm, more preferably of from 0.5 to 2 mm. In particular as far as the preferred catalyst according to (ii) is concerned comprising the ZnTiMWW, it is preferred to employ this catalyst in the form of a micropowder or in the form of a molding, wherein the molding preferably contains said micropowder.

Said catalyst used according to step (ii) of the present invention in the form of a micropowder, comprising the ZnTiMWW, is preferably characterized by the following features and embodiments, including the combinations of embodiments according to the given dependencies:

1. A micropowder, the particles of which having a Dv10 value of at least 2 micrometer, said micropowder comprising mesopores having an average pore diameter (4V/A) in the range of from 2 to 50 nm as determined by Hg porosimetry according to DIN 66133, and comprising, based on the weight of the micropowder, at least 95 weight-% of a microporous aluminum-free zeolitic material of structure type MWW containing titanium and zinc (ZnTiMWW). The Dv10 value is understood as being determined according to Reference Example 5.1 of the present invention.
2. The micropowder of embodiment 1, having a Dv10 value in the range of from 2 to 5.5 micrometer, preferably from 3 to 5.5 micrometer.
3. The micropowder of embodiment 1 or 2, having a Dv50 value in the range of from 7 to 25 micrometer and optionally a Dv90 value in the range of from 26 to 85 micrometer. The Dv50 and Dv90 values are understood as being determined according to Reference Example 5.1 of the present invention.
4. The micropowder of any of embodiments 1 to 3, wherein the mesopores have an average pore diameter (4V/A) in the range of from 10 to 50 nm, preferably of from 15 to 40 nm, more preferably of from 20 to 30 nm, as determined by Hg porosimetry according to DIN 66133.
5. The micropowder of any of embodiments 1 to 4, additionally comprising macropores having an average pore diameter (4V/A) in the range of from more than 50 nm, said macropores preferably having an average pore diameter in the range of from 0.05 to 3 micrometer, as determined by Hg porosimetry according to DIN 66133.
6. The micropowder of any of embodiments 1 to 5, wherein the micropores of the ZnTiMWW have an average pore diameter in the range of from 1.0 to 1.2 nanometer as determined by nitrogen adsorption according to DIN 66135.
7. The micropowder of any of embodiments 1 to 6, comprising, based on the weight of the micropowder, at least 99 weight-%, preferably at least 99.7 weight-% of the ZnTiMWW.
8. The micropowder of any of embodiments 1 to 7, wherein the ZnTiMWW contains zinc in an amount of from 1.0 to 2.0 weight-%, preferably of from 1.2 to 1.9 weight-%, calculated as Zn and based on the weight of the ZnTiMWW.
9. The micropowder of any of embodiments 1 to 8, wherein the ZnTiMWW contains titanium in an amount of from 1.0 to 2.0 weight-%, preferably of from 1.2 to 1.8 weight-%, calculated as Ti and based on the weight of the ZnTiMWW.
10. The micropowder of any of embodiments 1 to 9, having a crystallinity, as determined by X-ray diffraction (XRD) analysis, of at least (80+/−10) %, preferably of at least (85+/−10) %. The crystallinity is understood as being determined according to Reference Example 5.7 of the present invention.
11. The micropowder of any of embodiments 1 to 10, comprising, based on the total weight of the micropowder and calculated as element, less than 0.001 weight-%, preferably less than 0.0001 weight-% of a noble metal, preferably selected from the group consisting of gold, silver, platinum, palladium, iridium, ruthenium, osmium, and a mixture of two or more thereof, more preferably selected from the group consisting of gold, platinum, gold, and a mixture of two or more thereof.
12. The micropowder of any of embodiments 1 to 11, comprising, based on the total weight of the micropowder and calculated as element, less than 0.1 weight.-%, preferably less than 0.01 weight-% of boron.
13. The micropowder of any of embodiments 1 to 12, having a bulk density of in the range of from 80 to 100 g/ml.
14. The micropowder of any of embodiments 1 to 13, being a spray powder, preferably obtainable or obtained by spray-drying.

Further, said catalyst used according to step (ii) of the present invention in the form of a molding, comprising the ZnTiMWW, is preferably characterized by the following features and embodiments, including the combinations of embodiments according to the given dependencies:

1. A molding, comprising a microporous aluminum-free zeolitic material of structure type MWW containing titanium and zinc (ZnTiMWW), said molding preferably comprising a micropowder comprising, based on the weight of the micropowder, at least 95 weight-% of a microporous aluminum-free zeolitic material of structure type MWW containing titanium and zinc (ZnTiMWW), said molding more preferably comprising the micropowder according to any of the micropowder embodiments 1 to 14 as described hereinabove, the molding preferably further comprising at least one binder, preferably a silica binder.
2. The molding of embodiment 1, comprising mesopores having an average pore diameter in the range of from 4 to 40 nm, preferably from 20 to 30 nm as determined by Hg porosimetry according to DIN 66133.
3. The molding of embodiment 1 or 2, having a crystallinity, as determined by XRD analysis, of at least (55+/−10) %, preferably in the range of from ((55 to 75)+/−10) %. The crystallinity is understood as being determined according to Reference Example 5.7 of the present invention.
4. The molding of any of embodiments 1 to 3, comprising the micropowder in an amount in the range of from 70 to 80 weight-% and the silica binder in an amount of from 30 to 20 weight-%, the micropowder together with the silica binder constituting at least 99 weight-% of the molding, wherein the molding has a concentration of silanol groups with respect to the total number of Si atoms of at most 6%, preferably at most 3%, as determined according to $^{29}$Si MAS NMR. The concentration of the silanol groups is understood as being determined according to Reference Example 5.2 of the present invention.
5. The molding of any of embodiments 1 to 4, being a strand having circular cross-section and a diameter in the range of from 1.5 to 1.7 mm and having a crush strength of at least 5 N, preferably in the range of from 5 to 20 N, more preferably in the range of from 12 to 20 N, the crush strength being determined by crush strength test machine Z2.5/TS1S according to the method as described in Reference Example 5.3 of the present invention.
6. The molding of any of embodiments 1 to 5, the $^{29}$Si-NMR spectrum of said molding comprising six peaks at the following position
peak 1 at −98+/−x ppm,
peak 2 at −104+/−x ppm,
peak 3 at −110+/−x ppm,
peak 4 at −113+/−x ppm,
peak 5 at −115+/−x ppm,
peak 6 at −118+/−x ppm, with x in any of the peaks being 1.5, preferably 1.0, more preferably 0.5,
wherein Q which is defined as $$Q=100*\{[a_1+a_2]/[a_4+a_5+a_6]\}/a_3$$

is at most 2.5, preferably at most 1.6, preferably at most 1.4, with $[a_1+a_2]$ being the sum of the peak areas of peaks 1 and 2, and $[a_4+a_5+a_6]$ being the sum of the peak areas of peaks 4, 5, and 6, and $a_3$ being the peak area of peak 3. These $^{29}$Si-NMR characteristics are understood as being determined according the Reference Example 5.4 of the present invention.
7. The molding of any of embodiments 1 to 6, having a water uptake in the range of from 3 to 8 weight-%, preferably from 4 to 7 weight-%. The water uptake is understood as being determined according to Reference Example 5.5 of the present invention.
8. The molding of any of embodiments 1 to 7, the infrared spectrum of said molding comprising a band in the region of $(3700-3750)+/-20$ cm$^{-1}$ and a band in the region of $(3670-3690)+/-20$ cm$^{-1}$, wherein the intensity ratio of the band in the region of $(3700-3750)+/-20$ cm$^{-1}$ relative to the band in the region of $(3670-3690)+/-20$ cm$^{-1}$ is at most 1.5, preferably at most 1.4. These IR characteristics are understood as being determined according the Reference Example 5.6 of the present invention.

Further, a preferred process for the preparation of said catalyst according to (ii) in the form of a micropowder and/or molding, comprising the ZnTiMWW, is characterized by the following features and embodiments, including the combinations of embodiments according to the given dependencies:
1. A process comprising
   (a) providing a suspension containing a microporous aluminum-free zeolitic material of structure type MWW containing titanium and zinc (ZnTiMWW);
   (b) subjecting the suspension provided in (a) to spray-drying to obtain a micropowder;
   (c) optionally calcining the micropowder obtained in (b),
   wherein the micropowder obtained in (b) or (c), preferably in (c), is preferably the micropowder according to any of said micropowder embodiments 1 to 14 as described above.
2. The process of embodiment 1, wherein the suspension provided in (a) has a solid content in the range of from 5 to 25 weight-%, preferably of from 10 to 20 weight-%, the suspension preferably being an aqueous suspension.
3. The process of embodiment 1 or 2, wherein the ZnTiMWW according to (a) contains zinc in an amount of from 1.0 to 2.0 weight-%, preferably of from 1.2 to 1.9 weight-%, calculated as Zn, and titanium in an amount of from 1.0 to 2.0 weight-%, preferably of from 1.2 to 1.8 weight-%, calculated as Ti and based on the weight of the ZnTiMWW.
4. The process of any of embodiments 1 to 3, wherein in (b), a spray-apparatus, preferably a spray-tower is used for spray-drying the suspension, said apparatus having at least one spray-nozzle, preferably at least one two-component nozzle, said nozzle having a diameter in the range of from 3.5 to 4.5 mm.
5. The process of any of embodiments 1 to 4, wherein in (b), a spray-apparatus, preferably a spray-tower is used for spray-drying the suspension, said apparatus being operated with a nozzle gas having a temperature in the range of from 20 to 50° C., preferably of from 20 to 30° C., and a drying gas having a temperature in the range of from 250 to 350° C., preferably of from 275 to 325° C., said nozzle gas preferably being an inert gas, more preferably technical nitrogen, and said drying gas preferably being an inert gas, more preferably technical nitrogen.
6. The process of any of embodiments 1 to 5, wherein in (c), the micropowder is calcined at a temperature in the range of from 600 to 700° C. for a duration in the range of from 0.5 to 6 h.
7. The process of any of embodiments 1 to 6, further comprising
   (d) shaping the micropowder obtained in (b) or (c) to obtain a molding;
   (e) optionally drying and/or calcining the molding obtained in (d).
8. The process of embodiment 7, wherein the shaping according to (d) comprises
   (aa) mixing the micropowder with a binder or a binder precursor, preferably a silica binder or a silica binder precursor, wherein the weight ratio of the ZnTiMWW contained in the micropowder relative to silica contained in or resulting from the silica binder is in the range of from 3:7 to 1:4, to obtain a mixture;
   (bb) shaping the mixture obtained in (aa) to obtain the molding, said shaping preferably comprising subjecting the mixture obtained in (aa) to extrusion from which preferably strands are obtained having a diameter preferably in the range of from 1.0 to 2.0 mm, more preferably of from 1.5 to 1.7 mm.
9. The process of embodiment 8, wherein in (aa), a carbohydrate and/or water is/are added as pasting agent.
10. The process of embodiment 8 or 9, wherein the mixing in (aa) is carried out for a duration in the range of from 15 to 60 min, preferably of from 30 to 55 min, more preferably of from 40 to 50 min.
11. The process of any of embodiments 7 to 10, wherein in (d), no mesopore-forming agent selected from the group consisting of polyalkylene oxides such as polyethylene oxides, polystyrene, polyacrylates, polymethacrylates, polyolefins, polyamides, and polyesters is added.
12. The process of any of embodiments 7 to 11, wherein in (e), the molding is dried at a temperature in the range of from 100 to 150° C. for a duration in the range of from 10 to 20 h and calcined at a temperature in the range of from 500 to 600° C. for a duration in the range of from 0.5 to 2 h.
13. The process of any of embodiments 7 to 12, further comprising
   (f) subjecting the molding obtained in (d) or (e), preferably in (e), to a water-treatment;
   (g) optionally drying and/or calcining the water-treated molding,
   wherein the molding obtained in (f) or (g), preferably in (g), is preferably the molding according to any of said molding embodiments 1 to 8 as described above.
14. The process of embodiment 13, wherein in (f), the water-treatment comprises treating the molding with liquid water in an autoclave under autogenous pressure at a temperature in the range of from 100 to 200° C., preferably of from 125 bis 175° C., more preferably of from 140 to 150° C. for a period of from 2 to 24 hours, preferably of from 6 to 10 h.
15. The process of embodiment 13 or 14, wherein in (f), the weight ratio of the molding relative to the water is in the range of from 0.02 to 0.08, preferably of from 0.03 to 0.07, more preferably of from 0.04 to 0.06.
16. The process of any of embodiments 13 to 15, wherein in (g), the water-treated molding is dried at a temperature in the range of from 100 to 150° C. for a duration in the range of from 10 to 20 h and calcined at a temperature in the range of from 400 to 500° C. for a duration in the range of from 1 to 3 h.

17. The process of any of embodiments 7 to 16, wherein the molding is not subjected to steaming.

Regarding said preferred process for the preparation of said catalyst according to (b) in the form of a micropowder and/or a molding, comprising the ZnTiMWW, described above by embodiments 1 to 17, the ZnTiMWW based on which the suspension in embodiment 1.(a) is provided, can be prepared according to all conceivable methods. For example, it is possible to prepare a microporous aluminum-free zeolitic material of structure type MWW containing titanium (TiMWW) and subject the TiMWW to a suitable treatment to obtain the ZnTiMWW. Further, it is possible to prepare an aluminum-free zeolitic material of structure type MWW (MWW) and subject the MWW to a suitable treatment to obtain the ZnTiMWW wherein, for example, both Zn and Ti are suitably incorporated in the MWW. Further, it is conceivable to prepare aluminum-free zeolitic material of structure type MWW wherein, during the synthesis of the MWW-type framework, Ti is introduced and the resulting material is subjected to a suitable treatment to incorporate Zn, or Zn is introduced and the resulting material is subjected to a suitable treatment to incorporate Ti, or both Zn and Ti are introduced. As conceivable methods for the preparation of TiMWW, the processes as described, for example, in U.S. Pat. No. 6,114,551, or in Wu et al., "Hydrothermal Synthesis of a novel Titanosilicate with MWW Topology", Chemistry Letters (2000), pp. 774-775 may be mentioned. Preferably, an aluminum-free zeolitic material of structure type MWW containing Ti (TiMWW) is prepared in a first stage, and in a second stage, the TiMWW is subjected to a suitable treatment to obtain the ZnTiMWW. More preferably, the ZnTiMWW is prepared according to a process comprising (I) preparing an aluminum-free zeolitic material of structure type MWW containing boron (B-MWW);
(II) deboronating the B-MWW to obtain an aluminum-free zeolitic material of structure type MWW (MWW);
(III) incorporating titanium (Ti) into the MWW to obtain an aluminum-free zeolitic material of structure type MWW containing Ti (TiMWW);
(IV) preferably acid-treating the TiMWW;
(V) subjecting the TiMWW to zinc (Zn) impregnation to obtain the ZnTiMWW.

Preferably, in stage (I), the B-MWW is prepared by a process whose preferred steps and conditions are defined by the following embodiments 1 to 28 and the respective dependencies as indicated:

1. A process for preparing an aluminum-free boron containing zeolitic material comprising the framework structure MWW (B-MWW), comprising
   (a) hydrothermally synthesizing a B-MWW precursor from a synthesis mixture containing water, a silicon source, a boron source, and an MWW template compound obtaining the B-MWW precursor in its mother liquor, the mother liquor having a pH above 9;
   (b) adjusting the pH of the mother liquor, obtained in (a) and containing the B-MWW precursor, to a value in the range of from 6 to 9;
   (c) separating the B-MWW precursor from the pH-adjusted mother liquor obtained in (b) by filtration in a filtration device.
2. The process of embodiment 1, wherein in (a), at least 95 weight-%, preferably at least 99 weight-%, more preferably at least 99.9 weight-% of the synthesis mixture consist of the water, the silicon source, the boron source, and the template compound.
3. The process of embodiment 1 or 2, wherein in (a), the silicon source is selected from the group consisting of fumed silica, colloidal silica, and a mixture thereof, the silicon source preferably being colloidal silica, more preferably ammonia-stabilized silica, the boron source is selected from the group consisting of boric acid, borates, boron oxide, and a mixture of two or more thereof, the boron source preferably being boric acid, and the MWW template compound selected from the group consisting of piperidine, hexamethylene imine, N,N,N,N',N',N'-hexamethyl-1,5-pentanediammonium ion, 1,4-bis(N-methylpyrrolidinium) butane, octyltrimethylammonium hydroxide, heptyltrimethylammonium hydroxide, hexyltrimethylammonium hydroxide, N,N,N-trimethyl-1-adamantylammonium hydroxide, and a mixture of two or more thereof, the MWW template compound preferably being piperidine.
4. The process of any of embodiments 1 to 3, wherein in (a), the synthesis mixture contains the boron source, calculated as elemental boron, relative to the silicon source, calculated as elemental silicon, in a molar ratio in the range of from 0.4:1 to 2.0:1, preferably from 0.6:1 to 1.9:1, more preferably from 0.9:1 to 1.4:1, the water relative to the silicon source, calculated as elemental silicon, in a molar ratio in the range of from 1:1 to 30:1, preferably from 3:1 to 25:1, more preferably from 6:1 to 20:1; and the template compound relative to the silicon source, calculated as elemental silicon, in a molar ratio in the range of from 0.4:1 to 2.0:1, preferably from 0.6:1 to 1.9:1, more preferably from 0.9:1 to 1.4:1.
5. The process of any of embodiments 1 to 4, wherein in (a), the hydrothermal synthesizing is carried out at a temperature in the range of from 160 to less than 180° C., preferably from 170 to 175° C., for a period of time in the range of from 1 to 72 h, preferably from 6 to 60 h, more preferably from 12 to 50 h.
6. The process of any of embodiments 1 to 5, wherein in (a), the hydrothermal synthesizing is carried out at least partially under stirring.
7. The process of any of embodiments 1 to 6, wherein in (a), the synthesis mixture additionally contains a seeding material, preferably a zeolitic material comprising the framework structure MWW, more preferably a boron containing zeolitic material comprising the framework structure MWW.
8. The process of embodiment 7, wherein the synthesis mixture contains the seeding material, relative to the silicon source, in a weight ratio in the range of from 0.01:1 to 1:1, preferably from 0.02:1 to 0.5:1, more preferably from 0.03:1 to 0.1:1, calculated as amount of seeding material in kg relative to silicon contained in the silicon source calculated as silicon dioxide in kg.
9. The process of any of embodiments 1 to 8, wherein the pH of the mother liquor obtained from (a) is above 10, preferably in the range of from 10.5 to 12, more preferably from 11 to 11.5.
10. The process of any of embodiments 1 to 9, wherein in (b), the pH of the mother liquor obtained in (a) is adjusted to a value in the range of from 6.5 to 8.5, preferably from 7 to 8.
11. The process of any of embodiments 1 to 10, wherein in (b), the pH is adjusted by a method comprising
    (aa) adding an acid to the mother liquor obtained from (a) containing the B-MWW precursor, wherein the adding is preferably carried out at least partially under stirring.

12. The process of embodiment 11, wherein in (aa), the adding is carried out at a temperature in the range of from 20 to 70° C., preferably from 30 to 65° C., more preferably from 40 to 60° C.
13. The process of embodiment 11 or 12, wherein in (aa), the acid is an inorganic acid, preferably an aqueous solution containing the inorganic acid.
14. The process of embodiment 13, wherein the inorganic acid is selected from the group consisting of phosphoric acid, sulphuric acid, hydrochloric acid, nitric acid, and a mixture of two or more thereof, the inorganic acid preferably being nitric acid.
15. The process of any of embodiments 11 to 14, the method additionally comprising
    (bb) stirring the mother liquor to which the acid was added according to (aa), wherein during (bb), no acid is added to the mother liquor.
16. The process of embodiment 15, wherein in (bb), the stirring is carried out at a temperature in the range of from 20 to 70° C., preferably from 25 to 65° C., more preferably from 30 to 60° C.
17. The process of any of embodiments 1 to 16, wherein in (b), the size of the particles contained in the mother liquor, expressed by the respective Dv10, Dv50, and Dv90 value, is increased for at least 2%, preferably at least 3%, more preferably at least 4.5% regarding Dv10, for at least 2%, preferably at least 3%, more preferably at least 4.5% regarding Dv50, and for at least 5%, preferably at least 6%, more preferably at least 7% regarding Dv90.
18. The process of any of embodiments 1 to 17, wherein the pH-adjusted mother liquor obtained from (b) has a solids content in the range of from 1 to 10 weight-%, preferably from 4 to 9 weight-%, more preferably from 7 to 8 weight-%, based on the total weight of the pH-adjusted mother liquor obtained from (b).
19. The process of any of embodiments 1 to 18, wherein the pH-adjusted mother liquor obtained from (b) has a filtration resistance in the range of from 10 to 50 mPa*s/m$^2$, preferably from 15 to 45 mPa*s/m$^2$, more preferably from 20 to 40 mPa*s/m$^2$.
20. The process of any of embodiments 1 to 19, further comprising
    (d) washing the B-MWW precursor obtained from (c), preferably the filter cake obtained from (c), wherein the washing is preferably performed using water was washing agent.
21. The process of embodiment 20, wherein in (d), the filter cake obtained from (c) is has a washing resistance in the range of from 10 to 50 mPa*s/m$^2$, preferably from 15 to 45 mPa*s/m$^2$, more preferably from 20 to 40 mPa*s/m$^2$.
22. The process of embodiment 20 or 21, wherein the washing is carried out until the conductivity of the filtrate is at most 300 microSiemens/cm, preferably at most 250 microSiemens/cm, more preferably at most 200 microSiemens/cm.
23. The process of any of embodiments 1 to 22, further comprising
    (e) drying the B-MWW precursor obtained from (c), preferably from (d), at a temperature in the range of from 20 to 50° C., preferably from 20 to 40° C., more preferably from 20 to 30° C., wherein the drying is preferably carried out by subjecting the B-MWW to a gas stream, preferably a nitrogen stream.
24. The process of any of embodiments 1 to 23, wherein the residual moisture of the B-MWW precursor obtained from (c), preferably from (d), more preferably from (e), is in the range of from 80 to 90 weight-%, preferably from 80 to 85 weight-%.
25. The process of any of embodiments 1 to 24, further comprising
    (f) preparing a suspension, preferably an aqueous suspension, containing the B-MWW precursor obtained from to (c), preferably from (d), more preferably from (e), and having a solids content in the range of from 10 to 20 weight-%, preferably from 12 to 18 weight-%, more preferably from 14 to 16 weight-%;
    (g) spray drying the suspension obtained from (f) containing the B-MWW precursor, obtaining a spray powder;
    (h) calcining the spray powder obtained from (g) containing the B-MWW precursor, preferably at a temperature in the range of from 500 to 700° C., more preferably from 550 to 650° C., more preferably from 575 to 625° C. for a period of time in the range of from 1 to 24 h, preferably from 2 to 18 h, more preferably from 6 to 12 h, obtaining a spray powder of which at least 99 weight-%, more preferably at least 99.5 weight-% consist of the B-MWW.
26. The process of embodiment 25, wherein in (h), the calcining is carried out in continuous mode, preferably in a rotary calciner, preferably at a throughput in the range of from 0.5 to 20 kg spray powder per h.
27. The process of embodiment 25 or 26, wherein the degree of crystallinity of the B-MWW contained in the spray powder obtained from (h) is at least (75±5) %, preferably at least (80±5) %, as determined via XRD.
28. The process of any of embodiments 25 to 27, wherein the BET specific surface area of the B-MWW contained in the spray powder obtained from (h) is at least 300 m$^2$/g, preferably in the range of from 300 to 500 m$^2$/g, as determined according to DIN 66131.

Preferably, stage (II) is carried by a process whose preferred steps and conditions are defined by the following embodiments 1 to 7 and the respective dependencies as indicated:

1. A process for the preparation of a zeolitic material, comprising
    (a) providing the boron-containing zeolitic material of structure type MWW (B-MWW) obtained according to stage (I);
    (b) deboronating the B-MWW by treating the B-MWW with a liquid solvent system thereby obtaining a deboronated B-MWW (MWW);
    wherein the liquid solvent system is selected from the group consisting of water, monohydric alcohols, polyhydric alcohols, and mixtures of two or more thereof, and wherein said liquid solvent system does not contain an inorganic or organic acid or a salt thereof, the acid being selected from the group consisting of hydrochloric acid, sulfuric acid, nitric acid, phosphoric acid, formic acid, acetic acid, propionic acid, oxalic acid, and tartaric acid.
2. The process of embodiment 1, wherein the liquid solvent system does not contain an inorganic or organic acid, or a salt thereof.
3. The process of embodiment 1 or 2, wherein the liquid solvent system is selected from the group consisting of water, methanol, ethanol, propanol, ethane-1,2-diol, propane-1,2-diol, propane-1,3-diol, propane-1,2,3-triol, and mixtures of two or more thereof, preferably water.

4. The process of any of embodiments 1 to 3, wherein the treating according to (b) is carried out at a temperature in the range of from 50 to 125° C.
5. The process of any of embodiments 1 to 4, wherein the treating according to (b) is carried out for a time in the range of from 6 to 20 h.
6. The process of any of embodiments 1 to 5, wherein the treating according to (b) is carried out in at least 2 separate steps, wherein between at least 2 treating steps, the MWW is dried, preferably at a temperature in the range of from 100 to 150° C.
7. The process of any of embodiments 1 to 6, further comprising
   (c) post-treating the MWW obtained from (b) by a process comprising
      (c.1) separating the MWW from the liquid solvent system;
      (c.2) preferably drying the separated MWW, preferably by spray-drying;
      (c.3) optionally calcining the MWW obtained from (c.1) or (c.2), preferably at temperatures in the range of from 500 to 700° C.

As far as stage (III) is concerned, preferably a suitable starting mixture, preferably an aqueous mixture, containing the MWW and a Ti containing precursor, and preferably containing at least one suitable micropore-forming agent, is subjected to hydrothermal crystallization under autogenous pressure. It may be conceivable to use at least one suitable seeding material. As suitable Ti containing precursor, tetraalkylorthotitanates such as tetrabutyl orthotitanate may be mentioned by way of example. As suitable micropore-forming agent, piperidine, hexamethylene imine, or mixtures of piperidine and hexamethylene imine may be mentioned by way of example. Preferably, the crystallization time is in the range of from 4 to 8 days, more preferably from 4 to 6 days. During hydrothermal synthesis, the crystallization mixture may be stirred. The temperatures applied during crystallization are preferably in the range of from 160 to 200° C., more preferably from 160 to 180° C. After hydrothermal synthesis, the obtained crystalline zeolitic material TiMWW is preferably suitably separated from the mother liquor. All methods of separating the TiMWW from its mother liquor are conceivable. These methods include, for example, filtration, ultrafiltration, diafiltration and centrifugation methods or, for instance, spray drying processes and spray granulation processes. A combination of two or more of these methods can be applied. According to the present invention, the TiMWW is preferably separated from its mother liquid by filtration to obtain a filter cake which is preferably subjected to washing, preferably with water. Subsequently, the filter cake, optionally further processed to obtained a suitable suspension, is subjected to spray drying or to ultrafiltration. Prior to separating the TiMWW from its mother liquor, it is possible to increase the TiMWW content of the mother liquor by concentrating the suspension. If washing is applied, it is preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm. After separation of the TiMWW from its mother liquor, preferably achieved via filtration, and after washing, the washed filter cake containing the TiMWW is preferably subjected to pre-drying, for example by subjecting the filter cake to a suitable gas stream, preferably a nitrogen stream, for a time preferably in the range of from 4 to 10 h, more preferably from 5 to 8 h. Subsequently, the pre-dried filter cake is preferably dried at temperatures in the range of from 100 to 300° C., more preferably from 150 to 275° C., more preferably from 200 to 250° C. in a suitable atmosphere such as technical nitrogen, air, or lean air, preferably in air or lean air. Such drying can be accomplished, for example, by spray-drying. After drying, the TiMWW may be subjected to calcination at temperatures in the range of from 500 to 700° C., more preferably from 550 to 675° C., more preferably from 600 to 675° C. in a suitable atmosphere such as technical nitrogen, air, or lean air, preferably in air or lean air. Preferably, no calcination is carried out according to (III).

Preferably, stages (III) and (IV) are carried out by a process whose preferred steps and conditions are defined by the following embodiments 1 to 27 and the respective dependencies as indicated:

1. A process for the preparation of a titanium-containing zeolitic material having an MWW framework structure comprising
   (a) providing the deboronated crystalline zeolitic material MWW obtained according to stage (II);
   (b) incorporating titanium into the zeolitic material provided in (a) comprising
      (b.1) preparing an aqueous synthesis mixture containing the zeolitic material provided in (i), an MWW template compound and a titanium source, wherein the molar ratio of the MWW template compound relative to Si, calculated as $SiO_2$ and contained in the zeolitic material provided in (a), is in the range of from 0.5:1 to 1.4:1;
      (b.2) hydrothermally synthesizing a titanium-containing zeolitic material having an MWW framework structure from the aqueous synthesis mixture prepared in (b.1), obtaining a mother liquor comprising the titanium-containing zeolitic material having an MWW framework structure;
   (c) spray-drying the mother liquor obtained from (b.2) comprising the titanium-containing zeolitic material having an MWW framework structure.
2. The process of embodiment 1, wherein in (b.1), the MWW template compound is selected from the group consisting of piperidine, hexamethylene imine, N,N,N,N', N',N'-hexamethyl-1,5-pentanediammonium ion, 1,4-bis (N-methylpyrrolidini-um)butane, octyltrimethylammonium hydroxide, heptyltrimethylammonium hydroxide, hexyltrimethylammonium hydroxide, and a mixture of two or more thereof, the MWW template compound preferably being piperidine.
3. The process of embodiment 1 or 2, wherein in (b.1), the titanium source is selected from the group consisting of tetrabutyl orthotitanate, tetraisopropyl orthotitanate, tetraethyl orthotitanate, titanium dioxide, titanium tetrachloride, titanium tert-butoxide, and a mixture of two or more thereof, the titanium source preferably being tetrabutyl orthotitanate.
4. The process of any of embodiments 1 to 3, wherein in the aqueous synthesis mixture in (b.1), the molar ratio of Ti, calculated as $TiO_2$ and contained in the titanium source, relative to Si, calculated as $SiO_2$ and contained in the zeolitic material having a molar ratio $B_2O_3:SiO_2$ of at most 0.02:1, is in the range of from 0.005:1 to 0.1:1, preferably from 0.01:1 to 0.08:1, more preferably from 0.02:1 to 0.06:1.
5. The process of any of embodiments 1 to 4, wherein in the aqueous synthesis mixture in (b.1), the molar ratio of $H_2O$ relative to Si, calculated as $SiO_2$ and contained in the zeolitic material having a molar ratio $B_2O_3:SiO_2$ of at most 0.02:1, is in the range of from 8:1 to 20:1, preferably from 10:1 to 18:1, more preferably from 12:1 to 16:1.
6. The process of any of embodiments 1 to 5, wherein in the aqueous synthesis mixture in (b.1), the molar ratio of the MWW template compound relative to Si, calculated as $SiO_2$ and contained in the zeolitic material provided in (i), is in the range of from 0.5:1 to 1.7:1, preferably from 0.8:1 to 1.5:1, more preferably from 1.0:1 to 1.3:1.
7. The process of any of embodiments 1 to 6, wherein in (b.2), the hydrothermal synthesizing is carried out at a temperature in the range of from 80 to 250° C., preferably from 120 to 200° C., more preferably from 160 to 180° C.
8. The process of any of embodiments 1 to 7, wherein in (b.2), the hydrothermal synthesizing is carried out for a period in the range of from 10 to 100 h, more preferably from 20 to 80 h, more preferably from 40 to 60 h.
9. The process of any of embodiments 1 to 8, wherein in (b.2), the hydrothermal synthesizing is carried out in a closed system under autogenous pressure.
10. The process of any of embodiments 1 to 9, wherein neither during (b.2), nor after (b.2) and before (c), the titanium-containing zeolitic material having an MWW framework structure is separated from its mother liquor.
11. The process of any of embodiments 1 to 10, wherein the mother liquor subjected to (c) comprising the titanium-containing zeolitic material having an MWW framework structure has a solids content, optionally after concentration or dilution, in the range of from 5 to 25 weight-%, more preferably from 10 to 20 weight-%, based on the total weight of the mother liquor comprising the titanium-containing zeolitic material.
12. The process of any of embodiments 1 to 11, wherein during spray-drying in (c), the drying gas inlet temperature is in the range of from 200 to 350° C. and the drying gas outlet temperature is in the range of from 70 to 190° C.
13. The process of any of embodiments 1 to 12, wherein the zeolitic material having an MWW framework structure obtained from (c) has a Si content in the range of from 30 to 40 weight-%, calculated as elemental Si, a total organic carbon content (TOC) in the range of from 0 to 14 weight-%, and a Ti content of from 2.1 to 2.8 weight-%, calculated as elemental titanium, in each case based on the total weight of the zeolitic material.
14. The process of any of embodiments 1 to 13, further comprising
 (d) treating the titanium-containing zeolitic material having an MWW framework structure obtained from (iii) with an aqueous solution having a pH of at most 5.
15. The process of embodiment 14, wherein after (c) and before (d), the spray-dried titanium-containing zeolitic material having an MWW framework structure obtained from (c) is not subjected to calcination.
16. The process of embodiment 14 or 15, wherein in (d), the weight ratio of the aqueous solution relative to the titanium-containing zeolitic material having an MWW framework structure is in the range of from 10:1 to 30:1, preferably from 15:1 to 25:1, more preferably from 18:1 to 22:1.
17. The process of any of embodiments 14 to 16, wherein in (d), the aqueous solution comprises an inorganic acid, preferably selected from the group consisting of phosphoric acid, sulphuric acid, hydrochloric acid, nitric acid, and a mixture of two or more thereof, the aqueous solution preferably comprising nitric acid.
18. The process of any of embodiments 14 to 17, wherein in (d), the aqueous solution has a pH in the range of from 0 to 5, preferably from 0 to 3, more preferably from 0 to 2.
19. The process of any of embodiments 14 to 18, wherein in (d), the titanium-containing zeolitic material having an MWW framework structure is treated with the aqueous solution at a temperature in the range of from 50 to 175° C., preferably from 70 to 125° C., more preferably from 95 to 105° C.
20. The process of any of embodiments 14 to 19, wherein in (d), the titanium-containing zeolitic material having an MWW framework structure is treated with the aqueous solution for a period in the range of from 0.1 to 6 h, preferably from 0.3 to 2 h, more preferably from 0.5 to 1.5 h.
21. The process of any of embodiments 14 to 20, wherein the treating according to (d) is carried out in a closed system under autogenous pressure.
22. The process of any of embodiments 14 to 21, further comprising
 (e) separating the titanium-containing zeolitic material having an MWW framework structure obtained from (d) from the aqueous solution, optionally followed by washing the separated titanium-containing zeolitic material having an MWW framework.
23. The process of embodiment 22, wherein (e) comprises drying the separated and optionally washed titanium-containing zeolitic material having an MWW framework structure.
24. The process of any of embodiments 14 to 23, further comprising
 (f) preparing a suspension, preferably an aqueous suspension containing the titanium-containing zeolitic material having an MWW framework structure obtained from (d), preferably from (e), said suspension having a solids content preferably in the range of from 5 to 25 weight-%, more preferably from 10 to 20 weight-%, based on the total weight of the suspension, and subjecting the suspension to spray-drying.
25. The process of embodiment 24, wherein during spray-drying, the drying gas inlet temperature is in the range of from 200 to 330° C. and the drying gas outlet temperature is in the range of from 120 to 180° C.
26. The process of any of embodiments 14 to 25, further comprising
 (g) calcining the titanium containing zeolitic material having an MWW framework structure obtained from (d), preferably from (e), more preferably from (f), wherein the calcining is preferably carried out at a temperature in the range of from 400 to 800° C., more preferably from 600 to 700° C.
27. The process of embodiment 26, wherein in (vii), the calcining is carried out in continuous mode, preferably with a rate in the range of from 0.2 to 2.0 kg zeolitic material per hour, more preferably from 0.5 to 1.5 kg zeolitic material per hour.

According to stage (V), the TiMWW preferably obtained according to stage (IV) is subjected to a suitable Zn treatment to obtain the ZnTiMWW used for the preparation of the suspension according to (a). Generally, as far as (V) is concerned, no specific restrictions exist provided that above-defined preferred ZnTiMWW can be obtained having the preferred Zn and Ti content. Most preferably, stage (V) comprises at least one suitable impregnation stage, more preferably at least one wet impregnation stage. Concerning this impregnation stage, it is preferred to contact the TiMWW preferably as obtained according to (IV) is contacted with at least one suitable Zn-containing precursor in at least one suitable solvent (wet impregnation), most preferably water. As suitable Zn-containing precursor, water-soluble Zn salts are especially preferred, with zinc acetate dihydrate being especially preferred. It is further preferred to prepare a solution of the Zn-containing precursor, preferably an aqueous solution, and to suspend the TiMWW in this solution. Further preferably, impregnation is carried out at elevated temperatures, relative to room temperature, preferably in the range of from 75 to 125° C., more preferably from 85 to 115° C., for a time preferably in the range of from 3.5 to 5 h, more preferably from 3 to 6 h. Stirring the suspension during impregnation is preferred. After the impregnation, the obtained ZnTiMWW is preferably suitably separated from the suspension. All methods of separating the ZnTiMWW from the suspension are conceivable. Especially preferably, separation is carried out via filtration, ultrafiltration, diafiltration or centrifugation methods. A combination of two or more of these methods can be applied. According to the present invention, the ZnTiMWW is preferably separated from the suspension by filtration to obtain a filter cake which is preferably subjected to washing, preferably with water. If washing is applied, it may be preferred to continue the washing process until the washing water has a conductivity of less than 1,000 microSiemens/cm, more preferably of less than 900 microSiemens/cm, more preferably of less than 800 microSiemens/cm, more preferably of less than 700 microSiemens/cm. Subsequently, the preferably washed filter cake is subjected to pre-drying, for example by subjecting the filter cake to a suitable gas stream, preferably a nitrogen stream, for a time preferably in the range of from 5 to 15 h, more preferably from 8 to 12.

If TiMWW or ZnTiMWW is used as catalytically active material according to the present invention, it is preferred that the organic solvent comprises, preferably essentially consists of acetonitrile.

Therefore, the present invention preferably relates to a process for the regeneration of a catalyst comprising a titanium containing zeolite having framework structure MWW optionally comprising zinc, as catalytically active material, said catalyst having been used in a process for the preparation of an olefin oxide comprising
(i) providing a mixture comprising acetonitrile, an olefin, an epoxidation agent and an at least partially dissolved potassium comprising salt;
(ii) subjecting the mixture provided in (i) in a reactor to epoxidation conditions in the presence of the catalyst, obtaining a mixture comprising acetonitrile and the olefin oxide, and obtaining the catalyst having a potassium salt deposited thereon;
said process for the regeneration comprising
(a) separating the mixture obtained from (ii) from the catalyst;
(b) washing the catalyst obtained from (a) with a liquid aqueous system;
(c) optionally drying the catalyst obtained from (b) in a gas stream comprising an inert gas at a temperature of less than 300° C.;
(d) calcining the catalyst obtained from (c) in a gas stream comprising oxygen at a temperature of at least 300° C.

Especially preferably, the present invention preferably relates to a process for the regeneration of a catalyst comprising a titanium containing zeolite having framework structure MWW optionally comprising zinc, as catalytically active material, said catalyst having been used in a continuous process for the preparation of propylene oxide comprising
(i) providing a mixture comprising acetonitrile, propene, hydrogen peroxide, water, optionally propene, and an at least partially dissolved potassium comprising salt, wherein the potassium comprising salt is selected from the group consisting of dihydrogen phosphate, dipotassium hydrogen phosphate, potassium formate, and a mixture of two or more thereof;
(ii) subjecting the mixture provided in (i) in a reactor to epoxidation conditions in the presence of the catalyst, obtaining a mixture comprising acetonitrile and the propylene oxide, water, optionally propene, optionally propane, and obtaining the catalyst having the potassium salt deposited thereon,
wherein the mixture according to (i) contains the potassium comprising salt with a molar ratio of potassium comprised in the potassium comprising salt relative to hydrogen peroxide in the range of from $10 \times 10^{-6}:1$ to $1500 \times 10^{-6}:1$, preferably from $20 \times 10^{-6}:1$ to $1300 \times 10^{-6}:1$, more preferably from $30 \times 10^{-6}:1$ to $1000 \times 10^{-6}:1$,
said process for the regeneration comprising
(a) separating the mixture obtained from (ii) from the catalyst;
(b) washing the catalyst obtained from (a) with a liquid aqueous system which contains at least 99.9 weight-% water, more preferably at least 99.99 weight-% water, more preferably at least 99.999 weight-% water, based on the total weight of the liquid aqueous system, at a pressure in the range of from 0.8 to 1.5 bar, preferably from 1.0 to 1.4 bar, and a temperature in the range of from 40 to 90° C., preferably from 60 to 80° C.;
(c) optionally drying the catalyst obtained from (b) in a gas stream comprising an inert gas at a temperature in the range of from 25 to 100° C., preferably from 30 to 50° C.;
(d) calcining the catalyst obtained from (b) or (c), preferably (c), in a gas stream comprising oxygen employed in (d) contains oxygen in the range of from 3 to 40 volume-%, preferably from 5 to 50 volume-% based on the total volume of the gas stream at a temperature of at a temperature in the range of from 375 to 525° C., preferably from 400 to 500° C.

TS-1 Catalyst

According to the present invention, a titanium silicalite-1 catalyst, preferably a fixed-bed titanium silicalite-1 catalyst, can be employed as catalyst. Titanium silicalite-1 is a microporous zeolite of structure type MFI which contains no aluminum and in which the Si(IV) in the silicate lattice is partly replaced by titanium as Ti(IV). The term "micropores" as used in the context of the present invention relates to pores having a pore size smaller than 2 nm, determined according to DIN 66134.

The titanium silicalite-1 zeolite of the catalyst can in principle be prepared by any conceivable method. Typically, the synthesis of the at least one titanium zeolite according to the present invention is carried out in hydrothermal systems involving the combination of an active source of silicon oxide and a titanium source, such as titanium oxide, with at least one template compound capable of forming the desired titanium zeolite in an aqueous suspension, for example in a basic suspension. Typically, organic templates are employed. Preferably, the synthesis is carried out at elevated temperatures, for example temperatures in the range of from to 150 to 200° C., preferably from 160 to 180° C.

In principle, any suitable compound can be used as silicon oxide source. Typical sources of silicon oxide ($SiO_2$) include silicates, silica hydrogel, silicic acid, colloidal silica, fumed silica, tetraalkoxysilanes, silicon hydroxides, precipitated silica and clays. Both so-called "wet-process" silicon dioxide and so-called "dry-process" silicon dioxide can be employed. In these cases, the silicon dioxide is particularly preferably amorphous, wherein the size of the silicon dioxide particles is, for example, in the range of from 5 to 100 nm and the surface area of the silicon dioxide particles is, for example, in the range of from 50 to 500 m$^2$/g. Colloidal silicon dioxide is, inter alia, commercially available as Ludox®, Syton®, Nalco®, or Snowtex®. "Wet process" silicon dioxide is, inter alia, commercially available as Hi-Sil®, Ultrasil®, Vulcasil®, Santocel®, Valron-Estersil®, Tokusil® or Nipsil®. "Dry process" silicon dioxide is commercially available, inter alia, as Aerosil®, Reolosil®, Cab-O-Sil®, Fransil® or ArcSilica®. It is as well within the scope of the present invention to use a silicon dioxide precursor compound as silicon oxide source. For example, tetraalkoxysilanes, such as for example, tetraethoxysilane or tetrapropoxysilane, may be mentioned as precursor compound.

As template, any template suitable to provide the desired MFI zeolitic structure can be used. In particular, tetrapropylammonium hydroxide, more preferably tetra-n-propylammonium hydroxide is employed. In a preferred embodiment of the process according to the invention, the at least one pore forming agent is removed in a later step by calcination, as described below.

Typically, the synthesis of the titanium silicalite-1 is carried out batchwise in an autoclave so that the reaction suspension is subjected to autogenous pressure for a number of hours or a few days until the titanium silicalite-1 zeolite is obtained. According to a preferred embodiment of the present invention, the synthesis generally proceeds at elevated temperatures wherein the temperatures during the hydrothermal crystallization step are typically in the range of from 150 to 200° C., preferably in the range of from 160 to 180° C. Usually, the reaction is carried out for a time in the range of a few hours to several days, preferably for a time in the range of from 12 h to 48 h, more preferably from 20 to 30 h. It is further conceivable to add seed crystals to the synthesis batches.

According to an embodiment of the present invention, the crystalline titanium silicalite-1 obtained is separated off from the reaction suspension, i.e. from the mother liquor, optionally washed and dried.

All methods known for the separation of the crystalline titanium silicalite-1 from the suspension can be employed. Inter alia, filtration, ultra-filtration, diafiltration and centrifugation methods should be mentioned.

In case the crystalline titanium silicalite-1 obtained is washed, said washing step can be carried out employing any suitable wash substance, such as, for example, water, alcohols, such as for example, methanol, ethanol, or methanol and propanol, or ethanol and propanol, or methanol and ethanol and propanol, or mixtures of water and at least one alcohol, such as, for example, water and ethanol or water and methanol, or water and ethanol, or eater and propanol, or water and methanol and ethanol, or water and methanol and propanol, or water and ethanol and propanol or water and ethanol and methanol and propanol. Water or a mixture of water and at least one alcohol, preferably water and ethanol, are used as wash substance.

Drying of the crystalline titanium silicalite-1 is effected at temperatures, in general, in the range of from 80 to 160° C., preferably from 90 to 145° C., particularly preferably from 100 to 130° C.

Instead of the above mentioned separation methods, such as, inter alia, filtration, ultra-filtration, diafiltration and centrifugation methods, the suspension may, according to an alternative embodiment, also be subjected to spray methods, as for example spray-granulation and spray-drying.

If the separation of the crystalline titanium silicalite-1 is carried out by means of spray method, the separating and drying step can be combined to a single step. In such case, either the reaction suspension as such or a concentrated reaction suspension can be employed. Additionally, it is possible to add a suitable additive as for example at least one suitable binder and/or at least one pore forming agent to the suspension—either to the reaction suspension as such or to the concentrated suspension—prior to spray drying or spray granulation. Suitable binders are described in detail below. As pore forming agent all pore forming agents described above can be used. In case the suspension is spray-dried, the pore forming agent—if added—may be added in two manners. First, the pore forming agent can be added to the reaction mixture prior to spray drying. However, it is also possible to add a portion of the pore forming agent to the reaction mixture prior to spray drying, with the remainder of the pore forming agent being added to the spray dried material.

In case the suspension is first concentrated to enhance the content of the titanium silicalite-1 in the suspension, concentration can be achieved, for example, by evaporating, as for example evaporating under reduced pressure, or by cross flow filtration. Likewise, the suspension can be concentrated by separating said suspension into two fractions, wherein the solid contained in one of both fractions is separated off by filtration, diafiltration, ultrafiltration or centrifugation methods and is suspended after an optional washing step and/or drying step in the other fraction of the suspension. The thus obtained concentrated suspension can then be subjected to spray methods, as for example spray granulation and spray drying.

According to an alternative embodiment, concentration is achieved by separating the at least one titanium zeolite from the suspension, and re-suspending the titanium zeolite, optionally together with at least one suitable additive as already described above, wherein the titanium zeolite may be subjected to at least one washing step and/or at least one drying step prior to resuspension. The re-suspended titanium zeolite can then be employed to spraying methods, preferably to spray drying.

Spray-drying is a direct method of drying slurries, suspensions or solutions by feeding a well-dispersed liquid-solid slurry, suspension or solution, often additionally containing a binder, to an atomizer and subsequently flash-drying in a stream of hot air. The atomizer can be of several different types. Most common is wheel atomization which uses high-speed rotation of a wheel or a disc to break up the slurry into droplets that spin out from the wheel into a chamber and are flash-dried prior to hitting the chamber walls. The atomization may also be accomplished by single fluid nozzles which rely on hydrostatic pressure to force the slurry through a small nozzle. Multi-fluid nozzles are also used, where gas pressure is used to force the slurry through the nozzle. The sprayed material obtained using spray drying and spray granulation methods, like for example fluidized-bed drying, can contain solid and/or hollow spheres and can substantially consist of such spheres, which have, for example, a diameter in the range of from 5 to 500 μm or 5 to 300 μm. Single component or multiple component nozzles can be used. The use of a rotating sprayer is also conceivable. Possible inlet temperatures for the used carrier gas are, for example, in the range of from 200 to 600° C., preferably in the range of from 300 to 500° C. The outlet temperature of the carrier gas is, for example, in the range of from 50 to 200° C. Air, lean air or oxygen-nitrogen mixtures with an oxygen content of up to 10 vol.-%, preferably of up to 5 vol. %, more preferably of less than 5 vol. %, as, for example, of up to 2 vol. %, may be mentioned as carrier gases. The spray methods can be carried out in counter-current or co-current flow.

Preferably, the titanium silicalite-1 is separated from the reaction suspension by conventional filtration or centrifugation, optionally dried and/or calcined, and re-suspended, preferably in a mixture, preferably an aqueous mixture of at least one binder material and/or one pore-forming agent. The resulting suspension is then preferably subjected to spray-drying or spray-granulation. The obtained sprayed material may be subjected to an additional washing step, said washing step being carried out as described above. The optionally washed sprayed material is then dried and calcined wherein drying and calcination is preferably carried out as described above.

According to an alternative embodiment, the crystallization of the titanium silicalite-1 is effected not before the above described suspension has been spray dried. Therefore, first a suspension is formed comprising the source of silicon oxide, preferably silicon dioxide, the source of titanium oxide, and the template compound capable of forming the titanium silicalite-1. Then, the suspension is spray-dried, wherein subsequently, optionally additional pore forming agent is added to the spray-dried titanium silicalite-1.

The spray-dried titanium silicalite-1 obtained according to the above mentioned processes can, optionally, be subjected to at least one wash process If at least one wash process is carried out, preferably at least one drying step and/or at least one calcination step follows.

The titanium silicalite-1, optionally obtained by spraying methods, can further be subjected to at least one calcination step, which is carried out according to a preferred embodiment of the invention subsequent to the drying step, or instead of the drying step. The at least one calcination step is carried out at temperatures in general in the range of from 350-750° C., preferably form 400-700° C., particularly preferably from 450-650° C.

The calcination of the titanium silicalite-1 can be effected under any suitable gas atmosphere, wherein air and/or lean air is preferred. Furthermore, the calcinations is preferably carried out in a muffle furnace, rotary cone and/or a belt calcination furnace, wherein the calcination is generally carried out for one hour or more, for example for a time in the range of from 1 to 24 or from 4 to 12 hours. It is possible in the process according to the present invention, for example, to calcine the titanium silicalite-1 once, twice or more often for in each case at least one hour, for example in each case from 4 h to 12 h, preferably from 4 h to 8 h, wherein it is possible to keep the temperatures during the calcination step constant or to change the temperatures continuously or discontinuously. If calcination is effected twice or more often, the calcination temperatures in the individual steps may be different or identical.

Thus, a preferred embodiment of the present invention relates to a process as described above, wherein the titanium silicalite-1 separated off from the suspension, for example by filtration or spray drying, is washed with a suitable wash substance, and subsequently subjected to at least one drying step. Drying is effected at temperatures, in general, in the range of from 80 to 160° C., preferably from 90 to 145° C., particularly preferably from 100 to 130° C. Most preferably, after drying, a calcinations step is performed. The step is carried out at temperatures in general in the range of from 350-750° C., preferably form 400-700° C., particularly preferably from 450-650° C.

The titanium silicalite-1, prepared as described above, generally can be directly employed as catalyst in stages (i) and (iii). However, it is especially preferred to use a fixed-bed catalyst in both stages (i) and (iii), i.e. to employ not the crystalline zeolitic material per se as catalyst but the crystalline material processed to give a molding comprising the titanium silicalite-1. Thus, according to a preferred embodiment, a molding comprising the titanium silicalite-1, as described above, is employed as catalyst.

In general, in case a molding is employed as catalyst, said catalyst may comprise all conceivable further compounds in addition to the titanium silicalite-1 according to the invention, for example, inter alia, at least one binder and/or at least one pore forming agent. Furthermore, the catalyst may comprise at least one pasting agent instead of the at least one binder and/or the at least one pore forming agent or in addition to the at least one binder and/or the at least one pore forming agent.

As binder all compounds are suitable, which provide adhesion and/or cohesion between the titanium silicalite-1 to be shaped which goes beyond the physisorption which may be present without a binder. Examples of such binders are metal oxides, such as, for example, $SiO_2$, $Al_2O_3$, $TiO_2$, $ZrO_2$ or MgO or clays or mixtures of two or more of these compounds. Clay minerals and naturally occurring or synthetically produced aluminas, such as, for example, alpha-, beta-, gamma-, delta-, eta-, kappa-, chi- or theta-alumina and their inorganic or organometallic precursor compounds, such as, for example, gibbsite, bayerite, boehmite or pseudo-boehmite or trialkoxyaluminates, such as, for example, aluminum triisopropylate, are particularly preferred as $Al_2O_3$ binders. Further preferred binders are amphiphilic compounds having a polar and a non-polar moiety and graphite. Further binders are, for example, clays, such as, for example, montmorillonites, kaolins, metakaoline, hectorite, bentonites, halloysites, dickites, nacrites or anaxites.

These binders can be used as such. It is also within the scope of the present invention to use compounds from which the binder is formed in at least one further step in the production of the moldings. Examples of such binder precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate.

In the context of the present invention binders which either completely or partly comprise $SiO_2$, or which are a precursor of $SiO_2$, from which $SiO_2$ is formed in at least one further step, are very particularly preferred. In this context, both colloidal silica and so-called "wet process" silica and so-called "dry process" silica can be used. Particularly preferably this silica is amorphous silica, the size of the silica particles being, for example, in the range of from 5 to 100 nm and the surface area of the silica particles being in the range of from 50 to 500 $m^2/g$.

Colloidal silica, preferably as an alkaline and/or ammoniacal solution, more preferably as an ammoniacal solution, is commercially available, inter alia, for example as Ludox®, Syton®, Nalco® or Snowtex®. "Wet process" silica is commercially available, inter alia, for example as Hi-Sil®, Ultrasil®, Vulcasil®, Santocel®, Valron-Estersil®, Tokusil® or Nipsil®. "Dry process" silica is commercially available, inter alia, for example as Aerosil®, Reolosil®, Cab-O-Sil®, Fransil® or ArcSilica®. Inter alia, an ammoniacal solution of colloidal silica is preferred in the present invention. Accordingly, the present invention also describes a catalyst containing a molding, as described above, said molding comprising the titanium silicalite-1 as described above and additionally $SiO_2$ as binder material wherein the binder used according to (I) is a binder comprising or forming $SiO_2$. Generally, the titanium zeolite can also be shaped without using a binder.

Thus, the present invention also relates to a process, wherein in stages (i) and (iii), the titanium silicalite-1 catalyst is obtained by shaping the titanium silicalite-1 to give a molding comprising the titanium silicalite-1 and preferably at least one binder, in particular a silica binder.

If desired, at least on pore forming agent can be added to the mixture of titanium silicalite-1 and at least one binder or at least binder-precursor, for further processing and for the formation of the catalyst shaped body to be employed as fixed-bed catalyst. Pore forming agents which may be used are all compounds which, with regard to the molding produced, provide a specific pore size and/or a specific pore size distribution and/or certain pore volumes. In particular, pore forming agents which provide, with regard to the molding produced, micropores and/or micropores, in particular mesopores and micropores.

Thus, the present invention also relates to a process, wherein in stages (i) and (iii), the titanium silicalite-1 catalyst is obtained by shaping the titanium silicalite-1 to give a molding comprising the titanium silicalite-1 and preferably at least one binder, in particular a silica binder, the molding in particular having micropores and mesopores.

As regards examples for pore forming agents which may be used, reference is made to the pore forming agents already mentioned above. Preferably, the pore forming agents used in the shaping process of the invention are polymers which are dispersible, suspendable or emulsifiable in water or in aqueous solvent mixtures. Especially preferred polymers are polymeric vinyl compounds, such as, for example, polyalkylene oxides, such as polyethylene oxides, polystyrene, polyacrylates, polymethacrylates, polyolefins, polyamides and polyesters, carbohydrates, such as, for example, cellulose or cellulose derivatives, such as, for example, methyl cellulose, or sugars or natural fibers. Further suitable pore forming agents are, for example, pulp or graphite.

If desired for the pore size distribution to be achieved, a mixture of two or more pore forming agents may be used. In a particularly preferred embodiment of the process according to the invention, as described below, the pore forming agents are removed by calcination to give the porous catalyst shaped body. Preferably, pore forming agents which provide mesopores and/or micropores, particularly preferably mesopores, are added to the mixture of at least one binder and titanium silicalite-1 for shaping the titanium silicalite-1. Generally, the titanium silicalite-1 can also be shaped to obtain a catalyst shaped body without using a pore forming agent.

Besides binder and optionally pore forming agent it is as well possible to add additional components, for example at least one pasting agent, to the mixture which is shaped to obtain the catalyst shaped body.

If at least one pasting agent is used in the process of the invention, said pasting agent is used either instead of or in addition to the at least one pore forming agent. In particular, compounds which also act as pore forming agents can be used as pasting agent. Pasting agents which may be used are all compounds known to be suitable for this purpose. These are preferably organic, in particular hydrophilic polymers, such as, for example, cellulose, cellulose derivatives, such as, for example, methyl cellulose, and starch, such as, for example, potato starch, wallpaper plaster, polyacrylates, polymethacrylates, polyvinyl alcohol, polyvinylpyrrolidone, polyisobutene or polytetrahydrofuran. The use of water, alcohols or glycols or mixtures thereof, such as mixtures of water and alcohol, or water and glycol, such as for example water and methanol, or water and ethanol, or water and propanol, or water and propylenglycol, as pasting agents may be mentioned. Preferably, cellulose, cellulose derivatives, water and mixtures of two or more of these compounds, such as water and cellulose or water and cellulose derivatives are used as pasting agent. In a particularly preferred embodiment of the process according to the invention, the at least one pasting agents is removed by calcination, as further described below, to give the molding.

According to a further embodiment of the present invention, at least one acidic additive can be added to the mixture which is shaped to obtain the molding. If an acidic additive is used, organic acidic compounds which can be removed by calcination, are preferred. In this context carboxylic acids, such as, for example, formic acid, oxalic acid and/or citric acid, may be mentioned. It is also possible to use two or more of these acidic compounds.

The order of addition of the components to the mixture which is shaped to obtain the molding is not critical. If for example, a combination of a binder, a pore forming agent, a pasting agent and optionally at least one acidic compound is employed, it is possible both first to add the at least one binder then the at least one pore forming agent, the at least one acidic compound and finally the at least one pasting agent and to interchange the sequence with regard to the at least one binder, the at least one pore forming agent, the at least one acidic compound and the at least one pasting agent.

After the addition of at least one binder and/or at least one pasting agent and/or at least one pore forming agent and/or at least one acidic additive to the mixture comprising the titanium silicalite-1, the mixture is typically homogenized for 10 to 180 minutes. Inter alia, kneaders, edge mills or extruders are particularly preferably used for the homogenization. The mixture is preferably kneaded. On an industrial scale, grinding in an edge mill is preferred for the homogenization. The homogenization is, as a rule, carried out at temperatures in the range of from about 10° C. to the boiling point of the pasting agent and atmospheric pressure or slightly super-atmospheric pressure. Optionally, at least one of the compounds described above can then be added. The mixture thus obtained is homogenized, preferably kneaded, until an extrudable plastic material is formed.

The homogenized mixture is then shaped to obtain a molding. All known suitable shaping methods, such as extrusion, spray drying, spray granulation, briquetting, i.e. mechanical compression with or without addition of additional binder or pelleting, i.e. compacting by circular and/or rotary movements, may be employed.

Preferred shaping methods are those in which conventional extruders are employed to shape the mixture comprising the titanium silicalite-1. Thus, for example extrudates having a diameter of from 1 to 10 mm and preferably of from 2 to 5 mm are obtained. In addition to the use of an extruder, an extrusion press can also be used for the preparation of the moldings. The shape of the moldings produced according to the invention can be chosen as desired. In particular, inter alia, spheres, oval shapes, cylinders or tablets are possible. Likewise, hollow structures, as for example hollow cylinders or honeycomb formed structures or also star-shaped geometries may be mentioned.

The shaping can take place at ambient pressure or at a pressure higher than ambient pressure, for example in a pressure range of from 1 bar to several hundred bar. Furthermore, the compacting can take place at ambient temperature or at a temperature higher than ambient temperature, for example in a temperature range of from 20 to 300° C. If drying and/or calcining are part of the shaping step, temperatures of up to 600° C. are conceivable. Finally, the compacting can take place in an ambient atmosphere or in a controlled atmosphere. Controlled atmospheres are, for example, inert gas atmospheres, reducing atmospheres and/or oxidizing atmospheres.

The shaping step is preferably followed by at least one drying step. This at least one drying step is carried out at temperatures in the range of in general from 80 to 160° C., preferably of from 90 to 145° C. and particularly preferably of from 100 to 130° C., usually for 6 h or more, for example in the range of from 6 to 24 h. However, depending on the moisture content of the material to be dried, shorter drying times, such as, for example, about 1, 2, 3, 4 or 5 h are also possible.

Before and/or after the drying step, the preferably obtained extrudate can, for example, be comminuted. Preferably granules or chips having a particle diameter of from 0.1 to 5 mm, in particular of from 0.5 to 2 mm, are obtained thereby.

According to a preferred embodiment of the present invention, the drying of the moldings, respectively, is preferably followed by at least one calcination step. Calcination is carried out at temperatures in general in the range of from 350-750° C., preferably form 400-700° C., particularly preferably from 450-650° C. The calcination can be effected under any suitable gas atmosphere, wherein air and/or lean air are preferred. Furthermore, the calcination is preferably carried out in a muffle furnace, a rotary kiln and/or a belt calcining furnace, wherein the duration of calcination is in general 1 h or more, for example in the range of from 1 to 24 h or in the range of from 3 to 12 h. In the process according to the invention, it is accordingly possible, for example, to calcine the catalyst shaped body once, twice or more often for in each case at least 1 h, such as, for example, in each case in the range of from 3 to 12 h, wherein it is possible for the temperatures during a calcination step to remain constant or to be changed continuously or discontinuously. If calcination is effected twice or more often, the calcination temperatures in the individual steps may be different or identical.

According to a particularly preferred embodiment, the catalyst shaped body is subjected to a hydrothermal treatment. Hydrothermal treatment can be carried out employing any suitable method known to those skilled in the art. Thus, the catalyst or catalyst shaped in general is contacted with water or water vapor. Typically, said hydrothermal treatment is carried out by charging the catalyst or according to the invention together with water into an autoclave, heating the slurry to a temperature in the range of from 100 to 200° C., preferably in the range of from 120 to 150° C. at a pressure in the range of from 1.5 to 5 bar, preferably in the range of from 2 to 3 bar, for a period in the range of from 1 to 48 hours, preferably in the range of from 24 to 48 hours. Typically at least one washing step, preferably with water as wash substance, follows. After the treatment with water the catalyst is being preferably dried and/or calcined, wherein drying and calcination is carried out as already described above. According to a preferred embodiment, the hydrothermal treatment is carried out by stirring the catalyst shaped body in an autoclave, wherein the stirring rate is adjusted to a stirring rate such that to avoid attrition as far as possible. If the catalyst is used in form of cylindrical extrudates, however, some attrition is desired to achieve cylindrical extrudates having rounded edges. With such extrudates having rounded edges, a higher bulk density can be achieved, for example for the use of the extrudates as fixed-bed catalyst in a tube reactor R1 and/or in a shaft reactor R2. Furthermore, the dust formation of said catalysts in the epoxidation process in stages (i) and (iii) is reduced.

Further, in the epoxidation process of the present invention, a titanium silicalite-1 catalyst as described above is employed, having micropores and mesopores, comprising from 49.5 to 80%, preferably 69.5 to 80% by weight of titanium silicalite-1, based on the total weight of the catalyst, and from 19.5 to 50%, preferably from 19.5 to 30% by weight of at least one binder, preferably a silica binder, based on the total weight of the catalyst shaped body.

If TS-1 is used as catalytically active material according to the present invention, it is preferred that the organic solvent comprises, preferably essentially consists of methanol.

Therefore, the present invention preferably relates to a process for the regeneration of a catalyst comprising TS-1 as catalytically active material, said catalyst having been used in a process for the preparation of an olefin oxide comprising (i) providing a mixture comprising methanol, an olefin, an epoxidation agent and an at least partially dissolved potassium comprising salt;

(ii) subjecting the mixture provided in (i) in a reactor to epoxidation conditions in the presence of the catalyst, obtaining a mixture comprising methanol and the olefin oxide, and obtaining the catalyst having a potassium salt deposited thereon;

said process for the regeneration comprising (a) separating the mixture obtained from (ii) from the catalyst;

(b) washing the catalyst obtained from (a) with a liquid aqueous system;

(c) optionally drying the catalyst obtained from (b) in a gas stream comprising an inert gas at a temperature of less than 300° C.;

(d) calcining the catalyst obtained from (c) in a gas stream comprising oxygen at a temperature of at least 300° C.

Especially preferably, the present invention preferably relates to a process for the regeneration of a catalyst comprising TS-1 as catalytically active material, said catalyst having been used in a continuous process for the preparation of propylene oxide comprising (i) providing a mixture comprising methanol, propene, hydrogen peroxide, water, optionally propene, and an at least partially dissolved potassium comprising salt, wherein the potassium comprising salt is selected from the group consisting of dihydrogen phosphate, dipotassium hydrogen phosphate, potassium formate, and a mixture of two or more thereof;

(ii) subjecting the mixture provided in (i) in a reactor to epoxidation conditions in the presence of the catalyst, obtaining a mixture comprising methanol, the propylene oxide, water, optionally propene, optionally propane, and obtaining the catalyst having the potassium salt deposited thereon, wherein the mixture according to (i) contains the potassium comprising salt with a molar ratio of potassium comprised in the potassium comprising salt relative to hydrogen peroxide in the range of from $10 \times 10^{-6}:1$ to $1500 \times 10^{-6}:1$, preferably from $20 \times 10^{-6}:1$ to $1300 \times 10^{-6}:1$, more preferably from $30 \times 10^{-6}:1$ to $1000 \times 10^{-6}:1$, said process for the regeneration comprising (a) separating the mixture obtained from (ii) from the catalyst;
(b) washing the catalyst obtained from (a) with a liquid aqueous system which contains at least 99.9 weight-% water, more preferably at least 99.99 weight-% water, more preferably at least 99.999 weight-% water, based on the total weight of the liquid aqueous system, at a pressure in the range of from 0.8 to 1.5 bar, preferably from 1.0 to 1.4 bar, and a temperature in the range of from 40 to 90° C., preferably from 60 to 80° C.;
(c) optionally drying the catalyst obtained from (b) in a gas stream comprising an inert gas at a temperature in the range of from 25 to 100° C., preferably from 30 to 50° C.;
(d) calcining the catalyst obtained from (b) or (c), preferably (c), in a gas stream comprising oxygen employed in (d) contains oxygen in the range of from 3 to 40 volume-%, preferably from 5 to 50 volume-% based on the total volume of the gas stream at a temperature of at a temperature in the range of from 375 to 525° C., preferably from 400 to 500° C.

The Epoxidation Reaction

The reaction may be performed in a batch mode or a continuous mode, wherein the continuous mode is preferred. Conveniently, the reactor comprises the heterogeneous catalyst arranged therein and is equipped with means for controlling the reaction temperature, such as a cooling jacket.

Conveniently, the educt conversion rate may be controlled by adjusting temperature, pressure, WHSV of the educts, and the like. By way of example, the reaction temperature may be adjusted so that at least 90% of the epoxidation agent is converted. The amounts of educt present in the reaction mixture before and after the epoxidation reaction may be analyzed by any suitable technique, e.g. chromatography.

As it will explained more in detail further below, a gradual decrease in the activity of the catalyst comprising a titanium containing zeolite as catalytically active material may be compensated over a certain period of time by increasing the reaction temperature. The reaction temperature in (ii) is typically in the range of 20 to 50° C., depending of the momentary activity of the catalyst used.

Generally, the continuous epoxidation reaction in (ii) can be carried out in any appropriate way. Preferably, the reaction in (ii) is carried out in at least one continuously operated reactor such as a tube reactor or a tube bundle reactor which preferably contains at least one cooling jacket surrounding the at least one tube. If the reaction in (ii) is carried out in such a reactor containing at least one cooling jacket, the term "reaction temperature" as used herein refers to the temperature of the cooling medium when entering the cooling jacket.

The catalyst comprising the titanium zeolite can be employed in every conceivable form described hereinabove, including a powder, a micropowder, preferably a spray-powder, as a molding comprising a powder, or as a molding comprising micropowder, preferably a spray-powder. Preferably, the catalyst comprising the titanium zeolite of is employed as a molding comprising a powder or a micropowder, preferably a spray-powder, more preferably as a molding comprising a micropowder, preferably a spray-powder.

The catalyst used in step (ii) of the present invention can be arranged in the reactor in every conceivable manner. Preferably, the catalyst is arranged as fluidized bed or as fixed bed, more preferably as fixed bed.

As mentioned above, the liquid feed stream provided in (i) is passed into the reactor in (i) containing the catalyst preferably present as fixed bed. During the epoxidation reaction, the catalyst loading is preferably in in the range of from 0.05 to 1.25 $h^{-1}$, preferably from 0.1 to 1 $h^{-1}$, more preferably from 0.2 to 0.7 $h^{-1}$, wherein the catalyst loading is defined as the ratio of the mass flow rate in kg/h of epoxidation agent, preferably hydrogen peroxide, contained in liquid feed stream provided in (i) divided by the amount in kg of catalyst comprising a titanium zeolite comprised in the epoxidation reactor in (ii). The term "the epoxidation conditions comprise" as used in this context of the present invention relates to an epoxidation reaction in step (ii) wherein in at least 90%, preferably at least 95% of the catalyst bed in the reactor and during at least 90%, preferably at least 95% of the overall reaction time, the catalyst loading is in the above-defined ranges.

During the epoxidation reaction in (ii), the temperature of the reaction mixture in the reactor is preferably controlled, more preferably kept in preferred ranges. In order to control the temperature of the reaction mixture, internal and/or external temperature control means can be used. The term "intern temperature control means" as used in this context of the present invention relate to means which are arranged in the reactor. The term "external temperature control means" as used in this context of the present invention relate to means which are arranged outside the reactor. Preferably, the temperature of the reaction mixture is controlled by external temperature control means, more preferably via a heat transfer medium which is preferably passed through a suitable jacket, which jacket preferably surrounds the reactor. In case a tube-bundle reactor is used as reactor, the jacket preferably surrounds all tubes of the tube-bundle.

Preferably, during the epoxidation reaction in (ii), the reaction temperature is in the range of from 20 to 100° C., more preferably from 25 to 90° C., more preferably from 30 to 80° C., more preferably from 35 to 70° C., more preferably from 40 to 60° C. The term "reaction temperature" as used in this context of the present invention relates to the temperature of the heat transfer medium prior to controlling of the temperature of the reaction mixture, preferably to the temperature of the heat transfer medium at the entrance of the jacket of the epoxidation reactor, through which jacket the heat transfer medium is passed. Therefore, the present invention relates to the process as described above, wherein in (ii), the epoxidation conditions comprise, preferably consist of an epoxidation reaction temperature in the range of from 20 to 100° C., preferably from 30 to 80° C., more preferably from 40 to 60° C., wherein the epoxidation reaction temperature is defined as the temperature of the heat transfer medium prior to controlling of the temperature of the reaction mixture, preferably as the temperature of the heat transfer medium at the entrance of the jacket of the epoxidation reactor. The term "the epoxidation conditions comprise" as used in this context of the present invention relate to an epoxidation reaction in step (ii) wherein for at least 98%, preferably at least 99%, more preferably at least 99.9% of the overall reaction time, the reaction temperature is in the above-defined ranges. The term "overall reaction time" as used in this context of the present invention relates to the reaction time a given catalyst bed is used before it is either discarded or subjected to regeneration. In particular at the beginning of an epoxidation reaction in (ii) when the catalyst is fresh, i.e. at the start-up of the epoxidation reaction in (ii), the reaction temperature can be outside the above-mentioned ranges for a short period of time. Preferably, the flow rate of the heat transfer medium is chosen so that the temperature difference between its inlet temperature and its outlet temperature is at most 3 K, more preferably at most 2 K, more preferably at most 1 K.

Preferably, during the epoxidation reaction in (ii), the epoxidation reaction pressure is in the range of from 14 to 100 bar, more preferably from 14.5 to 50 bar, more preferably from 15 to 32 bar, more preferably from 15 to 25 bar. The term "epoxidation reaction pressure" as used in this context of the present invention relates to the pressure at the exit of the epoxidation reactor where the effluent is removed from the reactor according to (iii). Therefore, the present invention relates to the process as described above, wherein in (ii), the epoxidation conditions comprise, preferably consist of an epoxidation reaction pressure in the range of from 14 to 100 bar, preferably from 15 to 32 bar, more preferably from 15 to 25 bar. The term "the epoxidation conditions comprise" as used in this context of the present invention relate to an epoxidation reaction in step (ii) wherein for at least 98%, preferably at least 99%, more preferably at least 99.9% of the overall reaction time, the reaction temperature is in the above-defined ranges. The term "overall reaction time" as used in this context of the present invention relates to the reaction time a given catalyst bed is used before it is either discarded or subjected to regeneration.

Preferably, the epoxidation reaction according to step (ii) of the present invention is carried out at an essentially constant epoxidation agent conversion, preferably hydrogen peroxide conversion. Preferably, in order to determine the epoxidation agent conversion, preferably the hydrogen peroxide conversion, the molar flow rate of the epoxidation agent, preferably the hydrogen peroxide in the effluent stream removed in (iii), referred to herein as $m_{out}$, is compared with the molar flow rate of epoxidation agent, preferably hydrogen peroxide in the liquid feed stream provided in (i), referred to herein as $m_{in}$, and wherein the epoxidation agent conversion, preferably the hydrogen peroxide conversion is defined as $100 \times (1-m_{out}/m_{in})$. Preferably, the inlet temperature of the heat transfer medium described above is adjusted in the above-mentioned preferred ranges in order to keep the epoxidation agent conversion, preferably the hydrogen peroxide conversion essentially constant in the range of from 80 to 100%, more preferably from 90 to 100%, more preferably from 95 to 100%, more preferably from 99 to 100%, more preferably from 99.5 to 100%, more preferably from 99.9 to 100%. The term "the epoxidation conditions comprise" as used in this context of the present invention relate to an epoxidation reaction in step (ii) wherein for at least 98%, preferably at least 99%, more preferably at least 99.9% of the overall reaction time, the epoxidation agent conversion, preferably the hydrogen peroxide conversion is in the above-defined ranges. The term "overall reaction time" as used in this context of the present invention relates to the reaction time a given catalyst bed is used before it is either discarded or subjected to regeneration. In particular at the beginning of an epoxidation reaction in (ii) when the catalyst is fresh, i.e. at the start-up of the epoxidation reaction in (ii), the epoxidation agent conversion, preferably the hydrogen peroxide conversion can be outside the above-mentioned ranges for a short period of time. Preferably, the reaction temperature is not kept constant during the reaction but is adjusted continuously or step-wise to allow for a constant epoxidation agent conversion, preferably hydrogen peroxide conversion. Generally, due to a certain catalyst deactivation, the reaction temperature is continuously or step-wise increased. Preferably, the reaction temperature is continuously or step-wise increased by 1 K/d (Kelvin/day) at most, more preferably by less than 1 K/d.

Preferably, the reaction mixture which is present in the reactor in (ii) is liquid under the epoxidation conditions. Preferably, the reaction mixture consists of one single liquid phase, of two liquid phases, or of three or more liquid phases. Preferably, the reaction mixture in the reactor in (ii) consists of one single liquid phase or of two liquid phases, more preferably of one single liquid phase.

Generally, the reactor used in step (ii) of the present invention can be arranged horizontally or vertically. Preferably, the reactor is arranged vertically. In the preferably vertically arranged reactor, the liquid feed stream provided in (i) can be passed in up-flow mode or on down-flow mode, the up-flow mode being preferred. Preferably, compared with the direction of the flow of the liquid feed stream, the heat transfer medium is passed through the jacket in co-current mode.

Generally, the epoxidation reaction in (ii) can be carried out in one or more reactors wherein these reactors can be arranged in parallel or in series. Preferably, the reaction in (ii) is carried out in one reactor or in at least two reactors, preferably two reactors, which are arranged in series wherein between two reactors arranged in series, a suitable intermediate treatment can be carried out. If the reaction is carried out in two reactors arranged in series, it is preferred that the first reactor is operated as described above, i.e. as isothermal reactor, and the second reactor, i.e. the downstream reactor, is operated as adiabatic or essentially adiabatic reactor. The term "reactor" as used herein also encompasses two or more reactors arranged in parallel wherein a feed stream passed is divided in two or more sub-streams, each substream is passed into a reactor, and the effluent streams removed from the reactors are combined to obtain the overall effluent stream. Therefore, the epoxidation reaction can be carried out in at least one first reactor such as two or more first reactors, for example 2, 3, 4 first reactors, which are arranged in parallel and which are preferably isothermal reactors, and in at least one second reactor such as two or more second reactors, for example 2, 3, 4 second reactors, which are arranged in parallel and which are preferably adiabatic or essentially adiabatic reactors.

If the epoxidation reaction according to (ii) is carried out in two reactors arranged in series, it is preferred that in the first reactor which is preferably an isothermal reactor, the epoxidation agent conversion, preferably the hydrogen peroxide conversion is kept essentially constant in a range of from 80 to 99%, preferably from 85 to 98%, more preferably from 90 to 97%, and in the second reactor which is preferably designed as adiabatic or essentially adiabatic reactor, the overall epoxidation agent conversion, preferably the hydrogen peroxide conversion, i.e. the epoxidation agent conversion, preferably the hydrogen peroxide conversion taking into account the conversion in the first and the second reactor, is brought to a value of more than 99%, preferably at least 99.5%, more preferably at least 99.9%.

The Spent Catalyst

Typically, after a prolonged time period of use of a freshly produced catalyst comprising a titanium containing zeolite in a process for the preparation of an olefin oxide, a decrease of its catalytic activity is observed compared to freshly prepared catalyst. Such a gradual decrease of catalytic activity may be compensated to some extent by increasing the reaction temperature. The catalytic activity may be followed by determining the conversion rate of at least one educt in the course of the reaction at the given temperature. In case a drop of the conversion rate is observed during the process, the reaction temperature will be increased. Accordingly, the catalyst comprising a titanium containing zeolite may be subjected to regeneration when the reaction temperature has reached a set upper temperature limit, above which the process becomes environmentally and economical inefficient. For example, the catalyst comprising a titanium containing zeolite may be subjected to regeneration when the reaction temperature in (ii) required to maintain the conversion rate for one of the educts above e.g. 90%, is 70° C. or higher, preferably 60° C. or higher, more preferably 50° C. or higher.

In the alternative, a catalyst comprising a titanium containing zeolite having potassium deposited thereon following steps (i) and (ii), may be subjected to the regeneration according to steps (a) to (d), when its selectivity deviates by more than a certain percentage relative to the selectivity of fresh catalyst comprising a titanium containing zeolite. Here, the selectivity of the catalyst comprising a titanium containing zeolite is defined by the overall conversion of one educt divided by the conversion of said educt into the desired product. For example, a catalyst comprising a titanium containing zeolite may be submitted to regeneration following steps (i) and (ii), when its selectivity of the catalyst regarding olefin oxide determined in (ii) deviates by 2% or more from the respective selectivity of fresh catalyst comprising a titanium containing zeolite at otherwise identical reaction conditions.

According to the present invention, it was found that a catalyst comprising a titanium containing zeolite intended for regeneration which fulfilled one of the above described criteria following steps (i) and (ii) has typically a potassium content of above 0.5 weight-%, preferably in the range of 0.6 to 1.3 weight. Yet further, it was found that after one sequence of steps (a) to (d) according to the present invention, the regenerated catalyst comprising a titanium containing zeolite obtained from (d) has a potassium content of at most 0.5 weight-%, preferably at most 0.4 weight-%, more preferably at most 0.3 weight-%, based on the total weight of the catalyst and determined via elemental analysis.

The regenerated catalyst obtained according to the process of the present invention can be employed for every use. Preferably, the catalyst comprising a titanium containing zeolite obtained from (d) is employed in a process for the preparation of an olefin oxide, preferably in an olefin epoxidation process comprising (i') providing a mixture comprising an organic solvent, an olefin, an epoxidation agent and a phosphate containing compound;

(ii') subjecting the mixture provided in (i') in a reactor to epoxidation conditions in the presence of the catalyst obtained from (d), obtaining a mixture comprising the organic solvent and the olefin oxide.

The preferred embodiments of steps (i') and (ii') are carried out as described in detail for steps (i) and (ii) above.

The present invention further relates to a catalyst comprising a titanium containing zeolite as catalytically active material, obtainable or obtained by the regeneration process of the present invention.

It is preferred that the catalyst regenerated according to the present invention exhibits in the process for the preparation of an olefin oxide, a differential conversion temperature of at most 5 K, wherein the differential conversion temperature is defined as the absolute difference between (A1) the temperature at which a pre-determined conversion of the epoxidation agent is achieved in said process for the preparation of an olefin oxide in which the regenerated catalyst is used as catalyst, and (B1) the temperature at which said pre-determined conversion of the epoxidation agent is achieved in said process for the preparation of an olefin oxide in which the respective fresh catalyst is used as catalyst under otherwise identical epoxidation reaction conditions.

It has already been indicated that after a certain operation time a decrease in the catalytic activity of a catalyst comprising a titanium containing zeolite as catalytically active material is observed in an epoxidation reaction. The reduced catalytic activity is directly related to a reduced conversion rate for at least one of the educts, i.e. the olefin and/or the epoxidation agent, wherein the reduced conversion rate may be compensated by increasing the overall reaction temperature. This implies that with continued operation of the catalyst a gradual increase of the reaction temperature is required relative to the starting temperature, making the epoxidation process increasingly ineffective.

However, by subjecting a catalyst comprising a titanium containing zeolite spent in an epoxidation reaction to the regeneration process of the present invention, its initial catalytic activity may be restored. The initial catalytic activity refers here the catalytic activity of freshly prepared catalyst. Since the catalytic activity is conveniently directly related to the reaction temperature under otherwise identical reaction conditions, the efficiency of a regeneration of a spent catalyst may be deduced from the reaction temperature required to maintain a set conversion rate. In the present case, the catalyst regenerated according to the present invention favorably exhibits in the process for the preparation of an olefin oxide, a conversion temperature which deviates by at most 5 K from the conversion temperature of fresh catalyst under otherwise identical epoxidation conditions.

It is further preferred that the catalyst regenerated according to the process of the present invention exhibits in the process for the preparation of an olefin oxide, a differential selectivity of at most 2, wherein the differential selectivity is defined as the absolute difference in % between (A2) the selectivity based on the epoxidation agent in said process for the preparation of an olefin oxide in which the regenerated catalyst is used as catalyst, and (B2) the selectivity based on the epoxidation agent in said process for the preparation of an olefin oxide in which the respective fresh catalyst is used as catalyst under otherwise identical epoxidation reaction conditions, wherein the selectivity based on the epoxidation agent is defined as moles of epoxide produced divided by moles of epoxidation agent consumed×100.

The quality of the catalyst comprising a titanium containing zeolite regenerated according to the process of the present invention may also be quantified by comparing the selectivity of the regenerated catalyst with the selectivity of fresh catalyst under otherwise identical epoxidation conditions. Following a prolonged use also a decrease of the selectivity of the catalyst is typically observed. Favorably, in the present case, after having been submitted to the regeneration process of the present invention, a catalyst comprising a titanium containing zeolite has a selectivity which deviates by at most 2 percentage points from the selectivity of fresh catalyst under otherwise identical epoxidation reaction conditions.

Figure 1:
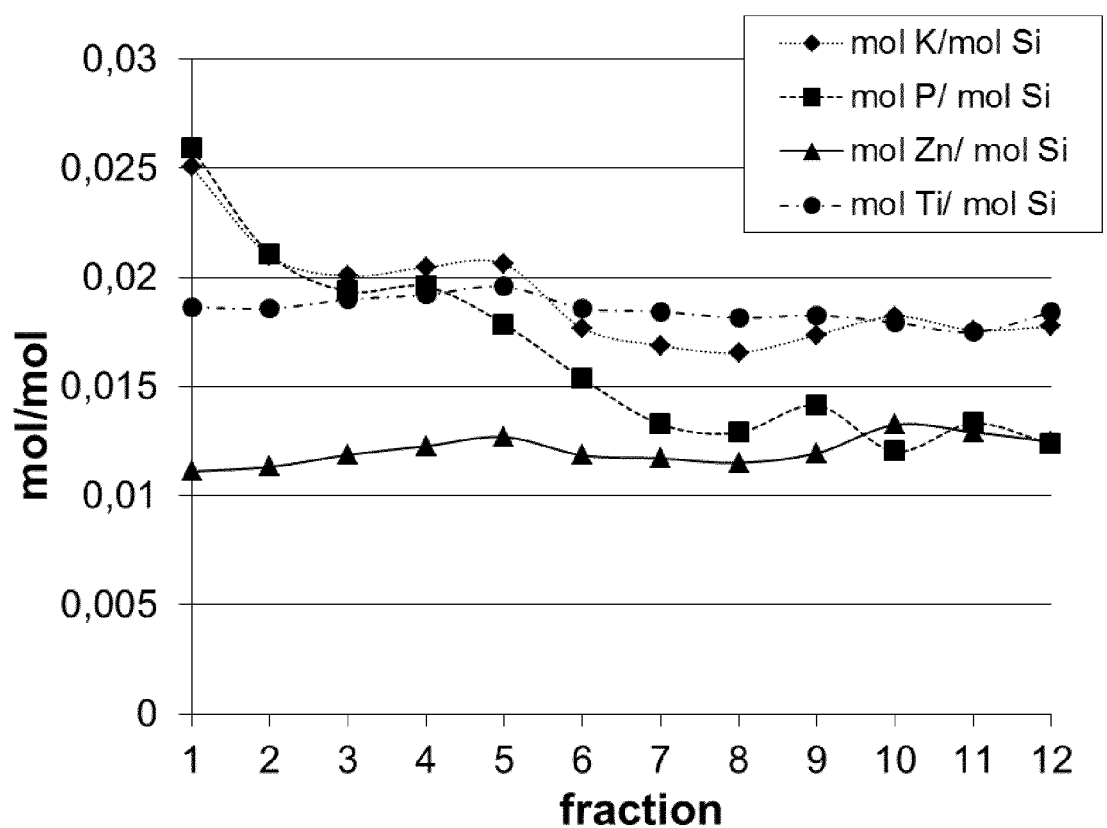
FIG. 1 shows the amount of potassium and phosphor deposited on the spent catalyst relative to the overall silicon content. Fraction 1 is a sample taken from the first meter at the bottom of a reactor tube, fraction 2 is a sample taken 1 to 2 m away from the bottom of a reactor tube and fraction 3 is a sample taken 2 to 3 m away from the bottom of a reactor tube.

The present invention is further illustrated by the following reference examples, examples, and reference examples.

EXAMPLES

Reference Example 1

Preparation of a Catalyst Comprising a Titanium Containing Zeolite (ZnTiMWW);

1.1 Preparation of Boron-Containing MWW 470.4 kg de-ionized water were provided in a vessel. Under stirring at 70 rpm (rounds per minute), 162.5 kg boric acid were suspended in the water. The suspension was stirred for another 3 h. Subsequently, 272.5 kg piperidine were added, and the mixture was stirred for another hour. To the resulting solution, 392.0 kg Ludox® AS-40 were added, and the resulting mixture was stirred at 70 rpm for another hour. The finally obtained mixture was transferred to a crystallization vessel and heated to 170° C. within 5 h under autogenous pressure and under stirring (50 rpm). The temperature of 170° C. was kept essentially constant for 120 h; during these 120 h, the mixture was stirred at 50 rpm. Subsequently, the mixture was cooled to a temperature of from 50-60° C. within 5 h. The aqueous suspension containing B-MWW had a pH of 11.3 as determined via measurement with a pH electrode. From said suspension, the B-MWW was separated by filtration. The filter cake was then washed with de-ionized water until the washing water had a conductivity of less than 700 microSiemens/cm. The thus obtained filter cake was subjected to spray-drying in a spray-tower using technical nitrogen as drying gas. The spray-dried material was then subjected to calcination at 650° C. for 2 h. The calcined material had a boron (B) content of 1.9 wt. %, a silicon (Si) content of 41 wt. %, and a total organic carbon (TOC) content of 0.18 wt. %.

1.2 Preparation of Deboronated MWW

Based on the spray-dried material obtained according to section 1.1 above, 4 batches of deboronated zeolite MWW were prepared. In each of the first 3 batches, 35 kg of the spray-dried material obtained according to section 1.1 and 525 kg water were employed. In the fourth batch, 32 kg of the spray-dried material obtained according to section 1.1 and 480 kg water were employed. In total, 137 kg of the spray-dried material obtained according to section 1.1 and 2025 kg water were employed. For each batch, the respective amount of water was passed into a vessel equipped with a reflux condenser. Under stirring at 40 r.p.m., the given amount of the spray-dried material was suspended into the water. Subsequently, the vessel was closed and the reflux condenser put into operation. The stirring rate was increased to 70 r.p.m. Under stirring at 70 r.p.m., the content of the vessel was heated to 100° C. within 10 h and kept at this temperature for 10 h. Then, the content of the vessel was cooled to a temperature of less than 50° C. The resulting deboronated zeolitic material of structure type MWW was separated from the suspension by filtration under a nitrogen pressure of 2.5 bar and washed four times with deionized water. After the filtration, the filter cake was dried in a nitrogen stream for 6 h. The deboronated zeolitic material obtained in 4 batches (625,1 kg nitrogen-dried filter cake in total) had a residual moisture content of 79%, as determined using an IR (infrared) scale at 160° C. From the nitrogen-dried filter cake having a residual moisture content of 79% obtained above, an aqueous suspension was prepared with deionized water, the suspension having a solid content of 15 wt.-%. This suspension was subjected to spray-drying in a spray-tower using technical nitrogen as drying gas. The spray-dried MWW material obtained had a B content of 0.08 wt. %, an Si content of 42 wt. %, and a TOC of 0.23 wt. %.

1.3 Preparation of TiMWW

Based on the deboronated MWW material as obtained according to section 1.2, a zeolitic material of structure type MWW containing titanium (Ti) was prepared, referred to in the following as TiMWW. 54.16 kg of the deboronated zeolitic material of structure type MWW were transferred in to a first vessel A. In a second vessel B, 200.00 kg deionized water were transferred and stirred at 80 r.p.m. 118.00 kg piperidine were added under stirring, and during addition, the temperature of the mixture increased for about 15° C. Subsequently, 10.90 kg tetrabutylorthotitanate and 20.00 kg deionized water were added. Stirring was then continued for 60 min. The mixture of vessel B was then transferred into vessel A, and stirring in vessel A was started (70 r.p.m.). 24.00 kg deionized water were filled into vessel A and transferred to vessel B. The mixture in vessel B was then stirred for 60 min. at 70 r.p.m. At the beginning of the stirring, the pH of the mixture in vessel B was 12.6, as determined with a pH electrode. After said stirring at 70 r.p.m., the frequency was decreased to 50 r.p.m., and the mixture in vessel B was heated to a temperature of 170° C.

within 5 h. At a constant stirring rate of 50 r.p.m., the temperature of the mixture in vessel B was kept at an essentially constant temperature of 170° C. for 120 h under autogenous pressure. During this crystallization of TiMWW, a pressure increase of up to 10.6 bar was observed. Subsequently, the obtained suspension containing TiMWW having a pH of 12.6 was cooled within 5 h. The cooled suspension was subjected to filtration, and the separated mother liquor was transferred to waste water discharge. The filter cake was washed four times with deionized water under a nitrogen pressure of 2.5 bar. After the last washing step, the filter cake was dried in a nitrogen stream for 6 h. From 246 kg of said filter cake, an aqueous suspension was prepared with deionized water, the suspension having a solid content of 15 wt.-%. This suspension was subjected to spray-drying in a spray-tower using technical nitrogen as drying gas. The spray-dried TiMWW material obtained from the first experiment had a Si content of 37 wt. %, a Ti content of 2.4 wt.-%, and a TOC of 7.5 wt. %.

1.4 Acid Treatment of TiMWW

The spray-dried TiMWW material as obtained in section 1.3 above was subjected to acid treatment, followed by spray-drying and calcining as described below. 670.0 kg deionized water were filled in a vessel. 900 kg nitric acid were added, and 53.0 kg of the spray-dried TiMWW were added under stirring at 50 r.p.m. The resulting mixture was stirred for another 1 5 min. Subsequently, the stirring rate was increased to 70 r.p.m. Within 1 h, the mixture in the vessel was heated to 100° C. and kept at this temperature and under autogenous pressure for 20 h under stirring. The thus obtained mixture was then cooled within 2 h to a temperature of less than 50° C. The cooled mixture was subjected to filtration, and the filter cake was washed six times with deionized water under a nitrogen pressure of 2.5 bar. After the last washing step, the filter cake was dried in a nitrogen stream for 10 h. The washing water after the sixth washing step had a pH of about 2.7. 225.8 kg dried filter cake were obtained. From the filter cake obtained, an aqueous suspension was prepared with deionized water, the suspension having a solid content of 15 wt.-%. This suspension was subjected to spray-drying in a spray-tower using technical nitrogen as drying gas. The spray-dried acid-treated TiMWW material had a Si content of 42 wt. %, a Ti content of 1.6 wt.-%, and a TOC of 1.7 wt. %. The spray-dried material was then subjected to calcination at 650° C. in a rotary furnace for 2 h. The calcined material had a Si content of 42.5 wt. %, a Ti content of 1.6 wt.-% and a TOC content of 0.15 wt. %. The Langmuir surface are determined via nitrogen adsorption at 77 K according to DIN 66131 was 612 m$^2$/g, the multipoint BET specific surface area determined via nitrogen adsorption at 77 K according to DIN 66131 was 442 m$^2$/g. The total intrusion volume determined according to Hg porosimetry according to DIN 66133 was 4.9 ml/g (milliliter/gram), the respective total pore area 104.6 m$^2$/g. The degree of crystallization determined via XRD was 80%, the average crystallite size 31 nm.

1.5 Impregnation of TiMWW with Zn

The acid-treated, spray-dried and calcined material as obtained according to 1.4 was then subjected to an impregnation stage. Impregnation was carried out in 3 batches a) to c) as follows:

a) In a vessel equipped with a reflux condenser, a solution of 840 kg deionized water and 5.13 kg zinc acetate dihydrate was prepared within 30 min. Under stirring (40 r.p.m.), 28 kg of the calcined Ti-MWW material obtained according to 1.4 were suspended. Subsequently, the vessel was closed and the reflux condenser put into operation. The stirring rate was increased to 70 r.p.m.

b) In a vessel equipped with a reflux condenser, a solution of 840 kg deionized water and 5.13 kg zinc acetate dihydrate was prepared within 30 min. Under stirring (40 r.p.m.), 28 kg of the calcined Ti-MWW material obtained according to 1.4 were suspended. Subsequently, the vessel was closed and the reflux condenser put into operation. The stirring rate was increased to 70 r.p.m.

c) In a vessel equipped with a reflux condenser, a solution of 930 kg deionized water and 5.67 kg zinc acetate dihydrate was prepared within 30 min. Under stirring (40 r.p.m.), 31 kg of the calcined Ti-MWW material obtained according to 1.4 were suspended. Subsequently, the vessel was closed and the reflux condenser put into operation. The stirring rate was increased to 70 r.p.m.

In all batches a) to c), the mixture in the vessel was heated to 100° C. within 1 h and kept under reflux for 4 h at a stirring rate of 70 r.p.m. Then, the mixture was cooled within 2 h to a temperature of less than 50° C. For each batch a) to c), the cooled suspension was subjected to filtration, and the mother liquor was transferred to waste water discharge. The filter cake was washed five times with deionized water under a nitrogen pressure of 2.5 bar. After the last washing step, the filter cake was dried in a nitrogen stream for 10 h. For batch a), 106.5 kg nitrogen-dried filter cake were finally obtained. For batch b), 107.0 kg nitrogen-dried filter cake were finally obtained. For batch c), 133.6 kg nitrogen-dried filter cake were finally obtained. The thus dried Zn-impregnated TiMWW material (ZnTiMWW), for each batch, had a Si content of 42 wt. %, a Ti content of 1.6 wt.-%, a Zn content of 1.4 wt. % and a TOC of 1.4 wt. %.

1.6 Preparation of a Molding

Starting from the calcined spray-dried ZnTiMWW material obtained above, a molding was prepared, dried, and calcined. Therefor, 22 batches were prepared, each starting from 3.4 kg of the calcined spray-dried ZnTiMWW material obtained in Example 1, 0.220 kg Walocel™ (Walocel MW 15000 GB, Wolff Cellulosics GmbH & Co. KG, Germany), 2.125 kg Ludox® AS-40 and 6.6 l deionized water, as follows: 3.4 kg ZnTiMWW and 0.220 kg Walocel were subjected to kneading in an edge mill for 5 min. Then, during further kneading, 2.125 kg Ludox were added continuously. After another 10 min, addition of 6 l of deionized water was started. After another 30 min, further 0.6 l of deionized water were added. After a total time of 50 min, the kneaded mass had become extrudable. Thereafter, the kneaded mass was subjected to extrusion under 65-80 bar wherein the extruder was cooled with water during the extrusion process. Per batch, the extrusion time was in the range of from 15 to 20 min. The power consumption per batch during extrusion was 2.4 A. A die head was employed allowing for producing cylindrical strands having a diameter of 1.7 mm. At the die head out outlet, the strands were not subjected to a cutting to length. The strands thus obtained were dried for 16 h at 120° C. in a drying chamber under air. In total (sum of the 22 batches), 97.1 kg white strands with a diameter of 1.7 mm were obtained. 65.5 kg of the dried strands were subjected to calcination in a rotary furnace at 550° C. for 1 h under air, yielding 62.2 kg calcined strands. Thereafter, the strands were sieved (mesh size 1.5 mm), and the yield, after sieving, was 57.7 kg.

Characterization of the Strands Obtained:

The thus obtained moldings exhibited a bulk density of 322 g/l (gram per liter) and had a Zn content of 1.2 wt. %, a Ti content of 1.4 wt. %, a Si content of 43 wt. %, and a C content of 0.13 wt. %. The sodium (Na) content was 0.07 wt. %. The mesopores of the micropowder had an average pore diameter (4V/A) of 20.1 nm as determined by Hg porosimetry according to DIN 66133. The macropores of the micropowder had an average pore diameter (4V/A) of 46.8 nm as determined by Hg porosimetry according to DIN 66133. The degree of crystallization determined via XRD was 74+/−%, the average crystallite size 38.0 nm+/−10%. The Langmuir surface are determined via nitrogen adsorption at 77 K according to DIN 66131 was 499 m$^2$/g, the mulitpoint BET specific surface area determined via nitrogen adsorption at 77 K according to DIN 66131 was 361 m$^2$/g. The total intrusion volume (please explain) determined according to Hg porosimetry according to DIN 66133 was 1.2 ml/g (milliliter/gram), the respective total pore area 92.2 m$^2$/g.

1.7 Post-Treatment of the Molding

Starting from the calcined strands obtained according to section 1.6, a post-treatment stage was performed as follows: 590 kg deioinized water were filled in a vessel. Then, 29.5 kg of the calcined moldings obtained according to Example 2 were added. The vessel was closed (pressure-tight), and the obtained mixture was heated to a temperature of 145° C. within 1.5 h and kept at this temperature under autogenous pressure (about 3 bar) for 8 h. Then, the mixture was cooled for 2 h. The water-treated strands were subjected to filtration and washed with deionized water. The obtained strands were heated in a drying chamber under air within 1 h to a temperature of 120° C. and kept at this temperature for 16 h. Subsequently, the dried material was heated under air to a temperature of 450° C. within 5.5 h and kept at this temperature for 2 h. Thereafter, the strands were sieved (mesh size 1.5 mm), and the yield, after sieving, was 27.5 kg.

Characterization of the Strands Obtained:

The thus obtained water-treated moldings exhibited a bulk density of 340 g/l (gram per liter) and had a Zn content of 1.3 wt. %, a Ti content of 1.4 wt. %, a Si content of 43 wt. %, and a C content of 0.10 wt. %. The mesopores of the micropowder had an average pore diameter (4V/A) of 20.2 nm as determined by Hg porosimetry according to DIN 66133. Thus, the inventive water treatment has practically no influence on the mesopore characteristics of the molding (cf. the molding as described above, having a respective average pore diameter of 20.1 nm). The macropores of the micropowder had an average pore diameter (4V/A) of 45.9 nm as determined by Hg porosimetry according to DIN 66133.Thus, the inventive water treatment has practically no influence on the macropore characteristics of the molding (cf. the molding as described above, having a respective average pore diameter of 46.8 nm). The degree of crystallization determined via XRD was 64%+/−10%, the average crystallite size 39.4 nm+/−10%. The Langmuir surface are determined via nitrogen adsorption at 77 K according to DIN 66131 was 418.1 m$^2$/g, the multipoint BET specific surface area determined via nitrogen adsorption at 77 K according t DIN 66131 was 299.8 m$^2$/g. The total intrusion volume determined according to Hg porosimetry according to DIN 66133 was 1.1322 ml/g (milliliter/gram), the respective total pore area 92.703 m$^2$/g.

Reference Example 2

Production of Propylene Oxide at Large Scale Using the ZnTiMWW Catalyst

An epoxidation of propene to propylene oxide using the ZnTiMWW catalyst obtained as described in Reference Example 1 was carried as described in Reference Example 3. The aqueous hydrogen peroxide feed was admixed with 390 micromol K$_2$PO$_4$ additive per 1 mol H$_2$O$_2$ to the stream (3). The reaction was further carried out under the condition that the conversion rate of hydrogen peroxide was at least 91% at all times, which required the reaction temperature to be gradually increased.

Here, to compensate for the activity loss of the ZnTiMWW catalyst the initial water cooling temperature, i.e. the reaction temperature, of 30° C. was gradually increased to 55° C. while performing the reaction. The epoxidation was carried out for 2100 hours in total.

After 2100 hours the ZnTiMWW catalyst was removed from the reactor tubes and 12 samples were taken for elemental analysis. A sample was taken of the catalyst located in every meter of the reactor.

Figure 2:
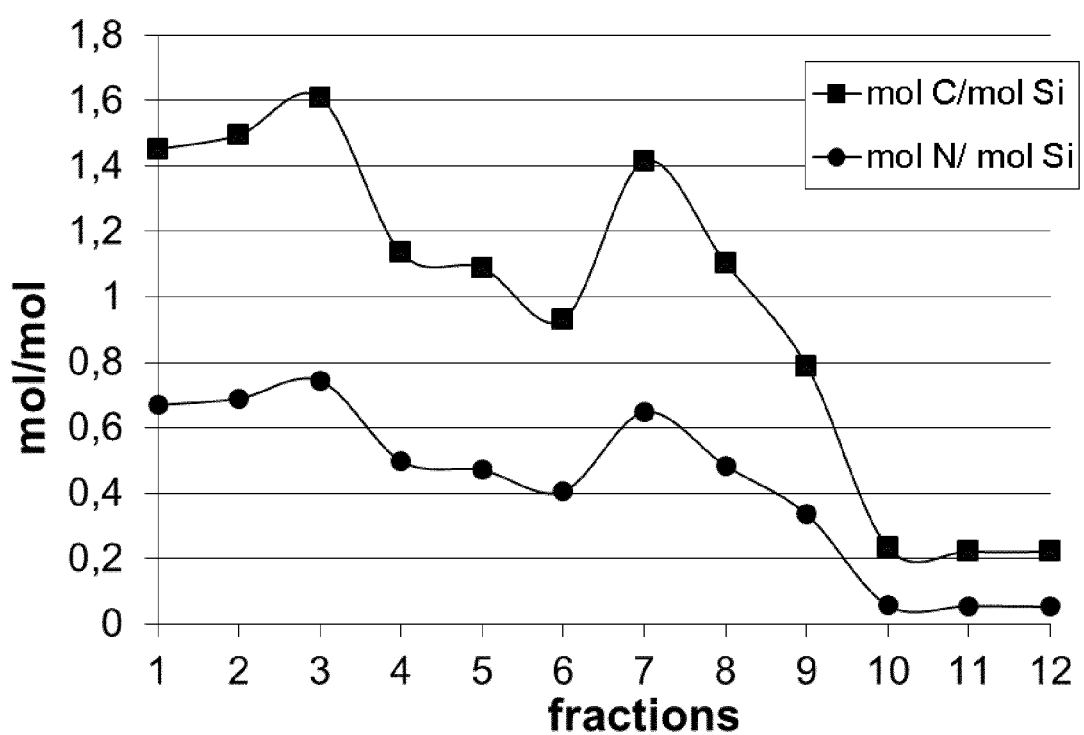
FIG. 2 shows the amount of carbon and nitrogen deposited on the spent catalyst relative to the overall silicon content. Fraction 1 is a sample taken from the first meter at the bottom of a reactor tube, fraction 2 is a sample taken 1 to 2 m away from the bottom of a reactor tube and fraction 3 is a sample taken 2 to 3 m away from the bottom of a reactor tube.

Samples 1 to 12 were analyzed using the Inductively Coupled Plasma (ICP) technique. FIG. 1 shows the amounts of potassium and phosphor deposited on the spent catalyst plotted as molar ratios relative to the silicon content, the latter which essentially does not change in the course of the reaction. This corresponds to approx. 0.5 to 2 weight-% potassium and approx. 0.5 to 2 weight-% phosphor relative to the total amount of catalyst. FIG. 2 shows the amounts of carbon and nitrogen deposited on the spent catalyst plotted as molar ratios relative to the silicon content.

Reference Example 3

Epoxidation Reaction Setup (Large-Scale)

According to a large-scale setup, the epoxidation reaction was carried out as follows:

a) Epoxidation in an Epoxidation Main Reactor (Epoxidation Unit A)

The main reactor A was a vertically mounted tube-bundle reactor with 5 tubes (length of the tubes: 12 m, internal tube diameter: 38 mm), each tube being equipped with an axially placed multi-point thermocouple with 10 equally spaced measuring points encased in a suitable thermowell with a diameter of 18 mm. Each tube was charged with 17.5 kg of the ZnTiMWW catalyst moldings as prepared according to Reference Example 1, section 1.7 (post-treated moldings). Free space eventually remaining was filled with steatite spheres (diameter of 3 mm). The heat of reaction was removed by circulating a thermostatized heat transfer medium (water/glycol mixture) on the shell side in co-current to the feed. The flow rate of the heat transfer medium was adjusted so that the temperature difference between entrance and exit did not exceed 1° C. The reaction temperature referred to herein-below was defined as the temperature of the heat transfer medium entering the reactor shell. At the reactor exit, the pressure was controlled by a pressure regulator and kept constant at 20 bar.

The reactor was fed from below with a liquid monophasic stream (1). Stream 1 was prepared by mixing three streams (2), (3), and (4). The temperature of stream (1) was not actively controlled, but was usually in the range from 20 to 40° C.:

Stream (2) having a flow rate of 85 kg/h. At least 99.5 weight-% of stream (2) consisted of acetonitrile, propene and water. This stream (2) came from the bottoms of the acetonitrile recycle distillation unit (J).

Stream (3) having a flow rate of 15 kg/h was an aqueous hydrogen peroxide solution having a hydrogen peroxide concentration of 40 weight-% ("crude/washed" grade from Solvay with a TOC in the range of 100 to 400 mg/kg. The aqueous hydrogen peroxide solution was supplied from a storage tank, allowing for a continuous feeding, and fed using a suitable metering pump.

Stream (4) was a make-up stream of pure acetonitrile (chemical grade, from Ineos, purity about 99.9%, containing between 70-180 weight-ppm propionitrile, 5-20 weight-ppm acetamide and less than 100 weight-ppm water as impurities). Enough fresh acetonitrile was added to compensate for losses in the process. Under regular conditions, an average of from 100 to 150 g/h of make-up acetonitrile were added.

The output stream leaving the epoxidation unit A was sampled every 20 minutes in order to determine the hydrogen peroxide concentration using the titanyl sulfate method and to calculate the hydrogen peroxide conversion. The hydrogen peroxide conversion was defined as $100 \times (1-m_{out}/m_{in})$ wherein $m_{in}$ is the molar flow rate of $H_2O_2$ in the reactor feed and $m_{out}$ is the molar flow rate of $H_2O_2$ in the reactor outlet. Based on the respectively obtained hydrogen peroxide conversion values, the inlet temperature of the heat transfer medium was adjusted in order to keep the hydrogen peroxide conversion essentially constant in the range of from 90 to 92%. The inlet temperature of the heat transfer medium was set at 30° C. at the start of a given run with a fresh batch of the epoxidation catalyst and was increased, if necessary, to maintain the hydrogen peroxide conversion in the mentioned range. The required temperature increase was usually less than 1° C./d.

b) Intermediate Removal of Propylene Oxide (Distillation Unit B)

After pressure release, the effluent from the epoxidation unit A (stream (5)) was sent to an intermediate propylene oxide removing column (distillation unit B) operated at about 1.1 bar. The column was 6 m high, had a diameter of 200 mm and was equipped with 30 bubble trays, an evaporator, and a condenser. The feed to the column entered above bubble tray 25 (counted from the top). The overhead stream leaving the column with about 50° C. mainly contained propylene oxide, unconverted propene and small amounts of oxygen formed as byproduct. This stream was partly condensed (T=15-25° C.), and the condensed liquid served as an internal reflux stream whereas the gaseous part (stream (6)) was sent to the lights separation column (distillation unit D).

The bottoms temperature of the intermediate propylene oxide removal column was about 80° C. The bottoms stream (stream (7)) was almost free of propylene oxide (<300 wt.-ppm) and was a mixture of acetonitrile (about 78-80 weight-%), water (about 18-20 weight-%), unconverted hydrogen epoxide and heavy boilers having a normal boiling point of above 100° C., the main heavy boiler being propene glycol. This bottoms stream (7) was subsequently cooled to 35° C. and pumped pump to the finishing reactor (epoxidation unit C; see section c) below) using a suitable metering pump.

c) Epoxidation in a Finishing Reactor (Epoxidation Unit C)

The total feed stream to the finishing reactor C was obtained by mixing stream (7) obtained according to section b) above with a stream (8) of polymer grade liquid propene containing propane (purity≥about 99.5%, feed rate: 0.9 kg/h, at ambient temperature). Both streams (7) and (8) were mixed using a static mixer and fed to the bottom of the finishing reactor C.

The finishing reactor C was a fixed bed reactor operated adiabatically. In this context, the term "adiabatic" refers to an operation mode according to which no active cooling is carried out and according to which the finishing reactor is suitably insulated in order to minimize heat losses). The finishing reactor C had a length of 4 m and a diameter of 100 mm. The reactor was filled with 9 kg of the same epoxidation catalyst which was used in the main epoxidation reactor A. Spare space was filled with steatite spheres (diameter of 3 mm). The operating pressure of the finishing reactor C was 10 bar which was kept constant by a suitable pressure regulator at the reactor exit. The output of the finishing reactor C was sampled every 20 min in order to determine the hydrogen peroxide concentration using the titanyl sulfate method.

The effluent of the finishing reactor C, stream (9), was depressurized into a flash drum, and both the liquid and the gas from this drum were fed to a light boiler separation column (distillation unit D).

The stream (6) obtained from the top of the intermediate propylene oxide removing column (distillation unit B) and the stream (9) obtained as effluent from the finishing reactor C (epoxidation unit C) together constitute the effluent stream of the epoxidation reaction.

Reference Example 4

Epoxidation Reaction Setup (Micro-Plant)

A tubular reactor (length: 1.4 m, internal diameter: 7 mm) equipped with a jacket for thermostatization was charged with 15 g of the desired catalyst in the form of strands with a diameter of 1.5 mm as described in the examples below. The remaining reactor volume was filled with inert material (steatite spheres, 2 mm in diameter, to a height of ca. 5 cm at the lower end of the reactor and the remainder at the top end of the reactor). The reactor was thermostatized by flowing a heat transfer medium (a mixture of water and ethylene glycol) through the jacket. The heat transfer medium is fed at the lower end of the jacket so that it flows in cocurrent to the reactor contents. The temperature of the heat transfer medium at the entrance of the jacket is defined as being the reaction temperature. The flow rate of the heat transfer medium is adjusted so that the difference between entrance and exit temperature is not more than 1° C. Pressure in the reactor is controlled by a suitable pressure control valve and maintained constant at 20 bar (abs).

The reactor feed stream is combined from three separate feed streams, that are metered by using separate metering pumps. The first stream consists of acetonitrile (flow rate: 68 g/h). The second stream consists of liquefied polymer grade propylene (flow rate: 11 g/h) and the third stream consists of an aqueous hydrogen peroxide solution with a concentration of 40 wt.-% (flow rate: 17 g/h). The potassium salt additive used in the experiments was dissolved in the hydrogen peroxide solution. The three feed streams were premixed before they were fed at ambient temperature to the bottom of the tubular reactor. Under the conditions used the feed is liquid and only one liquid phase is present.

The experiments were performed in a continuous manner. At the start of the run (t=0 is defined at which the $H_2O_2$ metering pump is started) the reaction temperature was set to 30° C. With a fresh catalyst this results initially in a 100% conversion of hydrogen peroxide. After a certain period of time (usually within 100 hours on stream) the hydrogen peroxide conversion starts to fall. The temperature is then adjusted (usually once to twice a day is sufficient) in order to keep the hydrogen peroxide conversion between 85 and 95%. During most of the time on stream the conversion remains between 88 and 92%. The reactor effluent after the pressure control valve was collected, weighed and analyzed.

Organic components (with the exception of hydroperoxypropanols) and $O_2$ were analyzed in two separate gas-chromatographs. The hydrogen peroxide was determined colorimetrically using the titanyl sulfate method. The content of hydroperoxypropanols (a mixture of 1-hydroperoxypropanol-2 and 2-hydroperoxypropanol-1) was determined by measuring the total peroxide content (iodometrically) and then subtracting the hydrogen peroxide content. Additionally the hydroperoxypropanol concentration can also be cross checked by determining the amount of propylene glycol before and after reduction with an excess of triphenylphosphane. The difference between the two values gives the amount of hydroperoxypropanols present in the unreduced sample.

The selectivity for propylene oxide given is relative to $H_2O_2$ and was calculated as 100 times the ratio of moles of propylene oxide in the reactor effluent divided by the sum of moles of propylene oxide plus propylene glycol plus twice the moles of hydroperoxypropanols and twice the moles of $O_2$ (the factor two reflects the stoichiometry of the reactions leading to these products: $2\ H_2O_2 \rightarrow 2H_2O+O_2$ and Propylene$+2\ H_2O_2 \rightarrow$hydroperoxypropanol$+H_2O$).

Comparative Example 1

Conventional Regeneration of the Zn TiMWW Catalyst

Spent ZnTi-MWW catalyst of fractions 1 to 3 of Reference Example 2 was regenerated by submitting to a thermal treatment. Specifically, 30 g of the spent catalyst were transferred into an oven. The ZnTiMWW catalyst was contacted with nitrogen at a temperature of 120° C. to remove volatile reaction compounds after which the ZnTiMWW catalyst was calcinated in an oven in air at 450° C. for 5 hours.

Comparative Example 2

Catalytic Performance of Conventionally Regenerated ZnTiMWW Catalyst

Following the regeneration according to Comparative Example 1, the catalytic performance of the regeneration ZnTiMWW catalyst was compared with the catalytic performance of fresh ZnTiMWW catalyst.

Two separate epoxidation reactions were performed according to the setup as described in Reference Example 3 using 15 g fresh ZnTiMWW catalyst and with 15 g conventionally regenerated ZnTiMMW catalyst, respectively, at otherwise identical reaction conditions.

The epoxidation using fresh ZnTiMWW catalyst was terminated after 405 hours, whereas the epoxidation using the conventionally regenerated ZnTiMWW catalyst was terminated after 500 hours. The reaction temperatures (i.e. cooling water temperatures) were adjusted in each experiment so that at all times the conversion rate of hydrogen peroxide was at least 91%.

Figure 3:
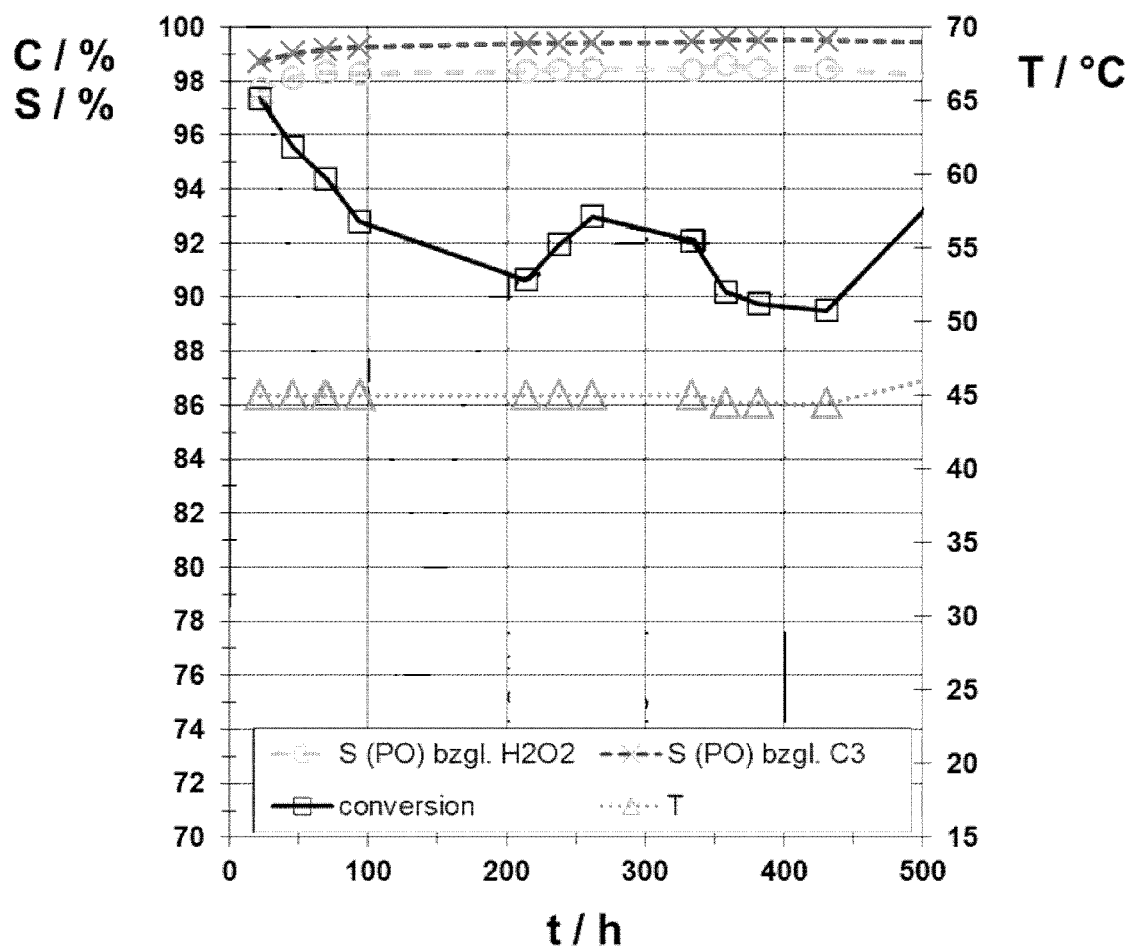
FIG. 3 shows the catalytic performance of spent catalyst regenerated according to a method of the prior art compared with the catalytic performance of fresh catalyst under otherwise identical epoxidation conditions. Indicated are the conversion rate based on hydrogen peroxide, the normalized selectivities based on hydrogen peroxide and propene of the spent catalyst and the fresh catalyst and further the reaction temperature (° C.) of the spent catalyst as well as the fresh catalyst.

In FIG. 3, the selectivity based on hydrogen peroxide, the selectivity based on propene (C3), the conversion rate based on hydrogen peroxide and the reaction temperature required to maintain a conversion rate for hydrogen peroxide of at least 91% of the fresh ZnTiMWW catalyst and the conventionally regenerated ZnTiMWW were compared. The amounts of products obtained and the amount of educt converted were determined by gas chromatography.

For the fresh ZnTiMWW catalyst, the reaction temperature could be kept at 35° C. for most of the reaction time to maintain a conversion rate based on hydrogen peroxide of at least 91%. Also, the selectivities based on hydrogen peroxide and propene remained above 98% during the time period the epoxidation was performed with fresh ZnTiMWW catalyst.

The ZnTiMWW catalyst regenerated conventionally as described in Comparative Example 1 required a significant increase of the reaction temperature to up to 64° C. to maintain a conversion rate based on hydrogen peroxide of at least 91%. While the selectivity based on propene also remained above 98% similar to the fresh ZnTiMWW catalyst, the selectivity based on hydrogen peroxide dropped to 94% after 400 hours when using the ZnTiMWW catalyst regenerated by heating only.

Example 1

One-Time ZnTiMWW Catalyst Regeneration According to the Invention

Two separate regenerations according to the invention were performed at two different washing temperatures. A regeneration was performed by washing the catalyst at 50° C. and another regeneration was performed by washing the catalyst at 70° C. For each experiment, 40 g spent ZnTiMWW catalyst from fractions 1 to 3 of Example 1 were used.

The washing of the ZnTiMWW catalyst was performed in both experiments using a water cooled double mantle glass tube as reactor with a length of 1 m and an inner diameter of 20 mm. The water temperatures were controlled by a thermostat to keep the temperature constant during the respective washing procedure. The water was introduced into the reactor mantle via a pump with a flow rate of 4 ml/min (corresponding to a WHSV of 7 h$^{-1}$) in upflow.

At 50° C., the washing was performed for 420 min. At 70° C., the washing was performed 410 min. In both experiments, the washing was performed until the conductivity of the washing water leaving the reactor at the top was determined to be approx. 200 microSiemens/cm. The conductivity was determined using a conductometer (WTW, LF320) with a standard conductivity measuring cell (Tetra Con 325).

Following the washing, the ZnTiMWW catalyst was dried in both experiments in the double mantle glass reactor in a nitrogen gas stream of 100 l/h at 40° C. for 16 hours, after which the ZnTiMWW catalyst was removed from the reactor and calcinated in an oven at 450° C. in air for 5 hours.

After the regenerations of the ZnTiMWW catalyst at 50° C. and 70° C., the individual compositions were determined by elemental analysis. The elemental analysis was performed as indicated in Reference Example 2 and the results obtained are summarized in Table 1 below.

TABLE 1

Results of Example 1

| | Washing at 50° C. | | | | | Washing at 70° C. | | | | | |
|---|---|---|---|---|---|---|---|---|---|---|---|
| no. | time/min | K/g | P/g | Si/g | Ti/g | Zn/g | time/min | K/g | P/g | Si/g | Ti/g | Zn/g |
| 1 | 0 | 0.34 | 0.27 | 13.5 | 0.45 | 0.41 | 0 | 0.34 | 0.27 | 13.5 | 0.45 | 0.41 |
| 2 | 180 | 0.14 | 0.11 | 0.04 | 0.006 | 0.008 | 170 | 0.20 | 0.14 | 0.06 | 0.005 | 0.010 |
| 3 | 300 | 0.04 | 0.03 | 0.03 | 0.003 | 0.005 | 290 | 0.05 | 0.02 | 0.04 | <0.004 | <0.004 |
| 4 | 420 | 0.03 | 0.01 | 0.02 | 0.002 | 0.004 | 410 | 0.03 | 0.01 | 0.03 | <0.004 | <0.004 |
| 5 | residual wash | 0.01 | <0.01 | <0.01 | <0.001 | 0.001 | residual wash | 0.01 | <0.01 | 0.03 | <0.004 | <0.004 |
| 6 | calcinated | 0.13 | 0.11 | 13.2 | 0.43 | 0.37 | calcinated | 0.06 | 0.09 | 13.2 | 0.39 | 0.36 |

In row no. 1, the amounts in g of the compounds K, P, Si, Ti and Zn in 40 g total amount of ZnTiMWW catalyst before the regeneration are given. In rows no. 2 to 4 the total amounts in g of the compounds K, P, Si, Ti and Zn in the collected wash water within different time periods are indicated (row no. 2: 0 to 180 min; row no. 3: 181 to 300 min; row no. 4: 301 to 420 min). The small losses of Si, Ti and Zn observed during washing are believed to be attributed to small fines formation. In row no. 5, the total amounts in g of these compounds in the residual water removed from the glass tube reactor after finished wash are given. In row no. 6, the total amounts in g of said compounds in the ZnTiMWW catalyst following the completed regeneration, i.e. washing, drying and calcining, are indicated.

Consequently, after approx. 7 hours washing, followed by drying and calcining, the total amounts of K and P have been both reduced favorably by approx. 60% by washing at 50° C. and even more favorably by approx. 82% and 67%, respectively, by washing at 70° C.

At both temperatures the removal of the deposits is satisfactory. However, it is evident that by washing at 70° C. potassium and phosphor deposited on the ZnTiMWW catalyst may be removed faster and more thoroughly.

Example 2

Repeated ZnTiMWW Catalyst Regeneration Performed According to the Invention 34.3 g spent ZnTiMWW of fractions 1 to 3 of Reference Example 2 were submitted to 5 subsequent regenerations as described in Example 1.

The washing was performed each time at 70° C. After each cycle the exact ZnTiMWW catalyst composition and further properties, specifically, its surface, pore volume, crushing strength were determined. Further, a propylene oxide (PO) test was performed which is an indicator for the catalytic activity of the ZnTiMWW catalyst.

The total amounts of K, P, Ti, Zn and Si of the ZnTiMWW catalyst were determined as described in Example 1 by elemental analysis.

The Langmuir surface area was determined via nitrogen adsorption at 77 K according to DIN 66131. The pore volume was determined according to Hg porosimetry according to DIN 66133.

The crush strength as referred to in the context of the present invention is to be understood as determined via a crush strength test machine Z2.5/TS1S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS1S", version 1.5, December 2001 by Zwick GmbH & Co. Technische Dokumentation, August-Nagel-Strasse 11, D-89079 Ulm, Germany. The title page of the instructions handbook is shown in FIG. 9. With said machine, a ZnTiMWW catalyst pellet is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

In a PO test (propylene oxide test), the ZnTiMWW catalyst regenerated according to the process of the present invention is tested in a mini autoclave by reaction of propene with an aqueous hydrogen peroxide solution (30 wt.-%) to yield propylene oxide. In particular, 0.63 g of the ZnTiMWW catalyst are introduced together with 79.2 g of acetonitrile and 12.4 g of propene at room temperature, and 22.1 g of hydrogen peroxide (30 wt.-% in water) are introduced in a steel autoclave. After a reaction time of 4 hours at 40° C., the mixture was cooled and depressurized, and the liquid phase was analyzed by gas chromatography with respect to its propylene oxide content. The propylene oxide content of the liquid phase (in wt.-%) is the result of the PO test.

The results are summarized in Table 2 below.

TABLE 2

Results of Example 2

| Cycle | K/wt.-% | P/wt.-% | Zn/wt.-% | Ti/wt.-% | Si/wt.-% | Langmuir Surface/m$^2$/g | pore volume/ml/g | crush strength/N | PO yield/wt.-% |
|---|---|---|---|---|---|---|---|---|---|
| Fresh Catalyst | 0 | 0 | 1.3 | 1.4 | 43 | 418 | 1.1 | 13 | 8.8 |
| Spent catalyst | 1.10 | 0.78 | 1.2 | 1.3 | 40 | n.d.* | n.d. | n.d. | n.d. |

TABLE 2-continued

Results of Example 2

| Cycle | K/ wt.-% | P/ wt.-% | Zn/ wt.-% | Ti/ wt.-% | Si/ wt.-% | Langmuir Surface/ m²/g | pore volume/ ml/g | crush strength/ N | PO yield/ wt.-% |
|---|---|---|---|---|---|---|---|---|---|
| 1 | 0.22 | 0.30 | 1.2 | 1.3 | 42 | 412 | 1.3 | n.d. | 8.8 |
| 2 | 0.16 | 0.25 | 1.2 | 1.4 | 42 | 403 | 1.2 | 14 | n.d. |
| 3 | 0.08 | 0.19 | 1.2 | 1.4 | 42 | 414 | 1.4 | 13 | n.d. |
| 4 | 0.05 | 0.15 | 1.2 | 1.4 | 42 | 373 | 1.3 | 12 | n.d. |
| 5 | 0.02 | 0.11 | 1.2 | 1.4 | 42 | 416 | 1.4 | 13 | 8.3 | n.d.*—not determined

The results in Table 2 show that the amounts of potassium and phosphor deposits may be further reduced when performing the regeneration process of the present invention subsequently several times.

From Table 2 it becomes also evident that the Zn, Ti and Si contents of the ZnTiMWW catalyst did not change over a process comprising five regeneration cycles compared with the fresh ZnTiMWW catalyst. The slight variations determined are considered to be within the error of measurement.

Further, Table 2 also shows that the Langmuir surface, the pore volume and the crushing strength of the ZnTiMWW catalyst did not change during the repeated regeneration process relative to fresh ZnTiMWW catalyst. Equally, the variations observed for the values determined are considered to be within the error of measurement.

The PO test also showed that the yield of the repeatedly regenerated ZnTiMWW catalyst did not change significantly after five regeneration cycles.

Figure 4:
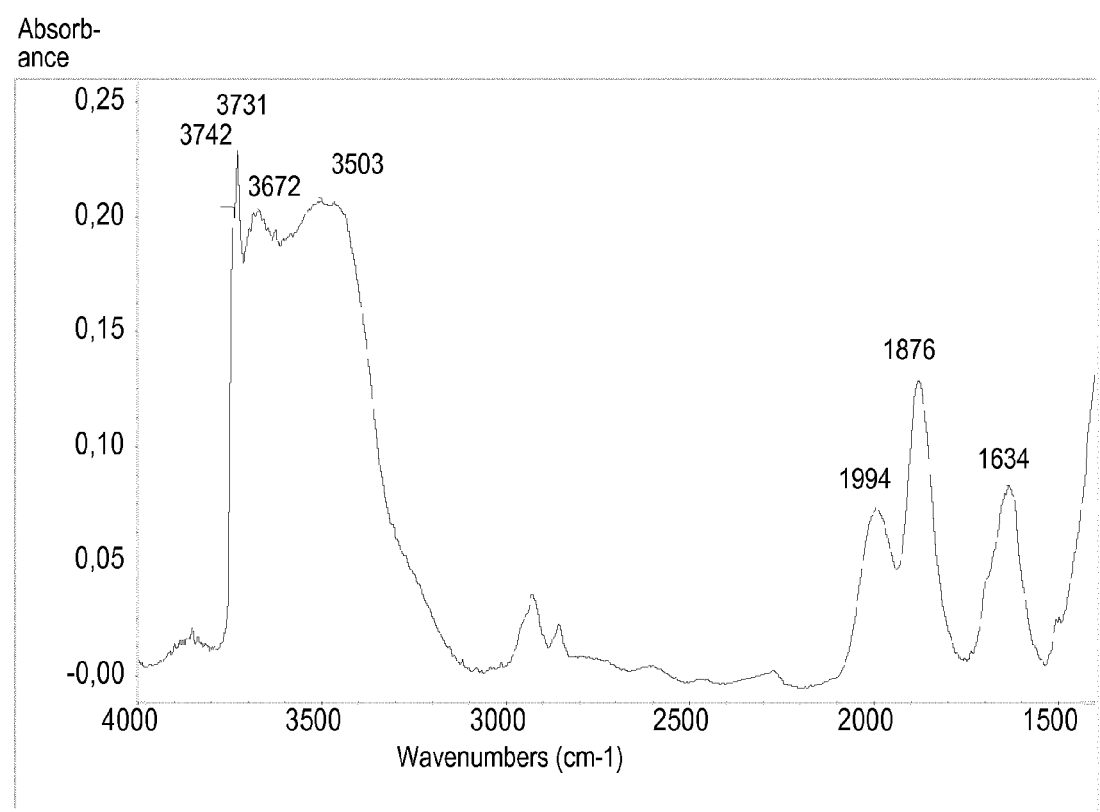
FIG. 4 shows an FT-IR spectrum of fresh catalyst. The x axis shows the wavenumber (wn) in $cm^{-1}$, the y axis shows the absorbance (A).
Figure 5:
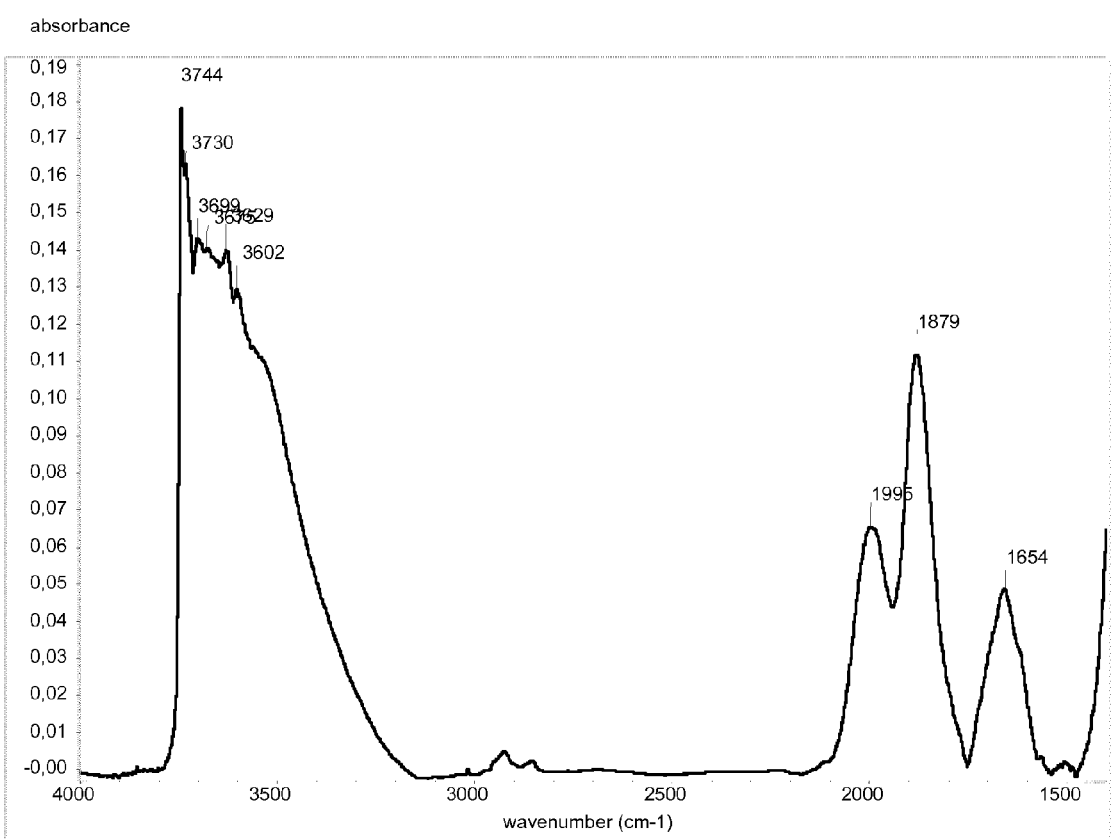
FIG. 5 shows an FT-IR spectrum of spent catalyst following after regeneration cycles, each cycle comprising steps (a) to (b) according to the invention. The x axis shows the wavenumber (wn) in $cm^{-1}$, the y axis shows the absorbance (A).

In addition, an IR spectrum of fresh ZnTiMWW catalyst shown in FIG. 4 may be compared with the IR spectrum recorded with the five times regenerated ZnTiMWW catalyst in FIG. 5. The spectra are largely identical except the band visible at approx. 3500 cm$^{-1}$ in the spectrum of the regenerated ZnTiMWW catalyst. This is an indicator for a decrease of internal silanol nests following regeneration. However, such an alteration does not have an impact on the activity of a zeolitic catalyst as confirmed by the results summarized in Table 2.

In summary, these results indicate consistently that the present process for the regeneration of a catalyst comprising a titanium zeolite as active material, is sufficiently effective, so that the catalytic activity original activity is restored, without even following several regeneration cycles the catalyst is not altered structurally in a significant way.

Example 3

Catalytic Performance of the Multiply Regenerated Catalyst According to the Invention Following the multiple regeneration according to Example 2, the catalytic performance of the regeneration ZnTiMWW catalyst was compared with the catalytic performance of fresh ZnTiMWW catalyst.

Two separate epoxidation reactions were performed in a micro-plant with 15 g fresh ZnTiMWW catalyst and with 15 g multiply regenerated ZnTiMMW catalyst, respectively, at otherwise identical reaction conditions.

The micro-plant comprised water cooled reactor tubes of 1.4 m length and an internal diameter of 7 mm. The feeds introduced in upflow were in each case 68 g/h ACN, 16 g/h $H_2O_2$ (40 weight-% in water), 10.8 g/h propene and a concentration of 130 micromol $KH_2PO_4$ per 1 mol $H_2O_2$ was used. The epoxidation using fresh ZnTiMWW catalyst was terminated after 500 hours, whereas the epoxidation using the multiply regenerated ZnTiMWW catalyst was terminated after 310 hours. The reaction temperatures (i.e. cooling water temperatures) adjusted in each experiment so that at all times the conversion rate of hydrogen peroxide was at least 91%.

Figure 6:
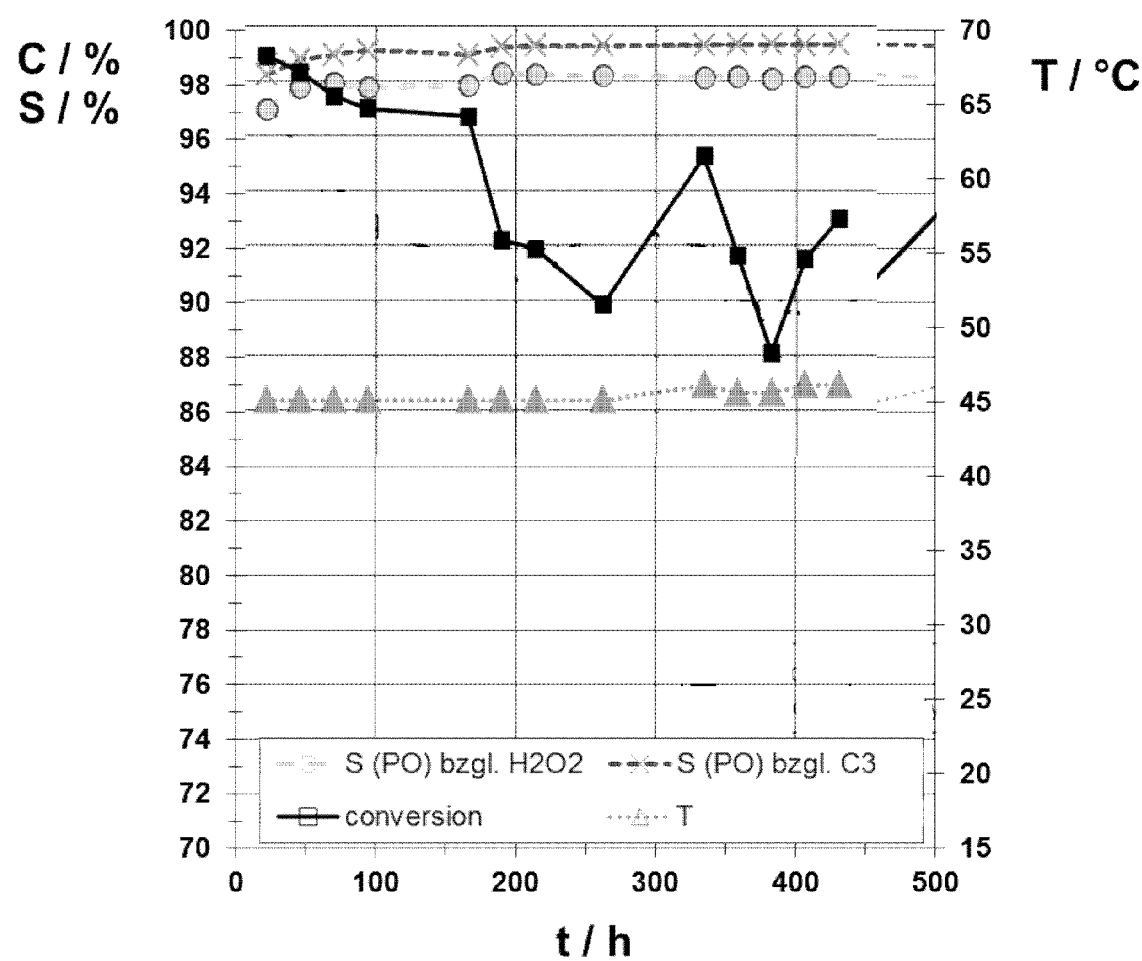
FIG. 6 shows the catalytic performance of spent catalyst having been submitted to five regeneration cycles comprising steps (a) to (b) according to the invention compared with the catalytic performance of fresh catalyst under otherwise identical epoxidation conditions. Indicated are the on hydrogen peroxide conversion rate, the normalized selectivities based on hydrogen peroxide and based on propene of the regenerated catalyst and the fresh catalyst and further the reaction temperature (° C.) applied when using the regenerated catalyst and the fresh catalyst.

In FIG. 6, the selectivity based on hydrogen peroxide, the selectivity based on propene, the conversion rate based on hydrogen peroxide and the reaction temperatures (i.e. cooling water temperatures) required to maintain a conversion rate of at least 91% obtained with fresh and multiply regenerated catalyst, respectively, are compared. The selectivities and the conversion rates were determined as indicated in Comparative Example 2 by gas chromatography.

It is immediately evident that the reaction temperatures required to maintain the hydrogen peroxide conversion rate above 91% are favorably essentially identical when comparing the fresh ZnTiMWW catalyst and the five times regenerated ZnTiMWW catalyst. In both cases the conversion rate at approx. 45° C. remained well above 91%, with the exception of an outlier just below 90° C. after approx. 255 h observed for the multiply regenerated ZnTiMWW catalyst.

Also, the selectivities based both on hydrogen peroxide and on propene remained essentially unchanged displaying a favorably high value of approx. 99% in the course of the epoxidation reaction when comparing ZnTiMWW catalyst regenerated five times according to the invention with fresh ZnTiMWW catalyst.

Example 4

In Situ Regeneration of Spent ZnTiMWW Catalyst According to the Invention

A regeneration according to the present invention was performed on the ZnTiMWW catalyst inside the reactor used for epoxidation in Reference Example 2.

Spent ZnTiMWW catalyst was washed in the 12 m reactor tubes with water at a flow rate of 130 l/h at 60° C. for 17.7 hours, followed by a wash with water at a flow rate of 130 l/h at 75° C. for 4.5 hours. The water was introduced in downflow at the top of the reactor tubes.

Subsequently, the ZnTiMWW catalyst was dried in the reactor in a nitrogen gas stream also introduced at the bottom of the reactor tubes. The nitrogen was introduced with a flow rate of 12 m³/h at a temperature of 60° C. for 96 hours, followed by an introduction of nitrogen at a flow rate of 14 m³/h at 65° C. for 1 h, further followed by an introduction of nitrogen at a flow rate of 13 m³/h at 70° C. for 354.5 h. At the end of the drying step, the humidity of the nitrogen leaving the reactor as determined using a humidity sensor (GE, HygroPro) was 243 ppmV which corresponds to the humidity of the nitrogen gas before introduction in the reactor.

Following the completed drying step, the catalyst was calcinated in the reactor for 6.5 hours at 450° C., wherein the calcining temperature was increased gradually with a rate of 0.5° C./minute.

The properties of the catalyst following the regeneration when reused in an epoxidation procedure were similar to the results obtained in the Examples 1 and 3.

Reference Example 5

Characterization of the Catalyst

Reference Example 5.1

Determination of Dv10, Dv50, and Dv90 Values 1.0 g of the micropowder is suspended in 100 g deionized water and stirred for 1 min. The sample was subjected to the measurement in an apparatus using the following parameters: Master-sizer S long bed version 2.15, ser. No. 33544-325; supplier: Malvern Instruments GmbH, Herrenberg, Germany: focal width 300RF mm; beam length 10.00 mm; module MS17; shadowing 16.9%; dispersion model 3$$D; analysis model polydisperse correction none.

Reference Example 5.2

Determination of the Silanol Concentration of the Moldings of the Present Invention For the determination of the silanol concentration, the $^{29}Si$ MAS NMR experiments were carried out at room temperature on a VARIAN Infinityplus-400 spectrometer using 5.0 mm $ZrO_2$ rotors. The $^{29}Si$ MAS NMR spectra were collected at 79.5 MHz using a 1.9 μs π/4 (microsecond pi/4) pulse with 10 s recycle delay and 4000 scans. All $^{29}Si$ spectra were recorded on samples spun at 6 kHz, and chemical shifts were referenced to 4,4-dimethyl-4-silapentane sulfonate sodium (DSS). For the determination of the silanol group concentration, a given $^{29}Si$ MAS NMR spectrum is deconvolved by the proper Gaussian-Lorentzian line shapes. The concentration of the silanol groups with respect to the total number of Si atoms is obtained by integrating the deconvolved $^{29}Si$ MAS NMR spectra.

Reference Example 5.3

Determination of the Crush Strength of the Moldings

The crush strength as referred to in the context of the present invention is to be understood as determined via a crush strength test machine Z2.5/TS1S, supplier Zwick GmbH & Co., D-89079 Ulm, Germany. As to fundamentals of this machine and its operation, reference is made to the respective instructions handbook "Register 1: Betriebsanleitung/Sicherheitshandbuch für die Material-Prüfmaschine Z2.5/TS1S", version 1.5, December 2001 by Zwick GmbH & Co. Technische Dokumentation, August-Nagel-Strasse 11, D-89079 Ulm, Germany. With said machine, a given strand is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the stands perpendicularly to their longitudinal axis. Controlling the experiment was carried out by means of a computer which registered and evaluated the results of the measurements. The values obtained are the mean value of the measurements for 10 strands in each case.

Reference Example 5.4

$^{29}Si$ Solid-State NMR Spectra Regarding $Q^3$ and $Q^4$ Structures

The effect of the inventive water treatment on the molding related to $Q^3$ and $Q^4$ structures in the material was characterized by comparing the changes in $^{29}Si$ solid-state NMR spectra under comparable conditions. All $^{29}Si$ solid-state NMR experiments were performed using a Bruker Advance spectrometer with 300 MHz$^1H$ Larmor frequency (Bruker Biospin, Germany). Samples were packed in 7 mm $ZrO_2$ rotors, and measured under 5 kHz Magic Angle Spinning at room temperature. $^{29}Si$ direct polarization spectra were obtained using (pi/2)-pulse excitation with 5 microsecond pulse width, a $^{29}Si$ carrier frequency corresponding to −65 ppm in the spectrum, and a scan recycle delay of 120 s. Signal was acquired for 25 ms under 45 kHz high-power proton decoupling, and accumulated over 10 to 17 hours. Spectra were processed using Bruker Topspin with 30 Hz exponential line broadening, manual phasing, and manual baseline correction over the full spectrum width. Spectra were referenced with the polymer Q8M8 as an external secondary standard, setting the resonance of the trimethylsilyl M group to 12.5 ppm. The spectra were then fitted with a set of Gaussian line shapes, according to the number of discernable resonances. Relating to the presently assessed spectra, 6 lines in total were used, accounting for the five distinct peak maxima (at approximately −118, −115, −113, −110 and −104 ppm) plus the clearly visible shoulder at −98 ppm. Fitting was performed using DMFit (Massiot et al., Magnetic Resonance in Chemistry, 40 (2002) pp 70-76). Peaks were manually set at the visible peak maxima or shoulder. Both peak position and line width were then left unrestrained, i.e., fit peaks were not fixed at a certain position. The fitting outcome was numerically stable, i.e., distortions in the initial fit setup as described above did lead to similar results. The fitted peak areas were further used normalized as done by DMFit. After the water treatment of the invention, a decrease of signal intensity at the left hand side of the spectrum was observed, a region that includes $Q^3$ silanol structures (here especially: around and above −104 ppm, i.e. "left" of −104 ppm). Further, an increase of signal at the right hand side of the spectrum (here: below −110 ppm, i.e. "right" of −110 ppm) was observed, which region comprises $Q^4$ structures exclusively. For the quantification of spectrum changes, a ratio was calculated that reflects changes in the peak areas "left hand" and "right hand", as follows. The six peaks were labeled with 1, 2, 3, 4, 5, and 6, and the ratio Q was calculated with the formula 100*{

$[a_1+a_2]/[a_4+a_5+a_6]\}/a_3$. In this formula, $a_{i,i=1..6}$ represents the area of the fitted peak to which this number was attributed.

Reference Example 5.5

Water Adsorption/Desorption-Water Uptake

The water adsorption/desorption isotherms measurements were performed on a VTI SA instrument from TA Instruments following a step-isotherm program. The experiment consisted of a run or a series of runs performed on a sample material that has been placed on the microbalance pan inside of the instrument. Before the measurement were started, the residual moisture of the sample was removed by heating the sample to 100° C. (heating ramp of 5° C./min) and holding it for 6 h under a $N_2$ flow. After the drying program, the temperature in the cell was decreased to 25° C. and kept isothermal during the measurements. The microbalance was calibrated, and the weight of the dried sample was balanced (maximum mass deviation 0.01 wt. %). Water uptake by the sample was measured as the increase in weight over that of the dry sample. First, an adsorption curve was measured by increasing the relative humidity (RH) (expressed as weight-% water in the atmosphere inside of the cell) to which the samples was exposed and measuring the water uptake by the sample at equilibrium. The RH was increased with a step of 10 wt. % from 5 to 85% and at each step the system controlled the RH and monitored the sample weight until reaching the equilibrium conditions and recording the weight up-take. The total adsorbed water amount by the sample was taken after the sample was exposed to the 85 weight-% RH. During the desorption measurement the RH was decreased from 85 wt. % to 5 wt. % with a step of 10% and the change in the weight of the sample (water uptake) was monitored and recorded.

Reference Example 5.6

FT-IR Measurements

The FT-IR (Fourier-Transformed-Infrared) measurements were performed on a Nicolet 6700 spectrometer. The molding was powdered and then pressed into a self-supporting pellet without the use of any additives. The pellet was introduced into a high vacuum (HV) cell placed into the FT-IR instrument. Prior to the measurement the sample was pretreated in high vacuum ($10^{-5}$ mbar) for 3 h at 300° C. The spectra were collected after cooling the cell to 50° C. The spectra were recorded in the range of 4000 to 800 $cm^{-1}$ at a resolution of 2 $cm^{-1}$. The obtained spectra are represented in a plot having on the x axis the wavenumber ($cm^{-1}$) and on the y axis the absorbance (arbitrary units, a.u.). For the quantitative determination of the peak heights and the ratio between these peaks a baseline correction was carried out. Changes in the 3000-3900 cm region were analyzed and for comparing multiple samples, as reference the band at 1880±5 $cm^{-1}$ was taken.

Reference Example 5.7

Determination of Crystallinity Via XRD

The crystallinity of the zeolitic materials according to the present invention were determined by XRD analysis. The data were collected using a standard Bragg-Brentano diffractometer with a Cu-X-ray source and an energy dispersive point detector. The angular range of 2° to 70° (2 theta) was scanned with a step size of 0.02°, while the variable divergence slit was set to a constant illuminated sample length of 20 mm.

The data were then analyzed using TOPAS V4 software, wherein the sharp diffraction peaks were modeled using a Pawley fit containing a unit cell with the following starting parameters: a=14.4 Angstrom (1 Angstrom=$10^{-10}$ m) and c=25.2 Angstrom in the space group P6/mmm. These were refined to fit the data. Independent peaks were inserted at the following positions. 8.4°, 22.4°, 28.2° and 43°. These were used to describe the amorphous content. The crystalline content describes the intensity of the crystalline signal to the total scattered intensity. Included in the model were also a linear background, Lorentz and polarization corrections, lattice parameters, space group and crystallite size.

CITED LITERATURE

WO-A 98/55229
WO-A 2011/064191
EP-A 0 934 116
EP-A 0 790 07
EP-A 1 371 414
EP-A 1 221 442
WO-A 2005/000827
WO-A 2007/013739
EP-A 1 122 249
US 2003/0187284 A1
US 2012/142950 A1
WO 2011/115234 A1
US 2004/058798 A1
U.S. Pat. No. 5,916,835 A

The invention claimed is:

1. A process for the regeneration of a catalyst comprising a titanium containing zeolite as catalytically active material, said catalyst having been used in a process for the preparation of an olefin oxide comprising
    (i) providing a mixture comprising an organic solvent, an olefin, an epoxidation agent and an at least partially dissolved potassium comprising salt;
    (ii) subjecting the mixture provided in (i) in a reactor to epoxidation conditions in the presence of the catalyst, obtaining a mixture comprising the organic solvent and the olefin oxide, and obtaining the catalyst having a potassium salt deposited thereon;
    said process for the regeneration comprising
    (a) separating the mixture obtained from (ii) from the catalyst;
    (b) washing the catalyst obtained from (a) with a liquid aqueous system; which comprises less than 0.1 wt. -% of compounds with a pKa value of 8 or less;
    (c) optionally drying the catalyst obtained from (b) in a gas stream comprising an inert gas at a temperature of less than 300° C.;
    (d) calcining the catalyst obtained from (b) or (c) in a gas stream comprising oxygen at a temperature of at least 300° C.

2. The process of claim 1, wherein the liquid aqueous system used in (b) contains at least 75 weight water, based on a total weight of the liquid aqueous system.

3. The process of claim 1, wherein the washing (b) is performed at a pressure in a range of from 0.8 to 1.5 bar, and a temperature in a range of from 40 to 90° C.

4. The process of claim 1, wherein the washing (b) is performed until a potassium content of the liquid aqueous system after having been contacted with the catalyst is at most 1000 weight-ppm.

5. The process of claim 1, wherein the washing (b) is performed until a potassium content of the liquid aqueous system after having been contacted with the catalyst relative to the potassium content of the liquid aqueous system before having been contacted with the catalyst is at most 333:1.

6. The process of claim 1, wherein the process comprises the drying (c) and at least 90 volume-% of the gas stream comprising the inert gas consist of at least one inert gas selected from the group consisting of nitrogen, helium, and argon.

7. The process of claim 1, wherein the process comprises the drying (c), which is performed until a water content of the gas stream comprising the inert gas after having been contacted with the catalyst relative to a water content of the gas stream comprising the inert gas before having been contacted with the catalyst is at most 1.10:1.

8. The process of claim 1, wherein the process comprises the drying (c) and after (c), the dried catalyst is heated to the calcination temperature according to (d) with a rate in a range of from 0.5 to 5 K/min.

9. The process of claim 1, wherein the catalyst obtained from (d) has a potassium content of at most 0.5 weight-%, based on a total weight of the catalyst and determined via elemental analysis.

10. The process of claim 1, wherein the mixture provided in (i) has a potassium content with a molar range of potassium relative to the epoxidation agent comprised in the mixture in a range of from $10 \times 10^{-6}$:1 to $1500 \times 10^{-6}$:1.

11. The process of claim 1, wherein the at least partially dissolved potassium comprising salt in (i) is selected from the group consisting of an inorganic potassium salt, an organic potassium salt, and a combination thereof.

12. The process of claim 1, wherein the at least partially dissolved potassium comprising salt in (i) is selected from the group consisting of
at least one inorganic potassium salt selected from the group consisting of potassium hydroxide, a potassium halide, potassium nitrate, potassium sulfate, potassium hydrogen sulfate, potassium perchlorate, potassium dihydrogen phosphate, dipotassium hydrogen phosphate, potassium phosphate, a potassium pyrophosphate, and a potassium etidronate,
at least one organic potassium salt selected from the group consisting of a potassium salt of an aliphatic saturated monocarboxylic acid, potassium carbonate, and potassium hydrogen carbonate, and
a combination of the at least one inorganic potassium salt and the at least one organic potassium salt.

13. The process of claim 1, wherein the titanium containing zeolite has an MFI framework structure, an MEL framework structure, an MWW framework structure, an MWW-type framework structure, an ITQ framework structure, a BEA framework structure, a MOR framework structure, or a mixed structure of two or more thereof.

14. The process of claim 1, wherein the titanium containing zeolite comprises at least one of Al, B, Zr, V, Nb, Ta, Cr, Mo, W, Mn, Fe, Co, Ni, Zn, Ga, Ge, In, Sn, Pb, Pd, Pt, and Au.

15. The process of claim 1, wherein the titanium containing zeolite is an aluminum-free zeolitic material of MWW or MWW-type framework structure comprising titanium.

16. The process of claim 1, wherein the catalyst comprising the titanium containing zeolite is a micropowder.

17. The process of claim 16, wherein the molding further comprises at least one binder.

18. The process of claim 1, wherein the process for the regeneration is carried out in the reactor in which the mixture provided in (i) is subjected to epoxidation conditions according to (ii).

19. The process of claim 1, further comprising
employing the catalyst obtained from (d) in an olefin epoxidation process comprising
(i') providing a mixture comprising an organic solvent, an olefin, an epoxidation agent and an at least partially dissolved potassium comprising salt; and
(ii') subjecting the mixture provided in (i') in a reactor to epoxidation conditions in the presence of the catalyst obtained from (d), obtaining a mixture comprising the organic solvent and the olefin oxide.

* * * * *